US007455991B2

(12) United States Patent
Afar et al.

(10) Patent No.: US 7,455,991 B2
(45) Date of Patent: *Nov. 25, 2008

(54) SERPENTINE TRANSMEMBRANE ANTIGENS EXPRESSED IN HUMAN CANCERS AND USES THEREOF

(75) Inventors: Daniel E. H. Afar, Brisbane, CA (US); Rene S. Hubert, Los Angeles, CA (US); Arthur B. Raitano, Los Angeles, CA (US); Douglas Saffran, Encinitas, CA (US); Steven Chappell Mitchell, Gurnee, IL (US)

(73) Assignee: Agensys, Inc., Santa Monica, CA (US)

( * ) Notice: Subject to any disclaimer, the term of this patent is extended or adjusted under 35 U.S.C. 154(b) by 570 days.

This patent is subject to a terminal disclaimer.

(21) Appl. No.: 10/752,421

(22) Filed: Jan. 5, 2004

(65) Prior Publication Data
US 2005/0063975 A1    Mar. 24, 2005

Related U.S. Application Data

(60) Division of application No. 09/455,486, filed on Dec. 6, 1999, now Pat. No. 6,833,438, which is a continuation-in-part of application No. 09/323,873, filed on Jun. 1, 1999, now Pat. No. 6,329,503.

(51) Int. Cl.
C07H 21/02 (2006.01)
C12N 15/63 (2006.01)
(52) U.S. Cl. .................. 435/69.1; 536/23.1; 435/320.1
(58) Field of Classification Search ........................ None
See application file for complete search history.

(56) References Cited

U.S. PATENT DOCUMENTS

| 6,262,245 B1 * | 7/2001 | Xu et al. ..................... 536/23.5 |
| 6,329,503 B1 | 12/2001 | Afar et al. .................... 530/350 |
| 2002/0022248 A1 | 2/2002 | Xu et al. ..................... 435/69.1 |
| 2003/0045682 A1 | 3/2003 | Afar et al. |
| 2003/0060612 A1 | 3/2003 | Goddard et al. ............ 536/23.1 |
| 2003/0064397 A1 | 4/2003 | Spancake et al. ............... 435/6 |

FOREIGN PATENT DOCUMENTS

| EP | 0834563 | 4/1998 |
| EP | 1308459 | 5/2003 |
| WO | WO94/09150 | 4/1994 |
| WO | WO98/18489 | 5/1998 |
| WO | WO98/37093 | 8/1998 |
| WO | WO98/37418 | 8/1998 |
| WO | WO98/53071 | 11/1998 |
| WO | WO99/06548 | 2/1999 |
| WO | WO99/06550 | 2/1999 |
| WO | WO99/61469 | 2/1999 |
| WO | WO 99/62941 | 12/1999 |
| WO | WO99/62941 | 12/1999 |
| WO | WO 00/04149 | 1/2000 |
| WO | WO 00/35937 | 6/2000 |
| WO | WO 01/12662 | 2/2001 |
| WO | WO 01/40276 | 6/2001 |
| WO | WO 01/72962 | 10/2001 |
| WO | WO 02/16429 | 2/2002 |
| WO | WO 02/26822 | 4/2002 |
| WO | WO 02/057303 | 7/2002 |
| WO | WO 02/059260 | 8/2002 |
| WO | WO 02/095010 | 11/2002 |
| WO | WO 02/102993 | 12/2002 |
| WO | WO 02/102994 | 12/2002 |
| WO | WO 03/004622 | 1/2003 |
| WO | WO 03/004623 | 1/2003 |
| WO | WO 03/009814 | 2/2003 |

(Continued)

OTHER PUBLICATIONS

Freshney (Culture of Animal Cells, A Manual of Basic Technique, Alan R. Liss, Inc., 1983, New York, p4).*
Dermer (Bio/Technology, 1994, 12:320).*
Fu et al (EMBO Journal, 1996, vol. 15, pp. 4392-4401).*
Brennan et al (Journal of Autoimmunity, 1989, vol. 2 suppl., pp 177-186).*
Zimmer (Cell Motility and the Cytoskeleton, 1991, vol. 20, pp. 325-337).*
Eriksson et al. (Diabetologia, 1992, vol. 35, pp. 143-147).*
Boehringer Mannheim Biochemicals, 1994 Catalog, p. 93.*
Abu-Threideh et al., Jun. 1998, EMBL/GENBANK/DDBJ Databases.

(Continued)

Primary Examiner—Misook Yu
(74) Attorney, Agent, or Firm—Atulya R. Agarwal; Shane M. Popp, J. D., L.L.M.; Ginger R. Dreger, Esq.

(57) ABSTRACT

Described is a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigen of the Prostate). Four particular human STEAPs are described and characterized herein. The human STEAPs exhibit a high degree of structural conservation among them but show no significant structural homology to any known human proteins. The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers.

6 Claims, 38 Drawing Sheets

FOREIGN PATENT DOCUMENTS

| WO | WO 03/022995 | 3/2003 |
| WO | WO 2005/113601 A2 | 12/2005 |
| WO | WO 2006/034488 A2 | 3/2006 |

OTHER PUBLICATIONS

Abu-Threideh et al., GENBANK, (Accession No. O95034), National Library of Medicine, Bethesda MD, May 1, 1999.
Alberts et al., Molecular Biology of the Cell, 3rd edition (1994) p. 465.
Bellone et al., Immunology Today (1999) 20(10):457-462.
Bowie et al. (1990) Science 247:1306-1310.
Burgess et al. (1990) Jnl. Cell Biol. 111:2129-2138.
Cate et al., GENBANK, (Accession No. W86309), National Library of Medicine, Bethesda MD, Nov. 1998.
Database EMBL Nucleotide and Protein Sequences, Aug. 25, 1996, XP002128081, AA032221, Hinxton, GB.
Database EMBL Nucleotide and Protein Sequences, May 13, 1997, XP002128082, AC002064, Hinxton, GB.
Database EMBL Nucleotide and Protein Sequences, Jun. 15, 1998, XP002128084, AC004969 (clone DJ1121E10), Hinxton, GB.
Database EMBL, "Human BAC clone CTB-167B5 form 7q21, complete sequence," Jun. 17, 1998.
Database EMBL Nucleotide and Protein Sequences, May 1, 1999, XP002128083, O95034 (clone RG041D11), Hinxton, GB.
Diss et al. (1998) "Expression of skeletal muscle-type voltage-gated Na+ channel in rat and human prostate cancer cell lines," FEBS Letters 427:5-10.
Dulcert et al., GENBANK, (Accession No. Y11840), National Library of Medicine, Bethesda MD, Feb. 11, 1999.
Falk et al., Nature (1991) 351:390-296.
Fu et al., EMBO Journal (1996) 15:4392-4401.
Greenberg et al., PNAS (1995) 92:3439.
Greenspan et al., (Nature Biotechnology 7:936-937 (1999)).
Grimes et al. (1998) "Electrophysiological characterization of voltage-gated $Na^+$ current expressed in the highly metastatic Mat-LyLu cell line of rat prostate cancer," Journal of Cellular Physiology 175:50-58.
Gura, Science (1997) 278:1041-1042.
Gutierrez et al. (1999) "Activation of a $Ca^{2+}$-permeable cation channel by two different inducers of appoptosis in a human prostatic cancer cell line," Journal of Physiology 517.1:95-107.
Haverstick et al. (2000) "Inhibition of human prostate cancer proliferation in vitro and in a mouse model by a compound synthesized to block $Ca^{2+}$ Entry[1]," Cancer Research pp. 1002-1008.
Herbert et al. (The Dictionary of Immunology, Academic Press, 4th edition, 1995).
Hubert et al. (1999) PNAS USA 96(25):14523-14528.
Hunt et al., Science (1992) 255:1261-1263.
International Search Report mailed on Apr. 28, 2003, for PCT patent application No. PCT/US02/28371 filed on Sep. 6, 2002, 1 page.
Lal et al. (US Patent No. 6048970, May 1998, USPTO database sequence listing).
Lazar et al. (1988) Mol. Cell. Biol. 8(3):1247-1252.
Lepple-Wienhues et al. (1996) "K + Channels and the intracellular calcium signal in human melanoma cell proliferation," J. Membrane Biol. 151:149-157.
Lewin, Genes VI, Oxford University Press, Inc., NY, Chapter 29, 1997.
Marino et al. (1994) "Association between cell membrane potential and breast cancer," Tumor Biol. 15:82-89.
McClean et al., Eur. J. of Cancer (1993) 29A:2243-2248.
Muller et al., MCB (1991) 11:1785.
Nie et al. (1997) "Inhibition of proliferation of MCF-7 breast cancer cells by a blocker of $Ca^{2+}$-permeable channel," Cell Calcium 22(2):75-82, unknown.
Pancrazio et al. (1989) "Voltage-dependent ion channels in small-cell lung cancer cells[1]," Cancer Research 49:5901-5906.
Parker et al., J. Immunol. (1994) 152:163-175.
Peshwa et al., Prostate (1998) 36:129-138.
Rama et al.. Biochem. J. 318:333-341 (1996).
Rieger et al., Glossary of Genetics and Cytogenetics, Springer-Verlag (1976) p. 17.
Shantz et al., Int. J. of Biochem. and Cell Bio. (1999) 31:107-122.
Skryma et al., (1997) "Potassium conductance in the androgen-sensitive prostate cancer cell line, LNCaP: involvement in cell proliferation," The Prostate 33:112-122.
Spitler, Cancer Biotherapy (1995) 10:1-3.
Stewart et al., Genome Res. (1997) 7:422.
Walter et al., Nat. Genetics (1994) 7:22.
Xue et al., Prostate (1997) 30:73-78.
Challita-Eid et al., "Monoclonal Antibodies to Six-Transmembrane Epithelial Antigen of the Prostate-1 Inhibit Intercellular Communication in Vitro and Growth of Human Tumor Xenografts in Vivo" Cancer Research, 61(12):5798-5805 (2007). XP002469628; ISSN: 0008-5472 (Abstract).
Faris et al., "Validation of Steap-1 as a Cell Surface Cancer Therapeutic Target" Proceedings of the Annual Meeting of the American Association for Cancer Research, New York, NY, US. 43:947 (2002). XP001207871, ISSN: 0197-016X.
Hubert et al., "STEAP: A Prostate-Specific Cell Surface Antigen Highly Expressed in Human Prostate Tumors" Proceedings of the National Academy of Sciences of USA, National Academy of Science, Washington, DC, US 96(25)14523-14528 (1999). XP00946864; ISSN: 0027-8424.

\* cited by examiner

FIG. 1A-1

```
           11             20             29             38             47             56
5' GAG ACT CAC GGT CAA GCT AAG GCG AAG AGT GGG TGG CTG AAG CCA TAC TAT TTT
   --- --- --- --- --- --- --- --- --- --- --- --- --- --- --- --- --- ---

65             74             83             92            101            110
   ATA GAA TTA ATG GAA AGC AGA AAA GAC ATC ACA AAC CAA GAA GAA CTT TGG AAA
   --- --- --- --- --- --- --- --- --- --- --- --- --- --- --- --- --- ---
                M   E   S   R   K   D   I   T   N   Q   E   E   L   W   K 119            128            137            146            155            164
   ATG AAG CCT AGG AGA AAT TTA GAA GAA GAC GAT TAT TTG CAT AAG GAC ACG GGA
   --- --- --- --- --- --- --- --- --- --- --- --- --- --- --- --- --- ---
    M   K   P   R   R   N   L   E   E   D   D   Y   L   H   K   D   T   G 173            182            191            200            209            218
   GAG ACC AGC ATG CTA AAA AGA CCT GTG CTT TTG CAT TTG CAC CAA ACA GCC CAT
   --- --- --- --- --- --- --- --- --- --- --- --- --- --- --- --- --- ---
    E   T   S   M   L   K   R   P   V   L   L   H   L   H   Q   T   A   H 227            236            245            254            263            272
   GCT GAT GAA TTT GAC TGC CCT TCA GAA CTT CAG CAC ACA CAG GAA CTC TTT CCA
   --- --- --- --- --- --- --- --- --- --- --- --- --- --- --- --- --- ---
    A   D   E   F   D   C   P   S   E   L   Q   H   T   Q   E   L   F   P 281            290            299            308            317            326
   CAG TGG CAC TTG CCA ATT AAA ATA GCT GCT ATT ATA GCA TCT CTG ACT TTT CTT
   --- --- --- --- --- --- --- --- --- --- --- --- --- --- --- --- --- ---
    Q   W   H   L   P   I   K   I   A   A   I   I   A   S   L   T   F   L 335            344            353            362            371            380
   TAC ACT CTT CTG AGG GAA GTA ATT CAC CCT TTA GCA ACT TCC CAT CAA CAA TAT
   --- --- --- --- --- --- --- --- --- --- --- --- --- --- --- --- --- ---
    Y   T   L   L   R   E   V   I   H   P   L   A   T   S   H   Q   Q   Y 389            398            407            416            425            434
   TTT TAT AAA ATT CCA ATC CTG GTC ATC AAC AAA GTC TTG CCA ATG GTT TCC ATC
   --- --- --- --- --- --- --- --- --- --- --- --- --- --- --- --- --- ---
    F   Y   K   I   P   I   L   V   I   N   K   V   L   P   M   V   S   I 443            452            461            470            479            488
   ACT CTC TTG GCA TTG GTT TAC CTG CCA GGT GTG ATA GCA GCA ATT GTC CAA CTT
   --- --- --- --- --- --- --- --- --- --- --- --- --- --- --- --- --- ---
    T   L   L   A   L   V   Y   L   P   G   V   I   A   A   I   V   Q   L 497            506            515            524            533            542
   CAT AAT GGA ACC AAG TAT AAG AAG TTT CCA CAT TGG TTG GAT AAG TGG ATG TTA
   --- --- --- --- --- --- --- --- --- --- --- --- --- --- --- --- --- ---
    H   N   G   T   K   Y   K   K   F   P   H   W   L   D   K   W   M   L 551            560            569            578            587            596
   ACA AGA AAG CAG TTT GGG CTT CTC AGT TTC TTT TTT GCT GTA CTG CAT GCA ATT
   --- --- --- --- --- --- --- --- --- --- --- --- --- --- --- --- --- ---
    T   R   K   Q   F   G   L   L   S   F   F   F   A   V   L   H   A   I
```

FIG. 1A-2

```
            605             614             623             632             641             650
    TAT AGT CTG TCT TAC CCA ATG AGG CGA TCC TAC AGA TAC AAG TTG CTA AAC TGG
    --- --- --- --- --- --- --- --- --- --- --- --- --- --- --- --- --- ---
     Y   S   L   S   Y   P   M   R   R   S   Y   R   Y   K   L   L   N   W 659             668             677             686             695             704
    GCA TAT CAA CAG GTC CAA CAA AAT AAA GAA GAT GCC TGG ATT GAG CAT GAT GTT
    --- --- --- --- --- --- --- --- --- --- --- --- --- --- --- --- --- ---
     A   Y   Q   Q   V   Q   Q   N   K   E   D   A   W   I   E   H   D   V 713             722             731             740             749             758
    TGG AGA ATG GAG ATT TAT GTG TCT CTG GGA ATT GTG GGA TTG GCA ATA CTG GCT
    --- --- --- --- --- --- --- --- --- --- --- --- --- --- --- --- --- ---
     W   R   M   E   I   Y   V   S   L   G   I   V   G   L   A   I   L   A 767             776             785             794             803             812
    CTG TTG GCT GTG ACA TCT ATT CCA TCT GTG AGT GAC TCT TTG ACA TGG AGA GAA
    --- --- --- --- --- --- --- --- --- --- --- --- --- --- --- --- --- ---
     L   L   A   V   T   S   I   P   S   V   S   D   S   L   T   W   R   E 821             830             839             848             857             866
    TTT CAC TAT ATT CAG AGC AAG CTA GGA ATT GTT TCC CTT CTA CTG GGC ACA ATA
    --- --- --- --- --- --- --- --- --- --- --- --- --- --- --- --- --- ---
     F   H   Y   I   Q   S   K   L   G   I   V   S   L   L   L   G   T   I 875             884             893             902             911             920
    CAC GCA TTG ATT TTT GCC TGG AAT AAG TGG ATA GAT ATA AAA CAA TTT GTA TGG
    --- --- --- --- --- --- --- --- --- --- --- --- --- --- --- --- --- ---
     H   A   L   I   F   A   W   N   K   W   I   D   I   K   Q   F   V   W 929             938             947             956             965             974
    TAT ACA CCT CCA ACT TTT ATG ATA GCT GTT TTC CTT CCA ATT GTT GTC CTG ATA
    --- --- --- --- --- --- --- --- --- --- --- --- --- --- --- --- --- ---
     Y   T   P   P   T   F   M   I   A   V   F   L   P   I   V   V   L   I 983             992             1001            1010            1019            1028
    TTT AAA AGC ATA CTA TTC CTG CCA TGC TTG AGG AAG AAG ATA CTG AAG ATT AGA
    --- --- --- --- --- --- --- --- --- --- --- --- --- --- --- --- --- ---
     F   K   S   I   L   F   L   P   C   L   R   K   K   I   L   K   I   R 1037            1046            1055            1064            1073            1082
    CAT GGT TGG GAA GAC GTC ACC AAA ATT AAC AAA ACT GAG ATA TGT TCC CAG TTG
    --- --- --- --- --- --- --- --- --- --- --- --- --- --- --- --- --- ---
     H   G   W   E   D   V   T   K   I   N   K   T   E   I   C   S   Q   L 1091            1100            1109            1118            1127            1136
    TAG AAT TAC TGT TTA CAC ACA TTT TTG TTC AAT ATT GAT ATA TTT TAT CAC CAA
    --- --- --- --- --- --- --- --- --- --- --- --- --- --- --- --- --- ---
     *   N   Y   C   L   H   T   F   L   F   N   I   D   I   F   Y   H   Q 1145            1154            1163            1172            1181            1190
    CAT TTC AAG TTT GTA TTT GTT AAT AAA ATG ATT ATT CAA GGA AAA AAA AAA AAA
    --- --- --- --- --- --- --- --- --- --- --- --- --- --- --- --- --- ---
     H   F   K   F   V   F   V   N   K   M   I   I   Q   G   K   K   K   K

AAA AA 3'    SEQ ID NO:1
    --- --
     K           SEQ ID NO:2
```

FIG. 1C

5'  GGC GGA GGC GGA GGC GGA GGG CGA GGG GCG GGG AGC GCC GCC TGG AGC GCG

GCA GGT CAT ATT GAA CAT TCC AGA TAC CTA TCA TTA CTC GAT GCT GTT GAT

AAC AGC AAG    3' SEQ ID NO:3

FIG. 2
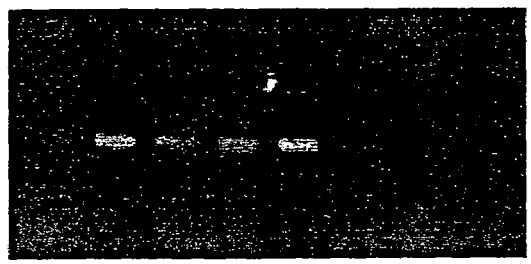
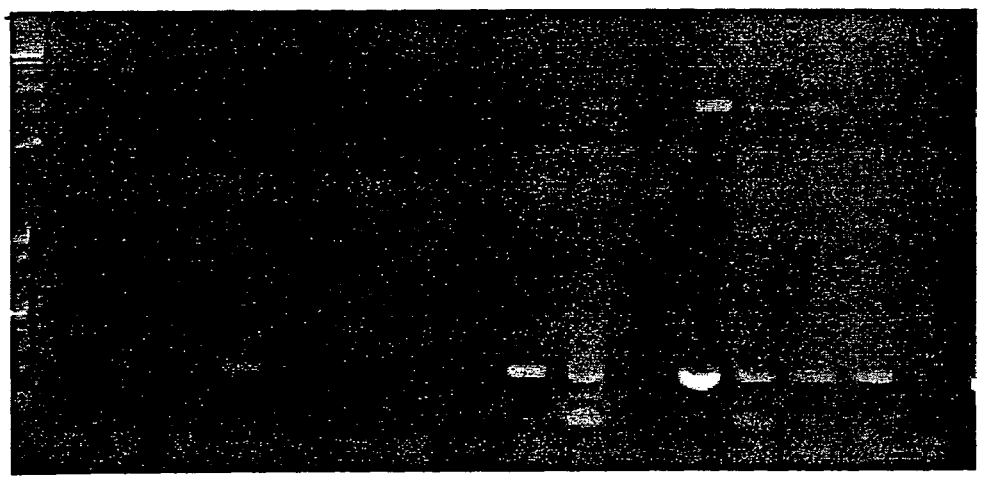
Panels:
A
1. Brain
2. Prostate
3. LAPC-4 AD
4. LAPC-4 AI
5. LAPC-9 AD
6. HeLa
7. Murine cDNA
8. Neg. control
B
1. Brain
2. Heart
3. Kidney
4. Liver
5. Lung
6. Pancreas
7. Placenta
8. Skeletal Muscle
C
1. Colon
2. Ovary
3. Leukocytes
4. Prostate
5. Small Intestine
6. Spleen
7. Testis
8. Thymus

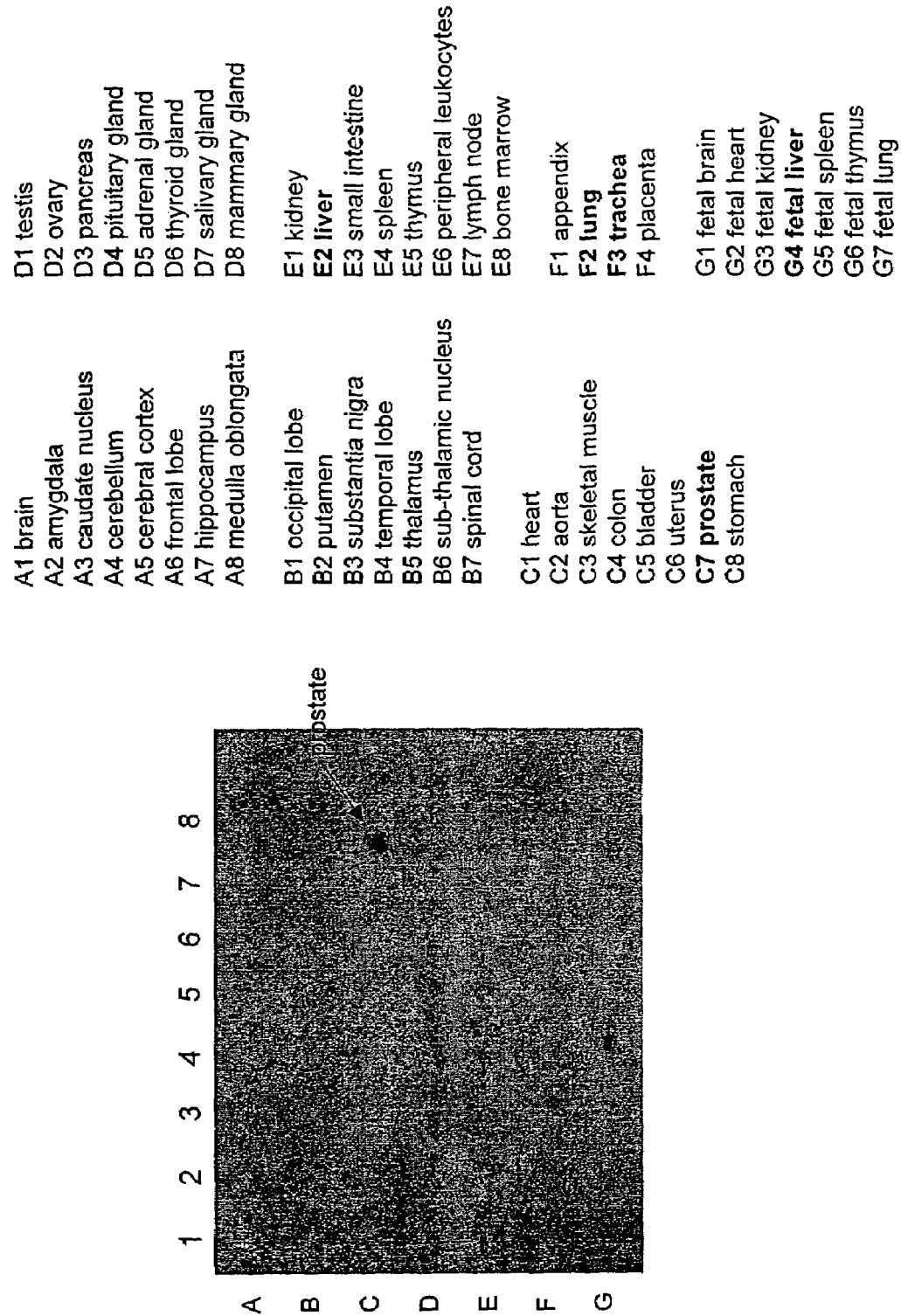

FIG. 3B

| | |
|---|---|
| A1 brain | D1 testis |
| A2 amygdala | D2 ovary |
| A3 caudate nucleus | D3 pancreas |
| A4 cerebellum | D4 pituitary gland |
| A5 cerebral cortex | D5 adrenal gland |
| A6 frontal lobe | D6 thyroid gland |
| A7 hippocampus | D7 salivary gland |
| A8 medulla oblongata | D8 mammary gland |
| B1 occipital lobe | E1 kidney |
| B2 putamen | E2 liver |
| B3 substantia nigra | E3 small intestine |
| B4 temporal lobe | E4 spleen |
| B5 thalamus | E5 thymus |
| B6 sub-thalamic nucleus | E6 peripheral leukocytes |
| B7 spinal cord | E7 lymph node |
| | E8 bone marrow |
| C1 heart | F1 appendix |
| C2 aorta | F2 lung |
| C3 skeletal muscle | F3 trachea |
| C4 colon | F4 placenta |
| C5 bladder | |
| C6 uterus | G1 fetal brain |
| C7 prostate | G2 fetal heart |
| C8 stomach | G3 fetal kidney |
| | G4 fetal liver |
| | G5 fetal spleen |
| | G6 fetal thymus |
| | G7 fetal lung |

FIG. 4A

GGGGCCCGCACCTCTGGGCAGCAGCGGCAGCCGAGACTCACGGTCAAGCTAAGGCGAAGAGTGGGTGGCTGAAGCC

ATACTATTTTATAGAATTAATGGAAAGCAGAAAAGACATCACAAACCAAGAAGAACTTTGGAAAATGAAGCCTAGG

AGAAATTTAGAAGAAGACGATTATTTGCATAAGGACACGGGAGAGACCAGCATGCTAAAAAGACCTGTGCTTTTGC

ATTTGCACCAAACAGCCCATGCTGATGAATTTGACTGCCCTTCAGAACTTCAGCACACACAGGAACTCTTTCCACA

GTGGCACTTGCCAATTAAAATAGCTGCTATTATAGCATCTCTGACTTTTCTTTACACTCTTCTGAGGGAAGTAATT

CACCCCTTAGCAACTTCCCATCAACAATATTTTTATAAAATTCCAATCCTGGTCATCAACAAAGTCTTGCCAATGG

TTTCCATCACTCTCTTGGCATTGGTTTACCTGCCAGGTGTGATAGCAGCAATTGTCCAACTTCATAATGGAACCAA

GTATAAGAAGTTTCCACATTGGTTGGATAAGTGGATGTTAACAAGAAAGCAGTTTGGGCTTCTCAGTTTCTTTTTT

GCTGTACTGCATGCAATTTATAGTCTGTCTTACCCAATGAGGCGATCCTACAGATACAAGTTGCTAAACTGGGCAT

ATCAACAGGTCCAACAAAATAAAGAAGATGCCTGGATTGAGCATGATGTTTGGAGAATGGAGATTTATGTGTCTCT

GGGAATTGTGGGATTGGCAATACTGGCTCTGTTGGCTGTGACATCTATTCCATCTGTGAGTGACTCTTTGACATGG

AGAGAATTTCACTATATTCAGGTAAATAATATATAAAATAACCCTAAGAGGTAAATCTTCTTTTTGTGTTTATGAT

ATAGAATATGTTGACTTTACCCCATAAAAAATAACAAATGTTTTTCAACAGCAAAGATCTTATACTTGTTCCAATT

AATAATGTGCTCTCCTGTTGTTTTCCCTATTGCTTCTAATTAGGACAAGTGTTTCCTAGACATAAATAAAAGGCAT

TAAAATATTCTTTGTTTTTTTTTTTTGTTTGTTTGTTTTTTGTTTGTTTGTTTGTTTTTTTGAGATGAAGTCTCG

CTCTGTTGCCCATGCTGGAGTACAGTGGCACGATCTCGGCTCACTGCAACCTGCGCCTCCTGGGTTCAGGCGATTC

TCTTGCCTCAGCCTCCTGAGTAGCTGGGATTACAGGCACCCATCACCATGTCCAGCTAATTTTTGTATTTTTAGTA

GAGACAGGGTTTTCCCATGTTGGCCAGGCTGGTCTCGATCTCCTGACCTCAAATGATCGGCCCACCTCGGCCTCCC

AAAGTGCTGGGATGACAGTTGTGAGCCACCACACTCAGCCTGCTCTTTCTAATATTTGAAACTTGTTAGACAATTT

GCTACCCATCTAATGTGATATTTTAGGAATCCAATATGCATGGTTTATTATTTCTTAAAAAAAATATTCTTTTACC

TGTCACCTGAATTTAGTAATGCCTTTTATGTTACACAACTTAGCACTTTCCAGAAACAAAAACTCTCTCCTTGAAA

TAATAGAGTTTTTATCTACCAAAGATATGCTAGTGTCTCATTTCAAAGGCTGCTTTTTCCAGCTTACATTTTATAT

ACTTACTCACTTGAAGTTTCTAAATATTCTTGTAATTTTAAAACTATCTCAGATTTACTGAGGTTTATCTTCTGGT

GGTAGATTATCCATAAGAAGAGTGATGTGCCAGAATCACTCTGGGATCCTTGTCTGACAAGATTCAAAGGACTAAA

TTTAATTCAGTCATGAACACTGCCAATTACCGTTTATGGGTAGACATCTTTGGAAATTTCCACAAGGTCAGACATT

CGCAACTATCCCTTCTACATGTCCACACGTATACTCCAACACTTTATTAGGCATCTGATTAGTTTGGAAAGTATGC

FIG. 4B

CTCCATCTGAATTAGTCCAGTGTGGCTTAGAGTTGGTACAACATTCTCACAGAATTTCCTAATTTTGTAGGTTCAG
CCTGATAACCACTGGAGTTCTTTGGTCCTCATTAAATAGCTTTCTTCACACATTGCTCTGCCTGTTACACATATGA
TGAACACTGCTTTTTAGACTTCATTAGGAATTTAGGACTGCATCTTGACAACTGAGCCTATTCTACTATATGTACA
ATACCTAGCCCATAATAGGTATACAATACACATTTGGTAAAACTAATTTTCAACCAATGACATGTATTTTTCAACT
AGTAACCTAGAAATGTTTCACTTAAAATCTGAGAACTGGTTACACTACAAGTTACCTTGGAGATTCATATATGAAA
ACGCAAACTTAGCTATTTGATTGTATTCACTGGGACTTAAGAATGCGCCTGAATAATTGTGAGTTCGATTTGTTCT
GGCAGGCTAATGACCATTTCCAGTAAAGTGAATAGAGGTCAGAAGTCGTATAAAAGAGGTGTTGTCAGAACACCGT
TGAGATTACATAGGTGAACAACTATTTTTAAGCAACTTTATTTGTGTAGTGACAAAGCATCCCAATGCAGGCTGAA
ATGTTTCATCACATCTCTGGATCTCTCTATTTTGTGCAGACATTGAAAAAATTGTTCATATTATTTCCATGTTATC
AGAATATTTGATTTTTTAAAAACATAGGCCAAGTTCATTCACTTCATTATTCATTTATCAAAATCAGAGTGAATCA
CATTAGTCGCCTTCACAACTGATAAAGATCACTGAAGTCAAATTGATTTTTGCTATAATCTTCAATCTACCTATAT
TTAATTGAGAATCTAAAATGTACAAATCATTGTGTTGATTCTGCAGTGATCCTGCTATAAGTAAGACTCAGTCCCT
GATTTTAGGTATCCTGTGAAAAGCAGAATTAAGACAAATACACAAGAGACAAAGCACAAAAAATAAATATCATAAG
GGGATGAACAAAATGGTGGAGAAAGAGTAGACAAAGTTTTTGATCACCTGCCTTCAAAGAAAGGCTGTGAATTTTG
TTCACTTAGACAGCTTGGAGACAAGAAATTACCCAAAAGTAAGGTGAGGAGGATAGGCAAAAAGAGCAGAAAGATG
TGAATGGACATTGTTGAGAAATGTGATAGGAAAACAATCATAGATAAAGGATTTCCAAGCAACAGAGCATATCCAG
ATGAGGTAGGATGGGATAAACTCTTATTGAACCAATCTTCACCAATTTTGTTTTT<u>CTTTT</u>GCAGAGCAAGCTAGGA
ATTGTTTCCCTTCTACTGGGCACAATACACGCATTGATTTTTGCCTGGAATAAGTGGATAGATATAAAACAATTTG
TATGGTATACACCTCCAACTTTTATGATAGCTGTTTTCCTTCCAATTGTTGTCCTGATATTTAAAAGCATACTATT
CCTGCCATGCTTGAGGAAGAAGATACTGAAGATTAGACATGGTTGGGAAGACGTCACCAAAATTAACAAAACTGAG
ATATGTTCCCAGTT<u>GTAG</u>AATTACTGTTTACACACATTTTTGTTCAATATTGATATATTTTATCACCAACATTTCA
AGTTTGTATTTGTTAATAAAATGATTATTCAAGGAAAAAAAAAAAAAAAAAAAA   SEQ ID NO: 4

FIG. 5
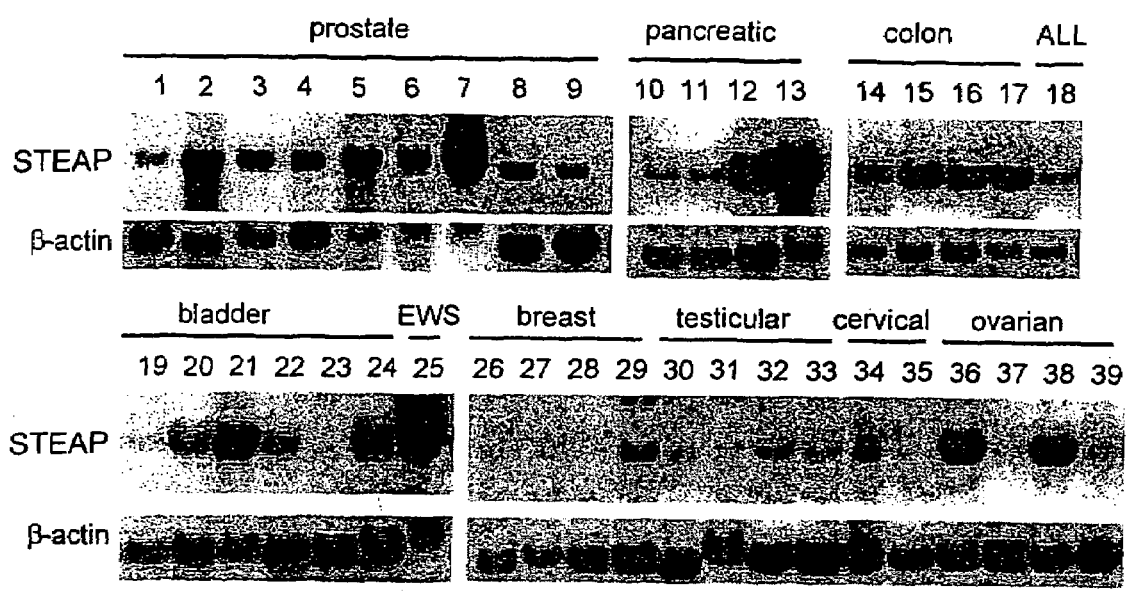
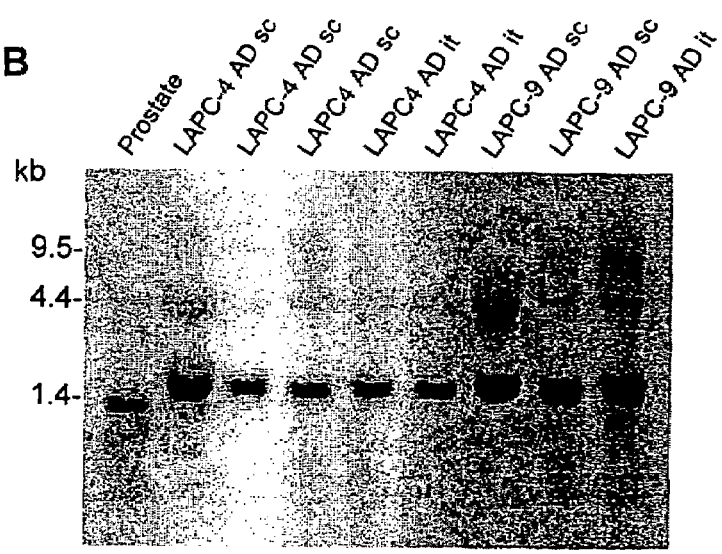

FIG. 7
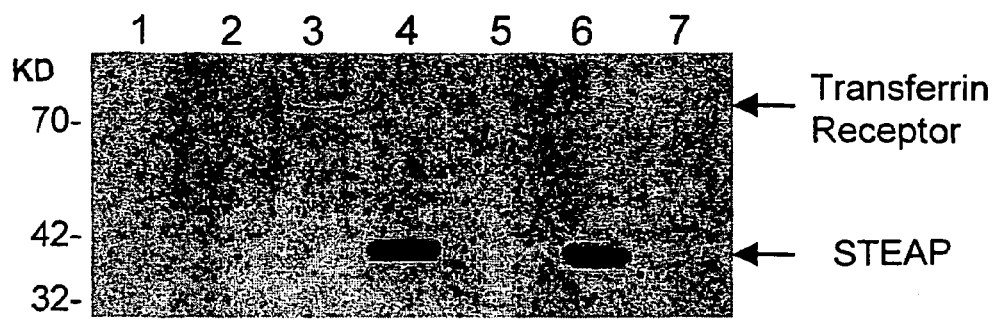
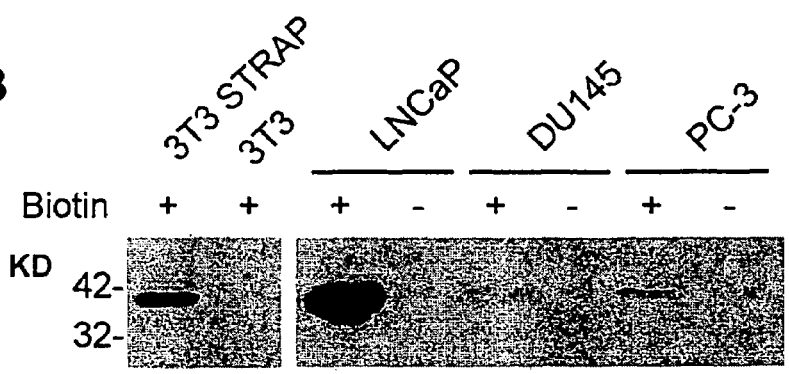
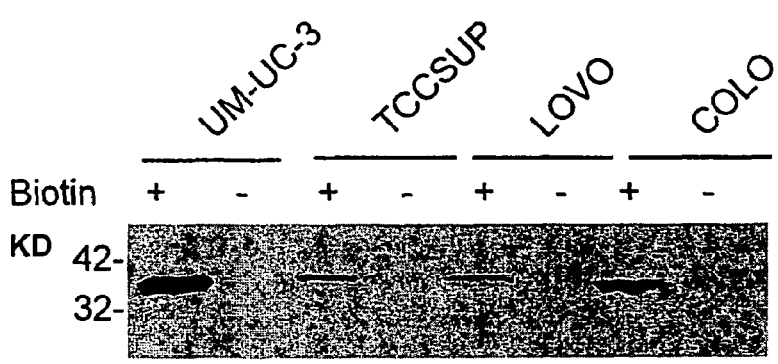

FIG. 9A

```
          10            19            28            37            46            55
5' GGA CGC GTG GGC GGA CGC GTG GGT TCC TCG GGC CCT CGG CGC CAC AAG CTG TCC
          64            73            82            91           100           109
   GGG CAC GCA GCC CCT AGC GGC GCG TCG CTG CCA AGC CGG CCT CCG CGC GCC TCC
         118           127           136           145           154           163
   CTC CTT CCT TCT CCC CTG GCT GTT CGC GAT CCA GCT TGG GTA GGC GGG GAA GCA
         172           181           190           199           208           217
   GCT GGA GTG CGA CCG CCA CGG CAG CCA CCC TGC AAC CGC CAG TCG GAG GTG CAG
         226           235           244           253           262           271
   TCC GTA GGC CCT GGC CCC CGG GTG GGC CCT TGG GGA GTC GGC GCC GCT CCC GAG
         280           289           298           307           316           325
   GAG CTG CAA GGC TCG CCC CTG CCC GGC GTG GAG GGC GCG GGG GGC GCG GAG GAT
         334           343           352           361           370           379
   ATT CTT GGT GAT CTT GGA AGT GTC CGT ATC ATG GAA TCA ATC TCT ATG ATG GGA
                                                 M   E   S   I   S   M   G
         388           397           406           415           424           433
   AGC CCT AAG AGC CTT AGT GAA ACT TGT TTA CCT AAT GGC ATA AAT GGT ATC AAA
    S   P   K   S   L   S   E   T   C   L   P   N   G   I   N   G   I   K 442           451           460           469           478           487
   GAT GCA AGG AAG GTC ACT GTA GGT GTG ATT GGA AGT GGA GAT TTT GCC AAA TCC
    D   A   R   K   V   T   V   G   V   I   G   S   G   D   F   A   K   S
         496           505           514           523           532           541
   TTG ACC ATT CGA CTT ATT AGA TGC GGC TAT CAT GTG GTC ATA GGA AGT AGA AAT
    L   T   I   R   L   I   R   C   G   Y   H   V   V   I   G   S   R   N
         550           559           568           577           586           595
   CCT AAG TTT GCT TCT GAA TTT TTT CCT CAT GTG GTA GAT GTC ACT CAT CAT GAA
    P   K   F   A   S   E   F   F   P   H   V   V   D   V   T   H   H   E
         604           613           622           631           640           649
   GAT GCT CTC ACA AAA ACA AAT ATA ATA TTT GTT GCT ATA CAC AGA GAA CAT TAT
    D   A   L   T   K   T   N   I   I   F   V   A   I   H   R   E   H   Y
         658           667           676           685           694           703
   ACC TCC CTG TGG GAC CTG AGA CAT CTG CTT GTG GGT AAA ATC CTG ATT GAT GTG
    T   S   L   W   D   L   R   H   L   L   V   G   K   I   L   I   D   V
         712           721           730           739           748           757
   AGC AAT AAC ATG AGG ATA AAG CAG TAC CCA GAA TCC AAT GCT GAA TAT TTG GCT
    S   N   N   M   R   I   K   Q   Y   P   E   S   N   A   E   Y   L   A
```

FIG. 9B

```
      766         775         784         793         802         811
TCA TTA TTC CCA GAT TCT TTG ATT GTC AAA GGA TTT AAT GTT GTC TCA GCT TGG
--- --- --- --- --- --- --- --- --- --- --- --- --- --- --- --- --- ---
 S   L   F   P   D   S   L   I   V   K   G   F   N   V   V   S   A   W 820         829         838         847         856         865
GCA CTT CAG TTA GGA CCT AAG GAT GCC AGC CGG CAG GTT TAT ATA TGC AGC AAC
--- --- --- --- --- --- --- --- --- --- --- --- --- --- --- --- --- ---
 A   L   Q   L   G   P   K   D   A   S   R   Q   V   Y   I   C   S   N 874         883         892         901         910         919
AAT ATT CAA GCG CGA CAA CAG GTT ATT GAA CTT GCC CGC CAG TTG AAT TTC ATT
--- --- --- --- --- --- --- --- --- --- --- --- --- --- --- --- --- ---
 N   I   Q   A   R   Q   Q   V   I   E   L   A   R   Q   L   N   F   I 928         937         946         955         964         973
CCC ATT GAC TTG GGA TCC TTA TCA TCA GCC AGA GAG ATT GAA AAT TTA CCC CTA
--- --- --- --- --- --- --- --- --- --- --- --- --- --- --- --- --- ---
 P   I   D   L   G   S   L   S   S   A   R   E   I   E   N   L   P   L 982         991        1000        1009        1018        1027
CGA CTC TTT ACT CTC TGG AGA GGG CCA GTG GTG GTA GCT ATA AGC TTG GCC ACA
--- --- --- --- --- --- --- --- --- --- --- --- --- --- --- --- --- ---
 R   L   F   T   L   W   R   G   P   V   V   V   A   I   S   L   A   T 1036        1045        1054        1063        1072        1081
TTT TTT TTC CTT TAT TCC TTT GTC AGA GAT GTG ATT CAT CCA TAT GCT AGA AAC
--- --- --- --- --- --- --- --- --- --- --- --- --- --- --- --- --- ---
 F   F   F   L   Y   S   F   V   R   D   V   I   H   P   Y   A   R   N 1090        1099        1108        1117        1126        1135
CAA CAG AGT GAC TTT TAC AAA ATT CCT ATA GAG ATT GTG AAT AAA ACC TTA CCT
--- --- --- --- --- --- --- --- --- --- --- --- --- --- --- --- --- ---
 Q   Q   S   D   F   Y   K   I   P   I   E   I   V   N   K   T   L   P 1144        1153        1162        1171        1180        1189
ATA GTT GCC ATT ACT TTG CTC TCC CTA GTA TAC CTT GCA GGT CTT CTG GCA GCT
--- --- --- --- --- --- --- --- --- --- --- --- --- --- --- --- --- ---
 I   V   A   I   T   L   L   S   L   V   Y   L   A   G   L   L   A   A 1198        1207        1216        1225        1234        1243
GCT TAT CAA CTT TAT TAC GGC ACC AAG TAT AGG AGA TTT CCA CCT TGG TTG GAA
--- --- --- --- --- --- --- --- --- --- --- --- --- --- --- --- --- ---
 A   Y   Q   L   Y   Y   G   T   K   Y   R   R   F   P   P   W   L   E 1252        1261        1270        1279        1288        1297
ACC TGG TTA CAG TGT AGA AAA CAG CTT GGA TTA CTA AGT TTT TTC TTC GCT ATG
--- --- --- --- --- --- --- --- --- --- --- --- --- --- --- --- --- ---
 T   W   L   Q   C   R   K   Q   L   G   L   L   S   F   F   F   A   M 1306        1315        1324        1333        1342        1351
GTC CAT GTT GCC TAC AGC CTC TGC TTA CCG ATG AGA AGG TCA GAG AGA TAT TTG
--- --- --- --- --- --- --- --- --- --- --- --- --- --- --- --- --- ---
 V   H   V   A   Y   S   L   C   L   P   M   R   R   S   E   R   Y   L 1360        1369        1378        1387        1396        1405
TTT CTC AAC ATG GCT TAT CAG CAG GTT CAT GCA AAT ATT GAA AAC TCT TGG AAT
--- --- --- --- --- --- --- --- --- --- --- --- --- --- --- --- --- ---
 F   L   N   M   A   Y   Q   Q   V   H   A   N   I   E   N   S   W   N
```

FIG. 9C

```
         1414        1423        1432        1441        1450        1459
GAG GAA GAA GTT TGG AGA ATT GAA ATG TAT ATC TCC TTT GGC ATA ATG AGC CTT
--- --- --- --- --- --- --- --- --- --- --- --- --- --- --- --- --- ---
 E   E   E   V   W   R   I   E   M   Y   I   S   F   G   I   M   S   L 1468        1477        1486        1495        1504        1513
GGC TTA CTT TCC CTC CTG GCA GTC ACT TCT ATC CCT TCA GTG AGC AAT GCT TTA
--- --- --- --- --- --- --- --- --- --- --- --- --- --- --- --- --- ---
 G   L   L   S   L   L   A   V   T   S   I   P   S   V   S   N   A   L 1522        1531        1540        1549        1558        1567
AAC TGG AGA GAA TTC AGT TTT ATT CAG TCT ACA CTT GGA TAT GTC GCT CTG CTC
--- --- --- --- --- --- --- --- --- --- --- --- --- --- --- --- --- ---
 N   W   R   E   F   S   F   I   Q   S   T   L   G   Y   V   A   L   L 1576        1585        1594        1603        1612        1621
ATA AGT ACT TTC CAT GTT TTA ATT TAT GGA TGG AAA CGA GCT TTT GAG GAA GAG
--- --- --- --- --- --- --- --- --- --- --- --- --- --- --- --- --- ---
 I   S   T   F   H   V   L   I   Y   G   W   K   R   A   F   E   E   E 1630        1639        1648        1657        1666        1675
TAC TAC AGA TTT TAT ACA CCA CCA AAC TTT GTT CTT GCT CTT GTT TTG CCC TCA
--- --- --- --- --- --- --- --- --- --- --- --- --- --- --- --- --- ---
 Y   Y   R   F   Y   T   P   P   N   F   V   L   A   L   V   L   P   S 1684        1693        1702        1711        1720        1729
ATT GTA ATT CTG GAT CTT TTG CAG CTT TGC AGA TAC CCA GAC TGA GCT GGA ACT
--- --- --- --- --- --- --- --- --- --- --- --- --- --- --- --- --- ---
 I   V   I   L   D   L   L   Q   L   C   R   Y   P   D   *

1738        1747        1756        1765        1774        1783
GGA ATT TGT CTT CCT ATT GAC TCT ACT TCT TTA AAA GCG GCT GCC CAT TAC ATT
--- --- --- --- --- --- --- --- --- --- --- --- --- --- --- --- --- ---
         1792        1801        1810        1819        1828        1837
CCT CAG CTG TCC TTG CAG TTA GGT GTA CAT GTG ACT GAG TGT TGG CCA GTG AGA
--- --- --- --- --- --- --- --- --- --- --- --- --- --- --- --- --- ---
         1846        1855        1864        1873        1882        1891
TGA AGT CTC CTC AAA GGA AGG CAG CAT GTG TCC TTT TTC ATC CCT TCA TCT TGC
--- --- --- --- --- --- --- --- --- --- --- --- --- --- --- --- --- ---
         1900        1909        1918        1927        1936        1945
TGC TGG GAT TGT GGA TAT AAC AGG AGC CCT GGC AGC TGT CTC CAG AGG ATC AAA
--- --- --- --- --- --- --- --- --- --- --- --- --- --- --- --- --- ---
         1954        1963        1972        1981        1990        1999
GCC ACA CCC AAA GAG TAA GGC AGA TTA GAG ACC AGA AAG ACC TTG ACT ACT TCC
--- --- --- --- --- --- --- --- --- --- --- --- --- --- --- --- --- ---
         2008        2017        2026        2035        2044        2053
CTA CTT CCA CTG CTT TTC CTG CAT TTA AGC CAT TGT AAA TCT GGG TGT GTT ACA
--- --- --- --- --- --- --- --- --- --- --- --- --- --- --- --- --- ---
         2062        2071        2080        2089        2098        2107
TGA AGT GAA AAT TAA TTC TTT CTG CCC TTC AGT TCT TTA TCC TGA TAC CAT TTA
--- --- --- --- --- --- --- --- --- --- --- --- --- --- --- --- --- ---
         2116        2125        2134        2143        2152        2161
ACA CTG TCT GAA TTA ACT AGA CTG CAA TAA TTC TTT CTT TTG AAA GCT TTT AAA
--- --- --- --- --- --- --- --- --- --- --- --- --- --- --- --- --- ---
```

FIG. 9D

```
        2170            2179            2188            2197            2206            2215
GGA TAA TGT GCA ATT CAC ATT AAA ATT GAT TTT CCA TTG TCA ATT AGT TAT ACT
--- --- --- --- --- --- --- --- --- --- --- --- --- --- --- --- --- ---
        2224            2233            2242            2251            2260            2269
CAT TTT CCT GCC TTG ATC TTT CAT TAG ATA TTT TGT ATC TGC TTG GAA TAT ATT
--- --- --- --- --- --- --- --- --- --- --- --- --- --- --- --- --- ---
        2278            2287            2296            2305            2314            2323
ATC TTC TTT TTA ACT GTG TAA TTG GTA ATT ACT AAA ACT CTG TAA TCT CCA AAA
--- --- --- --- --- --- --- --- --- --- --- --- --- --- --- --- --- ---
        2332            2341            2350            2359            2368            2377
TAT TGC TAT CAA ATT ACA CAC CAT GTT TTC TAT CAT TCT CAT AGA TCT GCC TTA
--- --- --- --- --- --- --- --- --- --- --- --- --- --- --- --- --- ---
        2386            2395            2404            2413            2422            2431
TAA ACA TTT AAA TAA AAA GTA CTA TTT AAT GAT TTA AAA AAA AAA AAA AAA AAA
--- --- --- --- --- --- --- --- --- --- --- --- --- --- --- --- --- ---
        2440            2449
AAA AAA AAA AAA AAA AAA AAA AA 3'  SEQ ID NO:5
--- --- --- --- --- --- --- --      SEQ ID NO:6
```

FIG. 10A

```
  1 CGAAACTTCC CTCTACCCGC CCGGCCCGCG GCGCGCACCG TTGGCGCTGG ACGCTTCCTC
    GCTTTGAAGG GAGATGGGCG GGCCGGGCGC CGCGCGTGGC AACCGCGACC TGCGAAGGAG

M  E   K  T  C  I   D  A  L   P  L  T
 61 CTTGGAAGCG CCTCTCCCTC AGTTATGGAG AAAACTTGTA TAGATGCACT TCCTCTTACT
    GAACCTTCGC GGAGAGGGAG TCAATACCTC TTTTGAACAT ATCTACGTGA AGGAGAATGA

M  N  S  S   E  K  Q   E  T  V   C  I  F   G  T  G  D   F  G  R
121 ATGAATTCTT CAGAAAAGCA AGAGACTGTA TGTATTTTTG GAACTGGTGA TTTTGGAAGA
    TACTTAAGAA GTCTTTTCGT TCTCTGACAT ACATAAAAAC CTTGACCACT AAAACCTTCT

S  L  G  L   K  M  L   Q  C  G   Y  S  V   V  F  G  S   R  N  P
181 TCACTGGGAT TGAAAATGCT CCAGTGTGGT TATTCTGTTG TTTTTGGAAG TCGAAACCCC
    AGTGACCCTA ACTTTTACGA GGTCACACCA ATAAGACAAC AAAAACCTTC AGCTTTGGGG

Q  K  T  T   L  L  P   S  G  A   E  V  L   S  Y  S  E   A  A  K
241 CAGAAGACCA CCCTACTGCC CAGTGGTGCA GAAGTCTTGA GCTATTCAGA AGCAGCCAAG
    GTCTTCTGGT GGGATGACGG GTCACCACGT CTTCAGAACT CGATAAGTCT TCGTCGGTTC

K  S  G  I   I  I     A  I  H   R  E  H   Y  D  F  L   T  E  L
301 AAGTCTGGCA TCATAATCAT AGCAATCCAC AGAGAGCATT ATGATTTTCT CACAGAATTA
    TTCAGACCGT AGTATTAGTA TCGTTAGGTG TCTCTCGTAA TACTAAAAGA GTGTCTTAAT

T  E  V  L   N  G  K   I  L  V   D  I  S   N  N  L  K   I  N  Q
361 ACTGAGGTTC TCAATGGAAA AATATTGGTA GACATCAGCA ACAACCTCAA AATCAATCAA
    TGACTCCAAG AGTTACCTTT TTATAACCAT CTGTAGTCGT TGTTGGAGTT TTAGTTAGTT

Y  P  E  S   N  A  E   Y  L  A   H  L  V   P  G  A  H   V  V  K
421 TATCCAGAAT CTAATGCAGA GTACCTTGCT CATTTGGTGC CAGGAGCCCA CGTGGTAAAA
    ATAGGTCTTA GATTACGTCT CATGGAACGA GTAAACCACG GTCCTCGGGT GCACCATTTT

A  F  N  T   I  S  A   W  A  L   Q  S  G   A  L  D  A   S  R  Q
481 GCATTTAACA CCATCTCAGC CTGGGCTCTC CAGTCAGGAG CACTGGATGC AAGTCGGCAG
    CGTAAATTGT GGTAGAGTCG GACCCGAGAG GTCAGTCCTC GTGACCTACG TTCAGCCGTC

V  F  V  C   G  N  D   S  K  A   K  Q  R  V   M  D  I   V  R  N
541 GTGTTTGTGT GTGGAAATGA CAGCAAAGCC AAGCAAAGAG TGATGGATAT TGTTCGTAAT
    CACAAACACA CACCTTTACT GTCGTTTCGG TTCGTTTCTC ACTACCTATA ACAAGCATTA

L  G  L  T   P  M  D   Q  G  S   L  M  A  A   K  E  I   E  K  Y
601 CTTGGACTTA CTCCAATGGA TCAAGGATCA CTCATGGCAG CCAAAGAAAT TGAAAAGTAC
    GAACCTGAAT GAGGTTACCT AGTTCCTAGT GAGTACCGTC GGTTTCTTTA ACTTTTCATG

P  L  Q  L   F  P  M   W  R  F   P  F  Y  L   S  A  V   L  C  V
661 CCCCTGCAGC TATTTCCAAT GTGGAGGTTC CCCTTCTATT TGTCTGCTGT GCTGTGTGTC
    GGGGACGTCG ATAAAGGTTA CACCTCCAAG GGGAAGATAA ACAGACGACA CGACACACAG

F  L  F  F   Y  C  V   I  R  D   V  I  Y  P   Y  V  Y   E  K  K
721 TTCTTGTTTT TCTATTGTGT TATAAGAGAC GTAATCTACC CTTATGTTTA TGAAAAGAAA
    AAGAACAAAA AGATAACACA ATATTCTCTG CATTAGATGG GAATACAAAT ACTTTTCTTT
```

FIG. 10B

```
        D  N  T  F     R  M  A     I  S  I     P  N  R  I     F  P  I     T  A  L
 781   GATAATACAT TTCGTATGGC TATTTCCATT CCAAATCGTA TCTTTCCAAT AACAGCACTT
       CTATTATGTA AAGCATACCG ATAAAGGTAA GGTTTAGCAT AGAAAGGTTA TTGTCGTGAA

T  L  L  A     L  V  Y     L  P  G     V  I  A  A     I  L  Q     L  Y  R
 841   ACACTGCTTG CTTTGGTTTA CCTCCCTGGT GTTATTGCTG CCATTCTACA ACTGTACCGA
       TGTGACGAAC GAAACCAAAT GGAGGGACCA CAATAACGAC GGTAAGATGT TGACATGGCT

G  T  K  Y     R  R  F     P  D  W     L  D  H  W     M  L  C     R  K  Q
 901   GGCACAAAAT ACCGTCGATT CCCAGACTGG CTTGACCACT GGATGCTTTG CCGAAAGCAG
       CCGTGTTTTA TGGCAGCTAA GGGTCTGACC GAACTGGTGA CCTACGAAAC GGCTTTCGTC

L  G  L  V     A  L  G     F  A  F     L  H  V  L     Y  T  L     V  I  P
 961   CTTGGCTTGG TAGCTCTGGG ATTTGCCTTC CTTCATGTCC TCTACACACT TGTGATTCCT
       GAACCGAACC ATCGAGACCC TAAACGGAAG GAAGTACAGG AGATGTGTGA ACACTAAGGA

I  R  Y  Y     V  R  W     R  L  G     N  L  T  V     T  Q  A     I  L  K
1021   ATTCGATATT ATGTACGATG GAGATTGGGA AACTTAACCG TTACCCAGGC AATACTCAAG
       TAAGCTATAA TACATGCTAC CTCTAACCCT TTGAATTGGC AATGGGTCCG TTATGAGTTC

K  E  N  P     F  S  T     S  S  A     W  L  S  D     S  Y  V     A  L  G
1081   AAGGAGAATC CATTTAGCAC CTCCTCAGCC TGGCTCAGTG ATTCATATGT GGCTTTGGGA
       TTCCTCTTAG GTAAATCGTG GAGGAGTCGG ACCGAGTCAC TAAGTATACA CCGAAACCCT

I  L  G  F     F  L  F     V  L  L     G  I  T  S     L  P  S     V  S  N
1141   ATACTTGGGT TTTTTCTGTT TGTACTCTTG GGAATCACTT CTTTGCCATC TGTTAGCAAT
       TATGAACCCA AAAAAGACAA ACATGAGAAC CCTTAGTGAA GAAACGGTAG ACAATCGTTA

A  V  N  W     R  E  F     R  F  V     Q  S  K  L     G  Y  L     T  L  I
1201   GCAGTCAACT GGAGAGAGTT CCGATTTGTC CAGTCCAAAC TGGGTTATTT GACCCTGATC
       CGTCAGTTGA CCTCTCTCAA GGCTAAACAG GTCAGGTTTG ACCCAATAAA CTGGGACTAG

L  C  T  A     H  T  L     V  Y  G     G  K  R  F     L  S  P     S  N  L
1261   TTGTGTACAG CCCACACCCT GGTGTACGGT GGGAAGAGAT TCCTCAGCCC TTCAAATCTC
       AACACATGTC GGGTGTGGGA CCACATGCCA CCCTTCTCTA AGGAGTCGGG AAGTTTAGAG

R  W  Y  L     P  A  A     Y  V  L     G  L  I  I     P  C  T     V  L  V
1321   AGATGGTATC TTCCTGCAGC CTACGTGTTA GGGCTTATCA TTCCTTGCAC TGTGCTGGTG
       TCTACCATAG AAGGACGTCG GATGCACAAT CCCGAATAGT AAGGAACGTG ACACGACCAC

I  K  F  V     L  I  M     P  C  V     D  N  T  L     T  R  I     R  Q  G
1381   ATCAAGTTTG TCCTAATCAT GCCATGTGTA GACAACACCC TTACAAGGAT CCGCCAGGGC
       TAGTTCAAAC AGGATTAGTA CGGTACACAT CTGTTGTGGG AATGTTCCTA GGCGGTCCCG

W  E  R  N     S  K  H
1441   TGGGAAAGGA ACTCAAAACA CTAGAAAAG CATTGAATGG AAAATCAATA TTTAAAACAA
       ACCCTTTCCT TGAGTTTTGT GATCTTTTC GTAACTTACC TTTAGTTAT AAATTTTGTT
```

FIG. 10C

```
1501   AGTTCAATTT AGCTGGATTT CTGAACTATG GTTTTGAATG TTTAAAGAAG AATGATGGGT
       TCAAGTTAAA TCGACCTAAA GACTTGATAC CAAAACTTAC AAATTTCTTC TTACTACCCA

1561   ACAGTTAGGA AAGTTTTTTT CTTACACCGT GACTGAGGGA AACATTGCTT GTCTTTGAGA
       TGTCAATCCT TTCAAAAAAA GAATGTGGCA CTGACTCCCT TTGTAACGAA CAGAAACTCT

1621   AATTGACTGA CATACTGGAA GAGAACACCA TTTTATCTCA GGTTAGTGAA GAATCAGTGC
       TTAACTGACT GTATGACCTT CTCTTGTGGT AAAATAGAGT CCAATCACTT CTTAGTCACG

1681   AGGTCCCTGA CTCTTATTTT CCCAGAGGCC ATGGAGCTGA GATTGAGACT AGCCTTGTGG
       TCCAGGGACT GAGAATAAAA GGGTCTCCGG TACCTCGACT CTAACTCTGA TCGGAACACC

1741   TTTCACACTA AAGAGTTTCC TTGTTATGGG CAACATGCAT GACCTAATGT CTTGCAAAAT
       AAAGTGTGAT TTCTCAAAGG AACAATACCC GTTGTACGTA CTGGATTACA GAACGTTTTA

1801   CCAATAGAAG TATTGCAGCT TCCTTCTCTG GCTCAAGGGC TGAGTTAAGT GAAAGGAAAA
       GGTTATCTTC ATAACGTCGA AGGAAGAGAC CGAGTTCCCG ACTCAATTCA CTTTCCTTTT

1861   ACAGCACAAT GGTGACCACT GATAAAGGCT TTATTAGGTA TATCTGAGGA AGTGGGTCAC
       TGTCGTGTTA CCACTGGTGA CTATTTCCGA AATAATCCAT ATAGACTCCT TCACCCAGTG

1921   ATGAAATGTA AAAAGGGAAT GAGGTTTTTG TTGTTTTTTG GAAGTAAAGG CAAACATAAA
       TACTTTACAT TTTTCCCTTA CTCCAAAAAC AACAAAAAAC CTTCATTTCC GTTTGTATTT

1981   TATTACCATG ATGAATTCTA GTGAAATGAC CCCTTGACTT TGCTTTTCTT AATACAGATA
       ATAATGGTAC TACTTAAGAT CACTTTACTG GGAACTGAA ACGAAAAGAA TTATGTCTAT

2041   TTTACTGAGA GGAACTATTT TTATAACACA AGAAAAATTT ACAATTGATT AAAAGTATCC
       AAATGACTCT CCTTGATAAA AATATTGTGT TCTTTTTAAA TGTTAACTAA TTTTCATAGG

2101   ATGTCTTGGA TACATACGTA TCTATAGAGC TGGCATGTAA TTCTTCCTCT ATAAAGAATA
       TACAGAACCT ATGTATGCAT AGATATCTCG ACCGTACATT AAGAAGGAGA TATTTCTTAT

2161   GGTATAGGAA AGACTGAATA AAAATGGAGG GATATCCCCT TGGATTTCAC TTGCATTGTG
       CCATATCCTT TCTGACTTAT TTTTACCTCC CTATAGGGGA ACCTAAAGTG AACGTAACAC

2221   CAATAAGCAA AGAAGGGTTG ATAAAAGTTC TTGATCAAAA AGTTCAAAGA AACCAGAATT
       GTTATTCGTT TCTTCCCAAC TATTTTCAAG AACTAGTTTT TCAAGTTTCT TTGGTCTTAA

2281   TTAGACAGCA AGCTAAATAA ATATTGTAAA ATTGCACTAT ATTAGGTTAA GTATTATTTA
       AATCTGTCGT TCGATTTATT TATAACATTT TAACGTGATA TAATCCAATT CATAATAAAT

2341   GGTATTATAA TATGCTTTGT AAATTTTATA TTCCAAATAT TGCTCAATAT TTTTCATCTA
       CCATAATATT ATACGAAACA TTTAAAATAT AAGGTTTATA ACGAGTTATA AAAAGTAGAT

2401   TTAAATTAAT TTCTAGTGTA AATAAGTAGC TTCTATATCT GTCTTAGTCT ATTATAATTG
       AATTTAATTA AAGATCACAT TTATTCATCG AAGATATAGA CAGAATCAGA TAATATTAAC
```

FIG. 10D

```
2461  TAAGGAGTAA AATTAAATGA ATAGTCTGCA GGTATAAATT TGAACAATGC ATAGATGATC
      ATTCCTCATT TTAATTTACT TATCAGACGT CCATATTTAA ACTTGTTACG TATCTACTAG

2521  GAAAATTACG GAAAATCATA GGGCAGAGAG GTGTGAAGAT TCATCATTAT GTGAAATTTG
      CTTTTAATGC CTTTTAGTAT CCCGTCTCTC CACACTTCTA AGTAGTAATA CACTTTAAAC

2581  GATCTTTCTC AAATCCTTGC TGAAATTTAG GATGGTTCTC ACTGTTTTC TGTGCTGATA
      CTAGAAAGAG TTTAGGAACG ACTTTAAATC CTACCAAGAG TGACAAAAAG ACACGACTAT

2641  GTACCCTTTC CAAGGTGACC TTCAGGGGGA TTAACCTTCC TAGCTCAAGC AATGAGCTAA
      CATGGGAAAG GTTCCACTGG AAGTCCCCCT AATTGGAAGG ATCGAGTTCG TTACTCGATT

2701  AAGGAGCCTT ATGCATGATC TTCCCACATA TCAAAATAAC TAAAAGGCAC TGAGTTTGGC
      TTCCTCGGAA TACGTACTAG AAGGGTGTAT AGTTTTATTG ATTTTCCGTG ACTCAAACCG

2761  ATTTTTCTGC CTGCTCTGCT AAGACCTTTT TTTTTTTTTT ACTTTCATTA TAACATATTA
      TAAAAGACG GACGAGACGA TTCTGGAAAA AAAAAAAAAA TGAAAGTAAT ATTGTATAAT

2821  TACATGACAT TATACAAAAA TGATTAAAAT ATATTAAAAC AACATCAACA ATCCAGGATA
      ATGTACTGTA ATATGTTTTT ACTAATTTTA TATAATTTTG TTGTAGTTGT TAGGTCCTAT

2881  TTTTTCTATA AAACTTTTTA AAAATAATTG TATCTATATA TTCAATTTTA CATCCTTTTT
      AAAAAGATAT TTTGAAAAAT TTTTATTAAC ATAGATATAT AAGTTAAAAT GTAGGAAAAA

2941  CAAAGGCTTT GTTTTTCTAA AGGCTTTGTT TTCCTTTTTA TTATTTTTTT CTTTTTTATT
      GTTTCCGAAA CAAAAAGATT TCCGAAACAA AAGGAAAAAT AATAAAAAAA GAAAAAATAA

3001  TTTTTGAGAC AGTCTTGCTC TGTCGCTCAG GCTGGAGTGC AGTGGCACGA TCTCAGCTCA
      AAAAACTCTG TCAGAACGAG ACAGCGAGTC CGACCTCACG TCACCGTGCT AGAGTCGAGT

3061  CTGCAACCTC CTCCTCCCAG GTTCAAGTGA TTCTTGTTCA TCAGCCTCCC GAGTAGCTGG
      GACGTTGGAG GAGGAGGGTC CAAGTTCACT AAGAACAAGT AGTCGGAGGG CTCATCGACC

3121  GACTACAGGC ATGTGCCACT ATGCCCAGCT AATTTTTGTA CTTTTAGTAG AGACAGGGTT
      CTGATGTCCG TACACGGTGA TACGGGTCGA TTAAAAACAT GAAAATCATC TCTGTCCCAA

3181  TCACCACATT GGTCAGGCTG GTCTTGAAAT GCTGGCGTCA AGTGATCTGC CTGCCTCCGC
      AGTGGTGTAA CCAGTCCGAC CAGAACTTTA CGACCGCAGT TCACTAGACG GACGGAGGCG

3241  CTTACGTAAT ATATTTCTT AATGGCTGCA TAATATCACA TCAAATAGGC ATTTTTCAAA
      GAATGCATTA TATAAAGAA TTACCGACGT ATTATAGTGT AGTTTATCCG TAAAAAGTTT

3301  CCTCTTTCCT TATTAAACAT GTAGACTATA TCCATTTTTT ACTAAAATAA ATAACATTTC
      GGAGAAAGGA ATAATTTGTA CATCTGATAT AGGTAAAAAA TGATTTTATT TATTGTAAAG

3361  AGATAATATC TTTGCACTGA TAATGTTGCC AAGCCATTTC TAAAGTGACC TTATCAATTT
      TCTATTATAG AAACGTGACT ATTACAACGG TTCGGTAAAG ATTTCACTGG AATAGTTAAA
```

FIG. 10E

```
3421  AATTACCATT GGATGAGGGT GTTGCTTTCA TCGCACCATT GTAGATTGTC TTTTTTATTT
      TTAATGGTAA CCTACTCCCA CAACGAAAGT AGCGTGGTAA CATCTAACAG AAAAAATAAA

3481  CAATTTGCGT TTATTTATAA CTGGTTGCAA AGGTACACAG AACACACGCT CCTTCAACTT
      GTTAAACGCA AATAAATATT GACCAACGTT TCCATGTGTC TTGTGTGCGA GGAAGTTGAA

3541  ATCTTTGATA AACCCAAGCA AGGATACAAA AAGTTGGACG ACATTGAGTA GAGTCATGGT
      TAGAAACTAT TTGGGTTCGT TCCTATGTTT TTCAACCTGC TGTAACTCAT CTCAGTACCA

3601  ATACGGTGCT GACCCTACAG TATCAGTGGA AAAGATAAGG AAAATGTCAC TACTCACCTA
      TATGCCACGA CTGGGATGTC ATAGTCACCT TTTCTATTCC TTTTACAGTG ATGAGTGGAT

3661  TGTTATGCAA AACAGTTAGG TGTGCTGGGG CTGGATACTG CTCTTTTACT TGAGCATTGG
      ACAATACGTT TTGTCAATCC ACACGACCCC GACCTATGAC GAGAAAATGA ACTCGTAACC

3721  TTGATTAAAG TTTAGGTACC ATCCAGGCTG GTCTAGAGAA GTCTTTGGAG TTAACCATGC
      AACTAATTTC AAATCCATGG TAGGTCCGAC CAGATCTCTT CAGAAACCTC AATTGGTACG

3781  TCTTTTTGTT AAAGAAGAGA GTAATGTGTT TATCCTGGCT CATAGTCCGT CACCGAAAAT
      AGAAAAACAA TTTCTTCTCT CATTACACAA ATAGGACCGA GTATCAGGCA GTGGCTTTTA

3841  AGAAAATGCC ATCCATAGGT AAAATGCTGA CCTATAGAAA AAAATGAACT CTACTTTTAT
      TCTTTTACGG TAGGTATCCA TTTTACGACT GGATATCTTT TTTTACTTGA GATGAAAATA

3901  AGCCTAGTAA AAATGCTCTA CCTGAGTAGT TAAAAGCAAT TCATGAAGCC TGAAGCTAAA
      TCGGATCATT TTTACGAGAT GGACTCATCA ATTTTCGTTA AGTACTTCGG ACTTCGATTT

3961  GAGCACTCTG ATGGTTTTGG CATAATAGCT GCATTTCCAG ACCTGACCTT TGGCCCCAAC
      CTCGTGAGAC TACCAAAACC GTATTATCGA CGTAAAGGTC TGGACTGGAA ACCGGGGTTG

4021  CACAAGTGCT CCAAGCCCCA CCAGCTGACC AAAGAAAGCC CAAGTTCTCC TTCTGTCCTT
      GTGTTCACGA GGTTCGGGGT GGTCGACTGG TTTCTTTCGG GTTCAAGAGG AAGACAGGAA

4081  CCCACAACCT CCCTGCTCCC AAAACTATGA AATTAATTTG ACCATATTAA CACAGCTGAC
      GGGTGTTGGA GGGACGAGGG TTTTGATACT TTAATTAAAC TGGTATAATT GTGTCGACTG

4141  TCCTCCAGTT TACTTAAGGT AGAAAGAATG AGTTTACAAC AGATGAAAAT AAGTGCTTTG
      AGGAGGTCAA ATGAATTCCA TCTTTCTTAC TCAAATGTTG TCTACTTTTA TTCACGAAAC

4201  GGCGAACTGT ATTCCTTTTA ACAGATCCAA ACTATTTTAC ATTTAAAAAA AAAGTTAAAC
      CCGCTTGACA TAAGGAAAAT TGTCTAGGTT TGATAAAATG TAAATTTTTT TTTCAATTTG

4261  TAAACTTCTT TACTGCTGAT ATGTTTCCTG TATTCTAGAA AAATTTTTAC ACTTTCACAT
      ATTTGAAGAA ATGACGACTA TACAAAGGAC ATAAGATCTT TTTAAAAATG TGAAAGTGTA

4321  TATTTTTGTA CACTTTCCCC ATGTTAAGGG ATGATGGCTT TTATAAATGT GTATTCATTA
      ATAAAAACAT GTGAAAGGGG TACAATTCCC TACTACCGAA ATATTTACA CATAAGTAAT

4381  AATGTTACTT TAAAAATAAA AAAAAAAAAA AAAAAAAAAA AAAAAAAA    SEQ ID NO:7
      TTACAATGAA ATTTTTATTT TTTTTTTTTT TTTTTTTTTT TTTTTTTT    SEQ ID NO:8
```

FIG. 10F

STEAP-2, AA508880 (NCI_CGAP Pr6) SEQ ID NO:9
ggtcgactttcctttattcctttgtcagagatctgattcatccatatgctagaaaccaacagagtgacttttaca
aaattcctatagagattgtgaataaaaaccttacctatagttgccattactttgctctcccctagtataccttgcagg
tcttctggcagctgcttatcaactttattacggcaccaagtataggagatttccaccttggttggaaacctggtta
cagtgtagaaaacagcttggattactaagttgtttcttcgctatggtccatgttgcctacagcctctgcttaccga
tgagaaggtcagagagat STEAP-2, 98P4B6 SSH fragment SEQ ID NO:10
TTTGCAGCTTTGCAGATACCCAGACTGAGCTGGAACTGGAATTTGTCTTCCTATTGACTCTACTTCTTTAAAAGCG
GCTGCCCATTACATTCCTCAGCTGTCCTTGCAGTTAGGTGTACATGTGACTGAGTGTTGGCCAGTGAGATGAAGTC
TCCTCAAAGGAAGGCAGCATGTGTCCTTTTT STEAP-3, AI139607 (testis EST) SEQ ID NO:11
aagaaggagaatccatttagcacctcctcagcctggctcagtgattcatatgtggctttgggaatacttgggtttt
ttctgtttgtactcttgggaatcacttctttgccatctgttagcaatgcagtcaactggagagagttccgatttgt
ccagtccaaactgggttatttgaccctgatcttgtgtacagcccacaccctggtgtacggtgggaagagattcctc
agcccttcaaatctcagatggtatcttcctgcagcctacgtgttagggcttatcattccttgcactgtgctggtga
tcaagtttgtcctaatcatgccatgtgtagacaacacccttacaaggatccgccagggctgggaaaggaactcaaa
acactagaaaaagcattgaatggaaaatcaatatttaaaacaaagttcaatttagctggaaaaaaaaa STEAP 4, R80991 (placental EST) SEQ ID NO:12
ggccgcggcanccgctacgacctggtcaacctggcagtcaagcaggtcttggccanacaagagccacctctgggtg
aaggaggaggtctggcggatggagatctacctctccctgggagtgctggccctcggcacgttgtccctgctggccg
tgacctcactgccgtccattgcaaactcgctcaactggagggagttcagcttcgttcagtcctcactgggcttgt
ggccntcgtgctgagcacactncacacgctcacctacggctggacccgcgccttcgaggagagccgctacaagttc
tacctncctcccaccttcacgntcacgctgctggtgccctgcgttcgttcatcctgggccaaagccctgttntac
tgccttgcattcagccgnaga

```
STEAP-1    67  LPPQWHLPIKIAAIIASLTFLYTLLREVIHPLATSHQQYFYKIPILVINKVLPMVSITLL
STEAP-2   208  LFTLWRGPVVVAISLATFFFLYSFVRDVIHPYARNQQSDFYKIPIEIVNKTLPIVAITLL
               **  *   *   *   *  **  *  *  f*     * ****

STEAP-1   127  ALVYLPGVIAAIVQLHNGTKYKKFPHWLDKWMLTRKQFGLLSPPFAVLHAIYSLSYPMRR
STEAP-2   268  SLVYLAGLLAAAYQLYYGTKYRRFPPWLETWLQCRKQLGLLSFFFAMVHVAYSLCLPMRR
               **** *  **  ** ****  ** **    *   *** ********  *  ***  ****

STEAP-1   187  SYRYKLLNWAYQQVQQNKEDAWIEHDVWRMEIYVSLGIVGLAILALLAVTSIPSVSDSLT
STEAP-2   328  SERYLFLNMAYQQVHANIENSWNEEEVWRIEMYISFGIMSLGLLSLLAVTSIPSVSNALN
               * **  ** *****  *  *  * *  *** * * **  *  * ************  *
                                                                              PORTION OF
STEAP-1   247  WREFHYIQSKLGIVSLLLGTIHALIFAWNKWIDIKQFVWYTPPTFMIAVFLPIVVLI    SEQ ID NO:2
STEAP-2   388  WREFSFIQSTLGYVALLISTFHVLIYGWKRAFEEEYYRFYTPPNFVLALVLPSIVIL    PORTION OF
               ****  *** ** * **   * * **  *           **** *  * **  *     SEQ ID NO:6
```

FIG. 11C

```
STEAP1   66  ELFPQWHLPIKIAAIIASLTFLYTLLREVIHPLATSHQQYFYKIPILVINKVLPMVSITL

STEAP3  195  QLFPMWRFPFYLSAVLCVFLFFYCVIRDVIYPYVYEKKDNTFRMAISIPNRIFPITALTL
             *** *   *       * *   * ** *              *   *   *     **

STEAP1  126  LALVYLPGVIAAIVQLHNGTKYKKFPHWLDKWMLTRKQFGLLSFFFAVLHAIYSLSYPMR

STEAP3  255  LALVYLPGVIAAILQLYRGTKYRRFPDWLDHWMLCRKQLGLVALGFAFLHVLYTLVIPIR
             ************* **  **** ** *** *** *** **    ** **  *  *  *

STEAP1  186  RSYRYKLLNWAYQQVQQNKEDAWIEHDVWRMEIYVSLGIVGLAILALLAVTSIPSVSDSL

STEAP3  315  YYVRWRLGNLTVTQAILKKENPFSTSSAWLSDSYVALGILGFFLFVLLGITSLPSVSNAV
              * *   *      *   **     *    **  ***  *  **  **  ** ****

STEAP1  246  TWREFHYIQSKLGIVSLLLGTIHALIFAWNKWIDIKQFVWYTPPTFMIAVFLPIVVLIFK

STEAP3  375  NWREFRFVQSKLGYLTLILCTAHTLVYGGKRFLSPSNLRWYLPAAYVLGLIIPCTVLVIK
              ****  *****   *  * * *  *              ** *    *    * ** *

STEAP1  306  SILFLPCLRKKILKIRHGWEDVTK  PORTION OF SEQ ID NO:2

STEAP3  435  FVLIMPCVDNTLTRIRQGWERNSK  PORTION OF SEQ ID NO:8
              * **    ** *** *   *
```

FIG. 11D

```
STEAP2  29  RKVTVGVIGSGDFAKSLTIRLIRCGYHVVIGSRNPKFASEFFPHVVDVTHHEDALTKTNI

STEAP3  18  KQETVCIFGTGDFGRSLGLKMLQCGYSVVFGSRNPQ-KTTLLPSGAEVLSYSEAAKKSGI
            **  * ***  **      *** ** *****        *    *    *   *  *

STEAP2  89  IFVAIHREHYTSLWDLRHLLVGKILIDVSNNMRINQYPESNAEYLASLFPDSLIVKGFNV

STEAP3  77  IIIAIHREHYDFLTELTEVLNGKILVDISNNLKINQYPESNAEYLAHLVPGAHVVKAFNT
            *  *******  *   *    ****  *** *************  *       **  **

STEAP2  149 VSAWALQLGPKDASRQVYICSNNIQARQQVIELARQLNFIPIDLGSLSSAREIENLPLRL

STEAP3  137 ISAWALQSGALDASRQVFVCGNDSKAKQRVMDIVRNLGLTPMDQGSLMAAKEIEKYPLQL
             ******  *  ******  *  *  *   *   *   *   * ***   *  ***  ** *

STEAP2  209 PTLWRGPVVVAISLATFFFLYSFVRDVIHPYARNQQSDFYKIPIEIVNKTLPIVAITLLS

STEAP3  197 FPMWRFPFYLSAVLCVFLFFYCVIRDVIYPYVYEKKDNTFRMAISIPNRIFPITALTLLA
             *  **  *    *    *  **** **    *  *  *    ** * ***

STEAP2  269 LVYLAGLLAAAYQLYYGTKYRRFPPWLETWLQCRKQLGLLSFFFAMVHVAYSLCLPMRRS

STEAP3  257 LVYLPGVIAAILQLYRGTKYRRFPDWLDHWMLCRKQLGLVALGFAFLHVLYTLVIPIRYY
            ****  *  **  *** *  ********  **   *******   **  **  *  *  * *

STEAP2  329 ERYLFLNMAYQQVHANIENSWNEEEVWRIEMYISFGIMSLGLLSLLAVTSIPSVSNALNW

STEAP3  317 VRWRLGNLTVTQAILKKENPFSTSSAWLSDSYVALGILGFFLFVLLGITSLPSVSNAVNW
             *    *  *   **       *    *   *     **   **   ***  ****** **

STEAP2  389 REPSFIQSTLGYVALLISTFHVLIYGWKRAFEEEYYRFYTPPNFVLALVLPSIVIL  PORTION OF
                                                                      SEQ ID NO:6
STEAP3  377 REFRFVQSKLGYLTLILCTAHTLVYGGKRFLSPSNLRWYLPAAYVLGLIIPCTVLV  PORTION OF
            *** * ** ***  *  ** *  * ***  *  *  * **  **  * * *  *   SEQ ID NO:8
```

A
1. Brain
2. Heart
3. Kidney
4. Liver
5. Lung
6. Pancreas
7. Placenta
8. Skeletal Muscle B
1. Colon
2. Ovary
3. Leukocytes
4. Prostate
5. Small Intestine
6. Spleen
7. Testis
8. Thymus

A
1. Brain
2. Heart
3. Kidney
4. Liver
5. Lung
6. Pancreas
7. Placenta
8. Skeletal Muscle

B
1. Colon
2. Ovary
3. Leukocytes
4. Prostate
5. Small Intestine
6. Spleen
7. Testis
8. Thymus A
1. Brain
2. Prostate
3. LAPC-4 AD
4. LAPC-4 AI
5. LAPC-9 AD
6. HeLa
7. Murine cDNA
8. Neg. control B
1. Colon
2. Ovary
3. Leukocytes
4. Prostate
5. Small Intestine
6. Spleen
7. Testis
8. Thymus

Lanes
1) 1kb ladder
2) human female genomic
3) 12P11 BAC mus
4) human female genomic
5) 12P11 BAC mus
6) 3T3

SERPENTINE TRANSMEMBRANE ANTIGENS EXPRESSED IN HUMAN CANCERS AND USES THEREOF

CROSS-REFERENCE TO RELATED APPLICATIONS

This is a Divisional of U.S. application Ser. No. 09/455,486, 6 Dec. 1999, now U.S. Pat. No. 6,833,438, which is a Continuation-In-Part of U.S. application Ser. No. 09/323,873, filed 1 Jun. 1999, now U.S. Pat. No. 6,329,503. The contents of these applications are incorporated herein by reference.

FIELD OF THE INVENTION

The invention described herein relates to a family of novel genes and their encoded proteins and tumor antigens, termed STEAPs, and to diagnostic and therapeutic methods and compositions useful in the management of various cancers, particularly including prostate cancer, colon cancer, bladder cancer, ovarian cancer and pancreatic cancer.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment, and many experience a recurrence.

Generally speaking, the fundamental problem in the management of the deadliest cancers is the lack of effective and non-toxic systemic therapies. While molecular medicine promises to redefine the ways in which these cancers are managed, progress in this area has been slow despite intensive worldwide efforts to develop novel molecular diagnostics and therapeutics. Fundamental to these efforts is the search for truly tumor-specific genes and proteins that could be used as diagnostic and prognostic markers and/or therapeutic targets or agents.

As discussed below, the management of prostate cancer serves as a good example of the limited extent to which molecular biology has translated into real progress in the clinic. With limited exceptions, the situation is similar for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH).

Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Accordingly, the lack of a prostate tumor marker that can accurately detect early-stage, localized tumors remains a significant limitation in the management of prostate cancer. A similar problem is the lack of an effective prognostic marker for determining which cancers are indolent and which ones are or will be aggressive. PSA, for example, cannot accurately discriminate between these alternatives.

Although the serum PSA assay has been a very useful tool, its specificity and general utility is widely regarded as lacking in several important respects. For example, PSA is not a disease-specific marker, as elevated levels of PSA are detectable in a large percentage of patients with BPH and prostatitis (25-86%)(Gao et al., 1997, Prostate 31: 264-281), as well as in other nonmalignant disorders and in some normal men. Elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. In addition, PSA diagnostics have sensitivities of only between 57-79% (Cupp & Osterling, 1993, Mayo Clin Proc 68:297-306), and thus miss identifying prostate cancer in a significant population of men with the disease. Moreover, it is now recognized that PSA is not prostate-specific (Gao et al., supra, for review). Various methods designed to improve the specificity of PSA-based detection have been described, such as measuring PSA density and the ratio of free vs. complexed PSA. However, none of these methodologies have been able to reproducibly distinguish benign from malignant prostate disease.

Similarly, there is no available marker that can predict the emergence of the typically fatal metastatic stage of prostate cancer. Diagnosis of the metastatic stage is presently achieved by open surgical or laparoscopic pelvic lymphadenectomy, whole body radionuclide scans, skeletal radiography, and/or bone lesion biopsy analysis. Clearly, better imaging and less invasive diagnostic methods would improve diagnostic accuracy, ease the burden such procedures place on patients, and open therapeutic options.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759-766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 c DNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigen of the Prostate). Four particular human STEAPs are described and characterized herein. The human STEAPs exhibit a high degree of structural conservation among them but show no significant structural homology to any known human proteins.

The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers. In particular, cell surface expression of STEAP-1 has been definitively confirmed in a variety of prostate and prostate cancer cells, bladder cancer cells and colon cancer cells. These characteristics indicate that STEAP-1 is a specific cell-surface tumor antigen expressed at high levels in prostate, bladder, colon, and other cancers.

A second member of the family, STEAP-2, is a 454 amino add protein with a predicted molecular topology similar to that of STEAP-1. STEAP-2, like STEAP-1, is prostate-specific in normal human tissues and is also expressed in prostate cancer. Alignment of the STEAP-2 and STEAP-1 ORFs shows 54.9% identity over a 237 amino acid residue overlap, and the locations of the six putative transmembrane domains in STEAP-2 coincide with the locations of the transmembrane domains in STEAP-1 (FIG. 11A).

STEAP-3 and STEAP-4 are also described herein. These are also structurally related, and show unique expression profiles. In particular, STEAP-3 and STEAP-4 appear to show a different tissue restriction patterns. An amino acid sequence alignment of all four STEAPs is shown in FIG. 11A.

The invention provides polynucleotides corresponding or complementary to all or part of the STEAP genes, mRNAs, and/or coding sequences, preferably in isolated form, including polynucleotides encoding STEAP proteins and fragments thereof, DNA, RNA, DNA/RNA hybrid, and related molecules, polynucleotides or oligonucleotides complementary to the STEAP genes or mRNA sequences or parts thereof, and polynucleotides or oligonucleotides which hybridize to the STEAP genes, mRNAs, or to STEAP-encoding polynucleotides. Also provided are means for isolating cDNAs and the genes encoding STEAPs. Recombinant DNA molecules containing STEAP polynucleotides, cells transformed or transduced with such molecules, and host-vector systems for the expression of STEAP gene products are also provided. The invention further provides STEAP proteins and polypeptide fragments thereof. The invention further provides antibodies that bind to STEAP proteins and polypeptide fragments thereof, including polyclonal and monodonal antibodies, murine and other mammalian antibodies, chimeric antibodies, humanized and fully human antibodies, and antibodies labeled with a detectable marker, and antibodies conjugated to radionuclides, toxins or other therapeutic compositions. The invention further provides methods for detecting the presence of STEAP polynucleotides and proteins in various biological samples, as well as methods for identifying cells that express a STEAP. The invention further provides various therapeutic compositions and strategies for treating prostate cancer, including particularly, antibody, vaccine and small molecule therapy.

BRIEF DESCRIPTION OF THE FIGURES

FIG. 2. Predominant expression of STEAP-1 in prostate tissue. First strand cDNA was prepared from 16 normal tissues, the LAPC xenografts (4AD, 4AI and 9AD) and HeLa cells. Normalization was performed by PCR using primers to actin and GAPDH. Semi-quantitative PCR, using primers derived from STEAP-1 (8P1D4) cDNA (FIG. 1A), shows predominant expression of STEAP-1 in normal prostate and the LAPC xenografts. The following primers were used to amplify STEAP-1:

```
8P1D4.1
5' ACTTTGTTGATGACCAGGATTGGA 3'    (SEQ ID NO: 14)

8P1D4.2
5' CAGAACTTCAGCACACACAGGAAC 3'    (SEQ ID NO: 15)
```

Figure 3A:
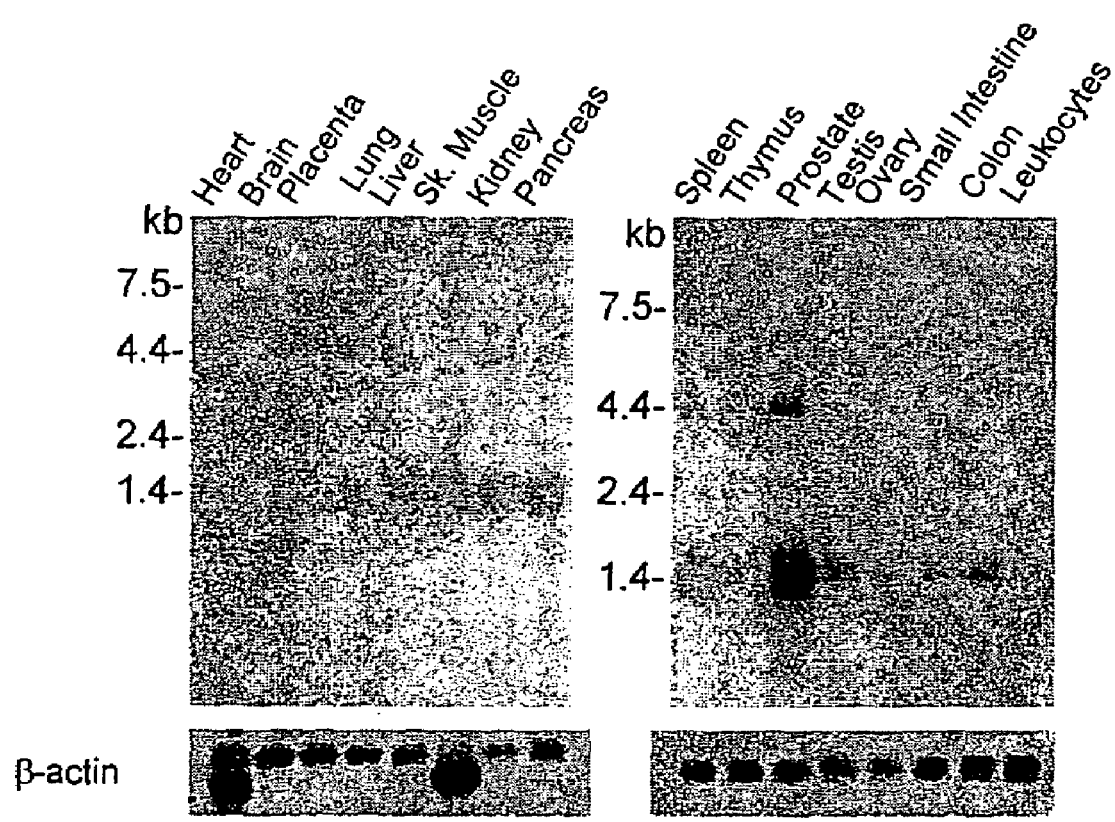

FIG. 3. Northern blot analyses of STEAP-1 expression in various normal human tissues and prostate cancer xenografts, showing predominant expression of STEAP-1 in prostate tissue. FIG. 3A: Two multiple tissue northern blots (Clontech) were probed with a full length STEAP cDNA clone 10 (FIG. 1A: SEQ ID NO: 1). Size standards in kilobases (kb) are indicated on the side. Each lane contains 2 μg of mRNA that was normalized by using a β-actin probe. FIG. 3B: Multiple tissue RNA dot blot (Clontech, Human Master Blot cat#

7770-1) probed with STEAP-1 cDNA clone 10 (FIG. 1A; SEQ ID NO: 1), showing approximately five-fold greater expression in prostate relative to other tissues with significant detectable expression.

FIG. 4A-4B. Nucleotide sequence (SEQ ID NO: 4) of STEAP-1 GTH9 clone corresponding to the 4 kb message on northern blots (FIG. 3A). The sequence contains an intron of 2399 base pairs relative to the STEAP-1 clone 10 sequence of FIG. 1A; coding regions are nucleotides 96-857 and 3257-3510 (indicated in bold). The start ATG is in bold and underlined, the STOP codon is in bold and underlined, and the intron-exon boundaries are underlined.

FIG. 5. Expression of STEAP-1 in prostate and multiple cancer cell lines and prostate cancer xenografts. Xenograft and cell line filters were prepared with 10 μg of total RNA per lane. The blots were analyzed using the STEAP-1 clone 10 as probe. All RNA samples were normalized by ethidium bromide staining and subsequent analysis with a β-actin probe. FIG. 5A: Expression in various cancer cell lines and xenografts and prostate. Lanes as follows: (1) PrEC cells, (2) normal prostate tissue, (3) LAPC-4 AD xenograft, (4) LAPC-4 AI xenograft, (5) LAPC-9 AD xenograft, (6) LAPC-9 AI xenograft, (7) LNCaP cells, (8) PC-3 cells, (9) DU145 cells, (10) PANC-1 cells, (11) BxPC-3 cells, (12) HPAC cells, (13) Capan-1 cells, (14) CACO-2 cells, (15) LOVO cells, (16) T84 cells, (17) COLO-205 cells, (18) KCL-22 cells (acute lymphocytic leukemia, ALL), (19) HT1197 cells, (20) SCABER cells, (21) UM-UC-3 cells, (22) TCCSUP cells, (23) J 82 cells, (24) 5637 cells, (25) RD-ES cells (Ewing sarcoma, EWS), (26) CAMA-1 cells, (27) DU4475 cells, (28) MCF-7 cells, (29) MDA-MB-435s cells, (30) NTERA-2 cells, (31) NCCIT cells, (32) TERA-1 cells, (33) TERA-2 cells, (34) A431 cells, (35) HeLa cells, (36) OV-1063 cells, (37) PA-1 cells, (38) SW 626 cells, (39) CAOV-3 cells. FIG. 5B: The expression of STEAP-1 in subcutaneously (sc) grown LAPC xenografts compared to the expression in LAPC-4 and LAPC-9 xenografts grown in the tibia (it) of mice.

Figure 6:
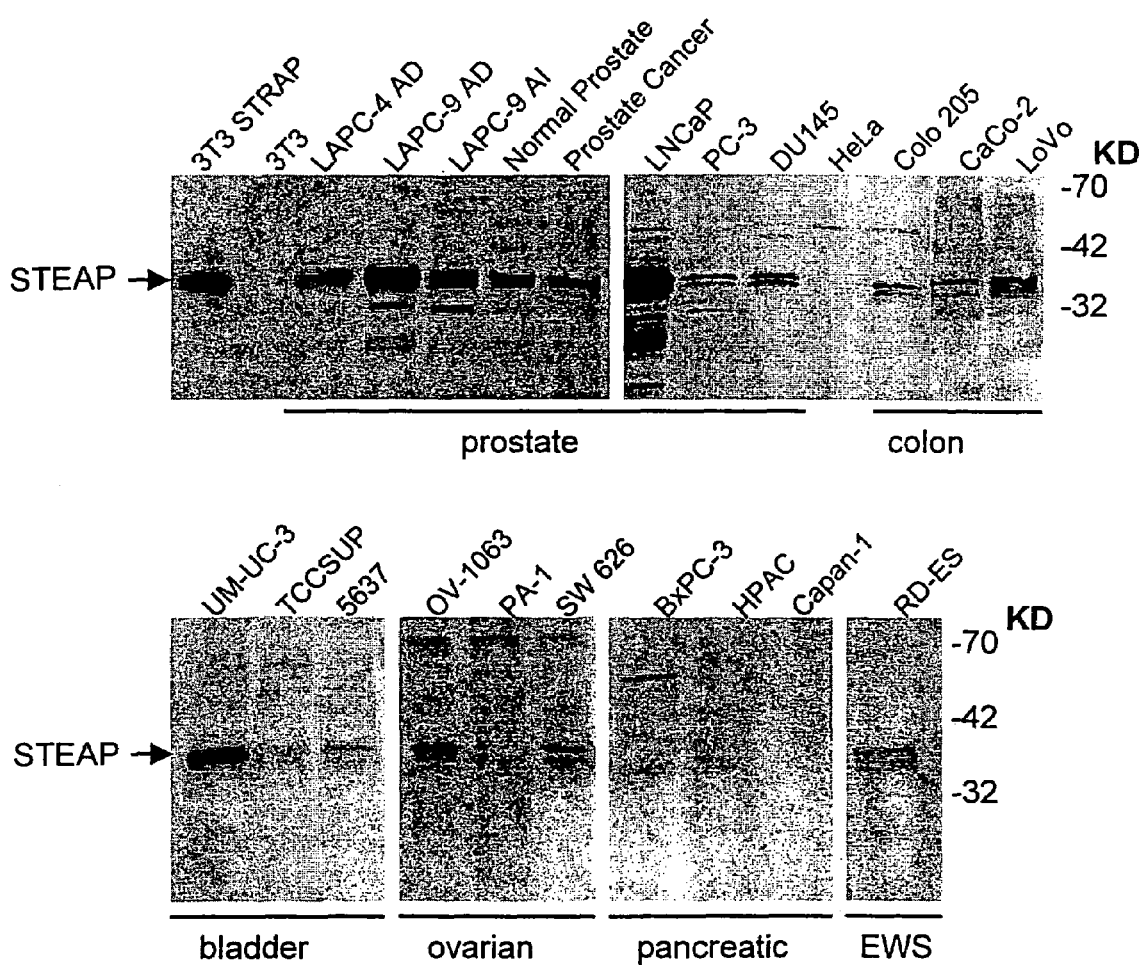

FIG. 6. Western blot analysis of STEAP-1 protein expression in tissues and multiple cell lines. Western blots of cell lysates prepared from prostate cancer xenografts and cell lines were probed with a polyclonal anti-STEAP-1 antibody preparation (see Example 3C for details). The samples contain 20 μg of protein and were normalized with anti-Grb-2 probing of the Western blots.

FIG. 7. Cell surface biotinylation of STEAP-1. FIG. 7A: Cell surface biotinylation of 293T cells transfected with vector alone or with vector containing cDNA encoding 6His-tagged STEAP-1. Cell lysates were immunoprecipitated with specific antibodies, transferred to a membrane and probed with horseradish peroxidase-conjugated streptavidin. Lanes 1-4 and 6 correspond to immunoprecipitates from lysates prepared from STEAP-1 expressing 293T cells. Lanes 5 and 7 are immunoprecipitates from vector transfected cells. The immunoprecipitations were performed using the following antibodies: (1) sheep non-immune, (2) anti-Large T antigen, (3) anti-CD71 (transferrin receptor), (4) anti-His, (5) anti-His, (6) anti-STEAP-1, (7) anti-STEAP-1. FIG. 7B: Prostate cancer (LNCaP, PC-3, DU145), bladder cancer (UM-UC-3, TCCSUP) and colon cancer (LOVO, COLO) cell lines were either biotinylated (+) or not (−) prior to lysis. Western blots of streptavidin-gel purified proteins were probed with anti-STEAP-1 antibodies. Molecular weight markers are indicated in kilodaltons (kD).

Figure 8:
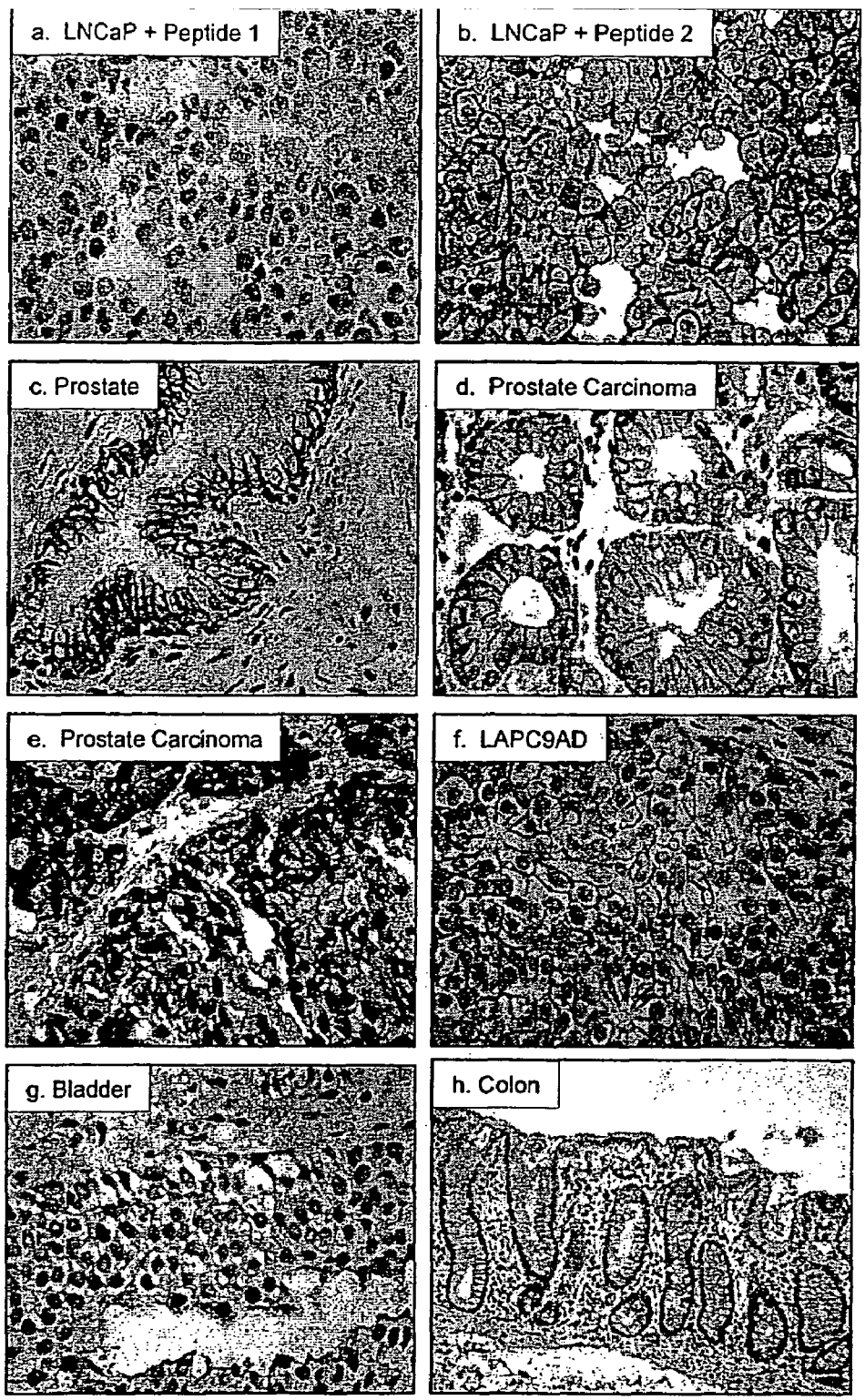

FIG. 8. Immunohistochemical analysis of STEAP-1 expression using anti-STEAP-1 polyclonal antibody. Tissues were fixed in 10% formalin and embedded in paraffin. Tissue sections were stained using anti-STEAP-1 polyclonal antibodies directed towards the N-terminal peptide. Samples include: (a) LNCaP cells probed in the presence of N-terminal STEAP-1 peptide 1, (b) LNCaP plus non specific peptide 2, (c) normal prostate tissue, (d) grade 3 prostate carcinoma, (e) grade 4 prostate carcinoma, (f) LAPC-9 AD xenograft, (g) normal bladder, (h) normal colon. All images are at 400× magnification.

FIGS. 9A-9D. Nucleotide and deduced amino acid sequences of STEAP-2 (98P4B6) clone GTD3 cDNA (SEQ ID NOs: 5 and 6. respectively). The start methionine and Kozak sequence are indicated in bold, and the putative transmembrane domains are underlined in bold. The 5' UTR exhibits a high GC content of 72%.

FIGS. 10A-10E. Nucleotide and deduced amino acid sequences of STEAP-3 (SEQ ID NOs: 7 and 8, respectively). Kozak region is bolded.

FIG. 10F. Nucleotide sequences (SEQ ID NOs: 9-12, respectively) of dbest database entries corresponding to additional STEAP family members obtained by searching with the protein sequence of STEAP-1.

Figure 11A-1:
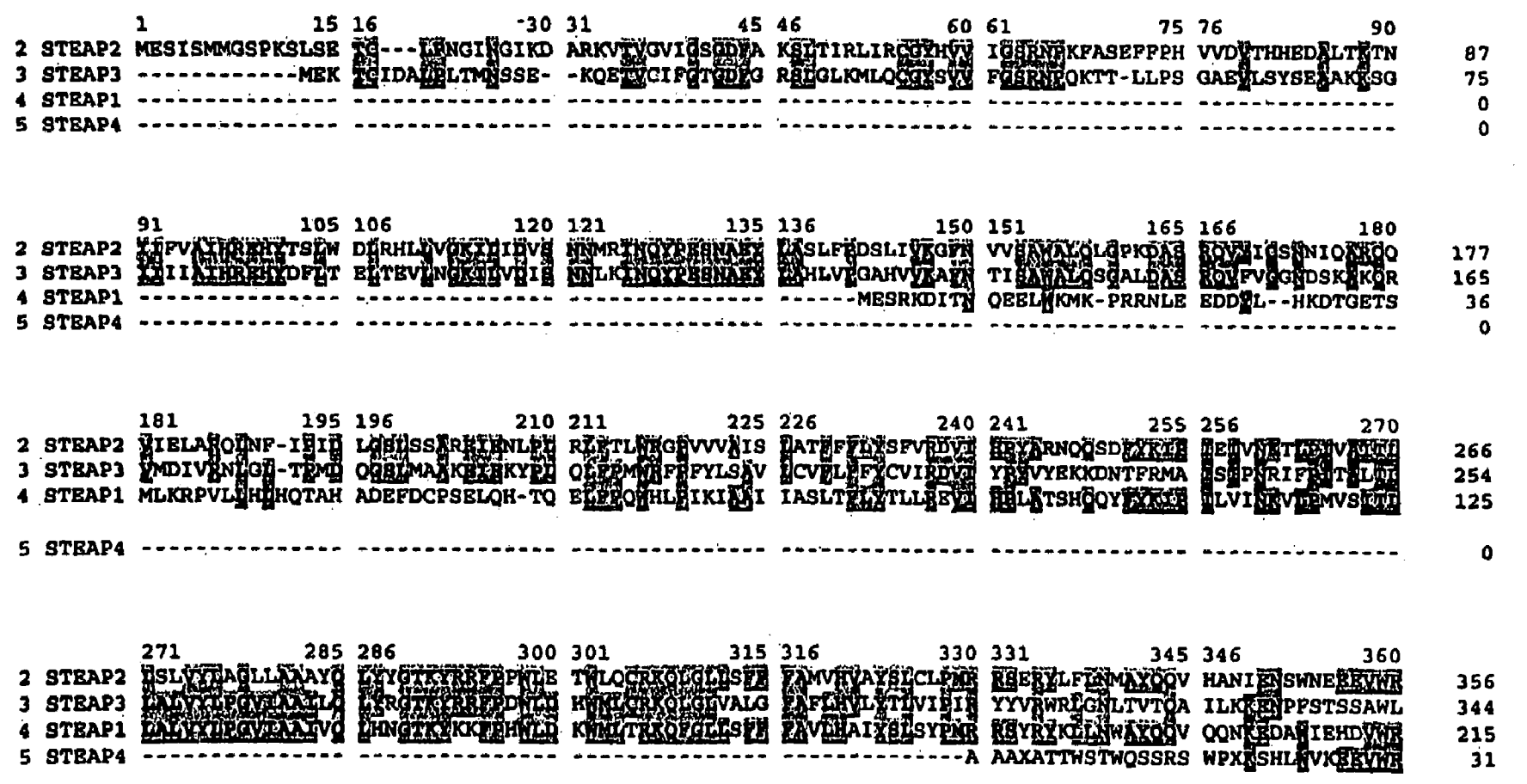
Figure 11A-2:
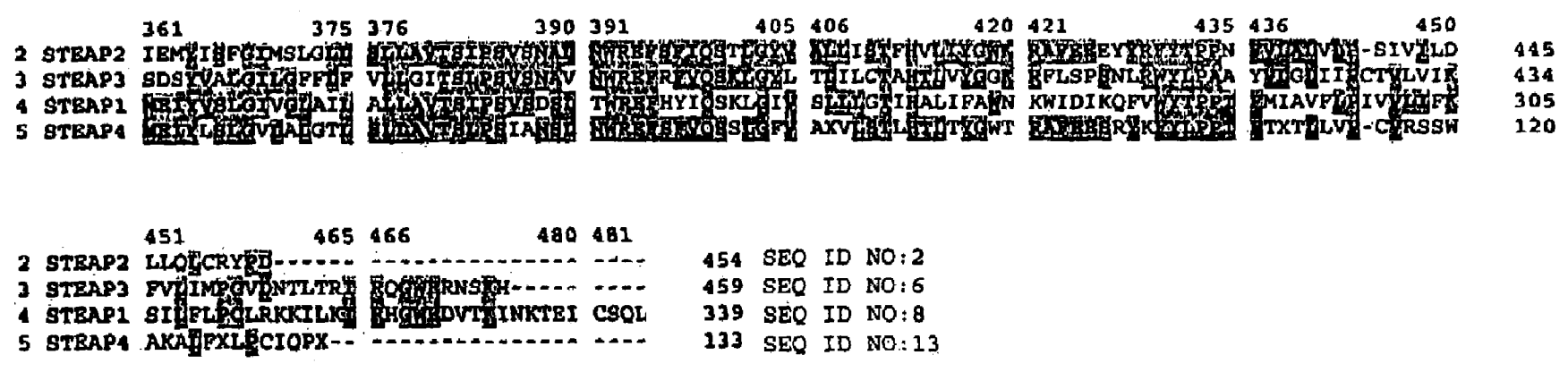

FIG. 11. Primary structural comparisons of STEAP family proteins:

FIG. 11A-1-11A-2. Amino acid sequence alignment of STEAPs 1-4 using the PIMA 1.4 program; transmembrane domains identified by the SOSUI program are in bold. PIMA maximal linkage clustering results shown; identical residues shown in bold.

FIG. 11B. Amino acid sequence alignment of STEAP-1 (8P1D4 clone 10; SEQ ID NO: 2) and STEAP-2 (98P4B6 clone GTD3; SEQ ID NO: 6) sequences. The alignment was performed using the SIM alignment program of the Baylor College of Medicine Search Launcher Web site. Transmembrane domains are indicated in boldface. The results show a 54.9% identity in a 237 residues overlap (Score: 717.0; Gap frequency: 0.0%).

FIG. 11C. Amino acid sequence alignment of STEAP-1 and STEAP-3 (98P4B6 clone GTD3; SEQ ID NO: 8) sequences. Identical residues indicated with asterisks. SIM results: 40.9% identity in 264 residues overlap; Score: 625.0; Gap frequency: 0.0%.

FIG. 11D. Amino acid sequence alignment of STEAP-2 and STEAP-3 (98P4B6 clone GTD3; SEQ ID NO: 8) sequences. Identical residues indicated with asterisks. SIM results: 47.8% identity in 416 residues overlap; Score: 1075.0; Gap frequency: 0.2%.

Figure 12A:
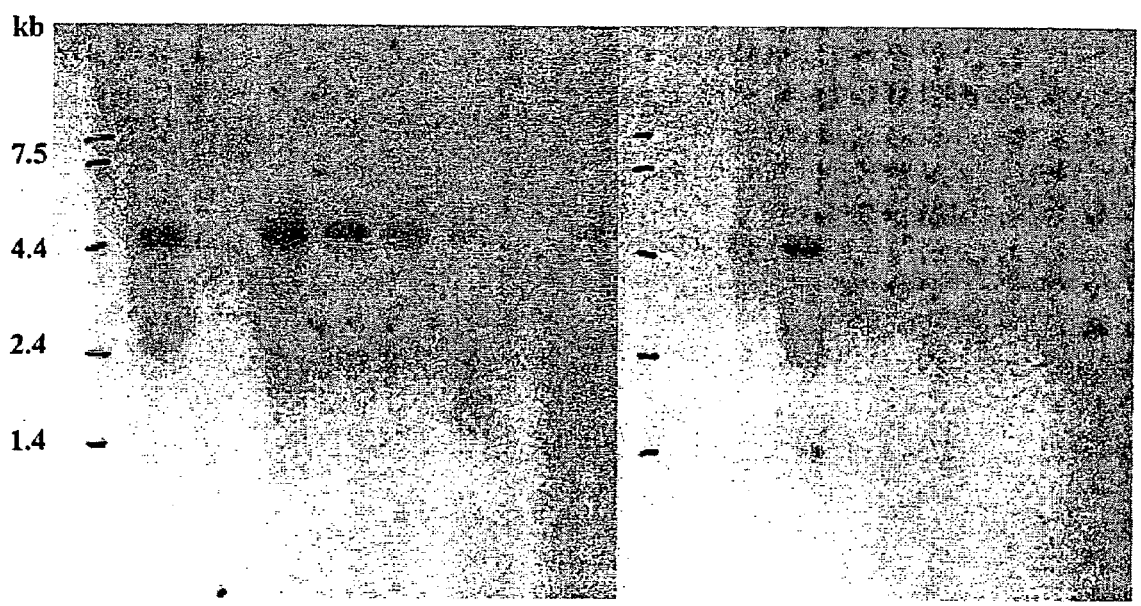
Figure 12B:
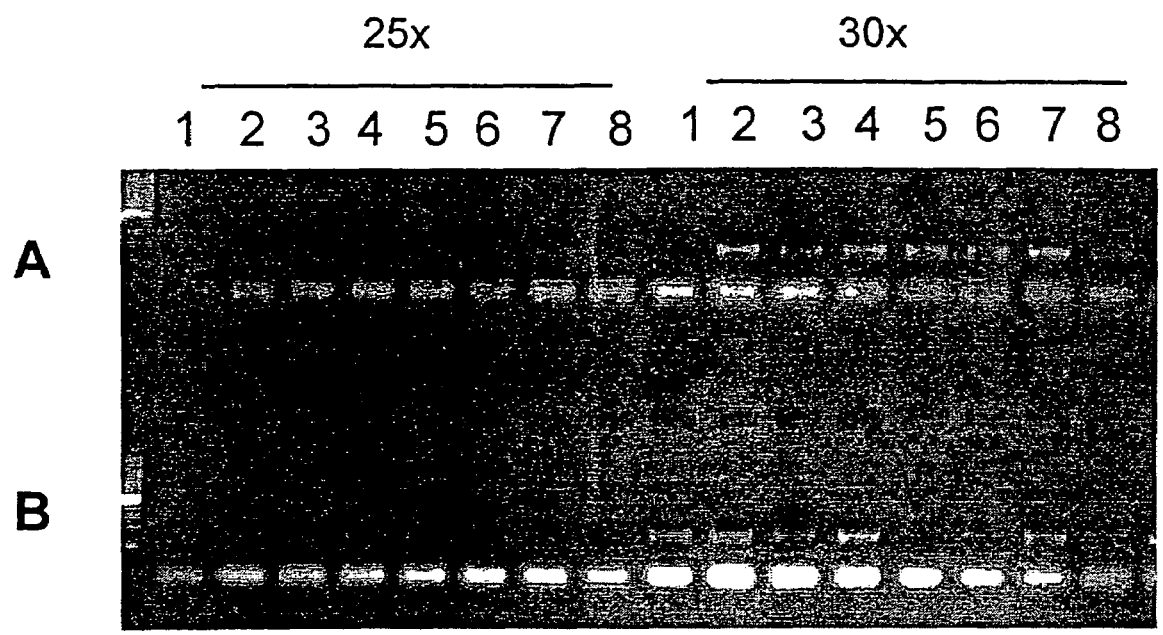

FIG. 12. Expression of STEAP-3 mRNA in normal tissues by Northern blot (FIG. 12A) and RT-PCR (FIG. 12B). For RT-PCR analysis, first strand cDNA was prepared from 16 normal tissues. Normalization was performed by PCR using primers to actin and GAPDH. Semi-quantitative PCR, using primers to AI139607, shows predominant expression of AI139607 in placenta and prostate after 25 cycles of amplification. The following primers were used to amplify AI139607:

```
AI139607.1
5' TTAGGACAACTTGATCACCAGCA 3'    (SEQ ID NO: 16)

AI139607.2
5' TGTCCAGTCCAAACTGGGTTATTT 3'   (SEQ ID NO: 17)
```

Figure 13:
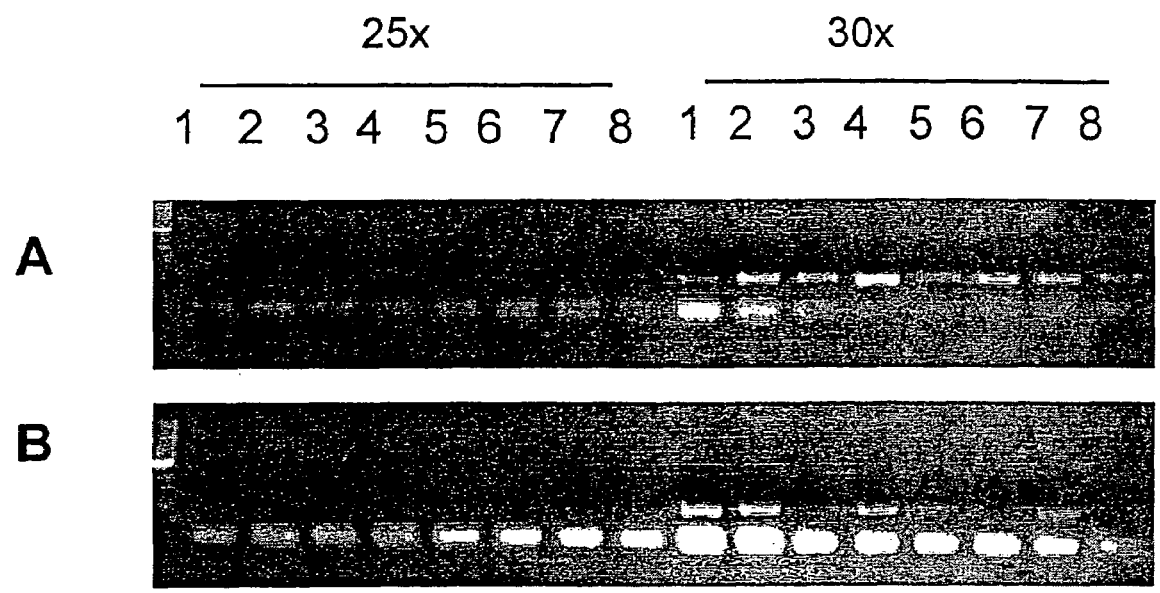

FIG. 13. Predominant expression of STEAP-4/R80991 in liver. First strand cDNA was prepared from 16 normal tissues. Normalization was performed by PCR using primers to actin and GAPDH. Semi-quantitative PCR, using primers to R80991, shows predominant expression of R80991 in liver after 25 cycles of amplification. The following primers were used to amplify R80991:

```
R80991.1
5' AGGGAGTTCAGCTTCGTTCAGTC 3'    (SEQ ID NO: 18)

R80991.2
5' GGTAGAACTTGTAGCGGCTCTCCT 3'    (SEQ ID NO: 19)
```

Figure 14:
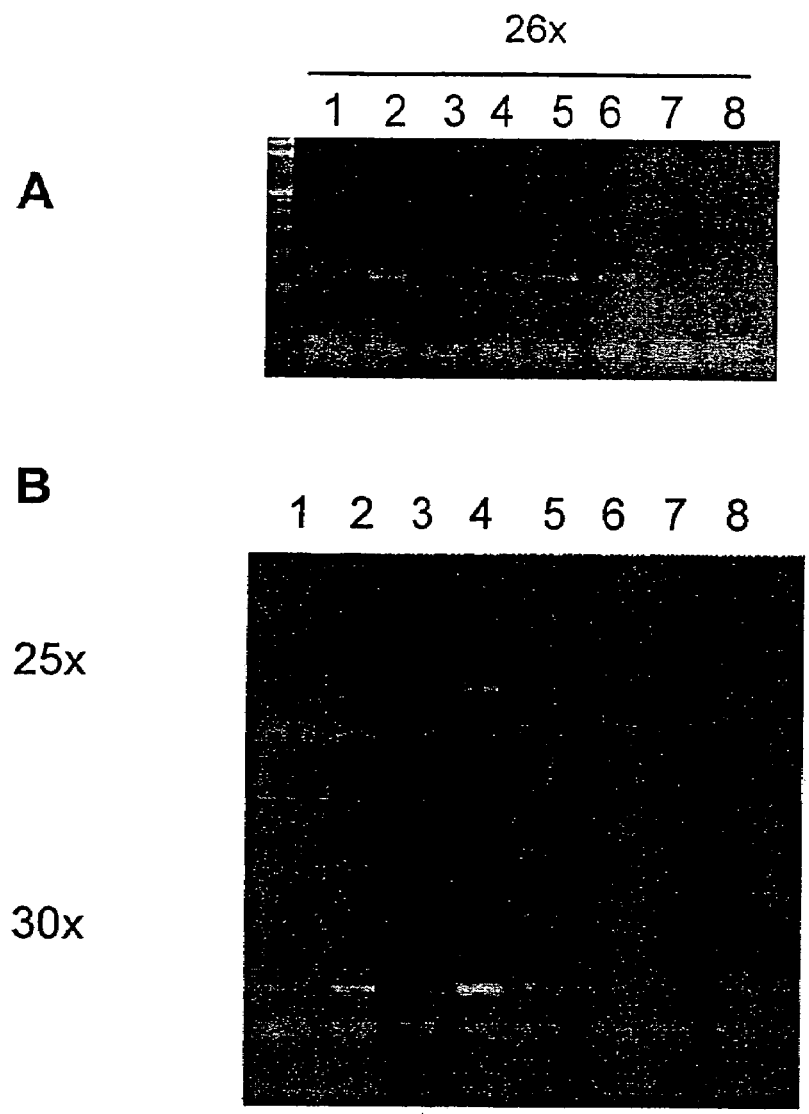

FIG. 14. Predominant expression of STEAP-2 (98P4B6) in prostate tissue. First strand cDNA was prepared from 8 normal tissues, the LAPC xenografts (4AD, 4AI and 9AD) and HeLa cells. Normalization was performed by PCR using primers to actin and GAPDH. Semi-quantitative PCR, using primers to 98P4B6, shows predominant expression of 98P4B6 in normal prostate and the LAPC xenografts. The following primers were used to amplify STEAP II:

```
98P4B6.1
5' GACTGAGCTGGAACTGGAATTTGT 3'    (SEQ ID NO: 20)

98P4B6.2
5' TTTGAGGAGACTTCATCTCACTGG 3'    (SEQ ID NO:21)
```

Figure 15:
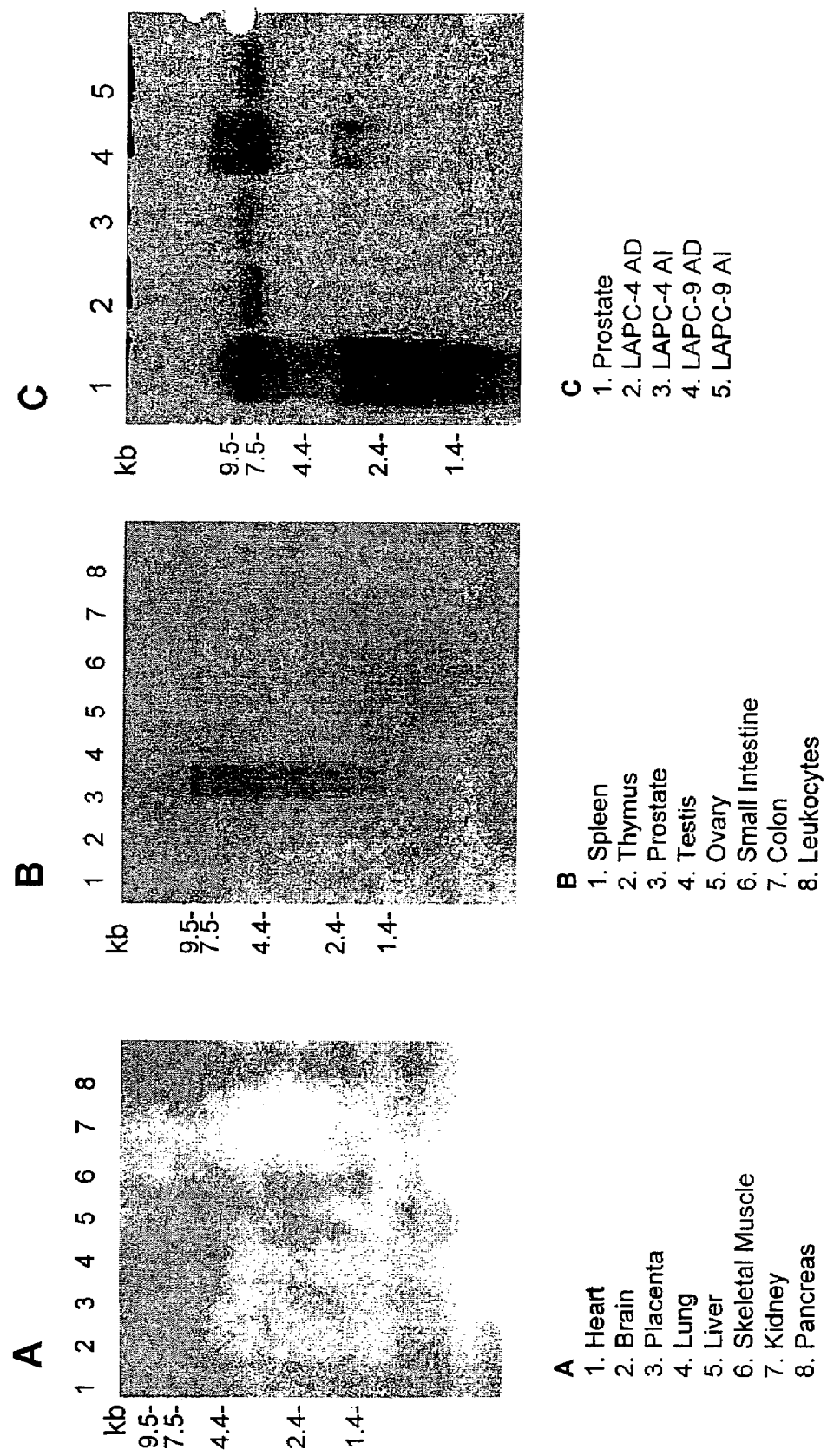

FIG. 15. Expression of the prostate-specific STEAP-2/98P4B6 gene in normal tissues and in prostate cancer xenografts determined by Northern blot analysis. Human normal tissue filters (A and B) were obtained from CLONTECH and contain 2 µg of mRNA per lane. Xenograft filter (C) was prepared with 10 µg of total RNA per lane. The blots were analyzed using the SSH derived 98P4B6 clone as probe. All RNA samples were normalized by ethidium bromide staining.

Figure 16:
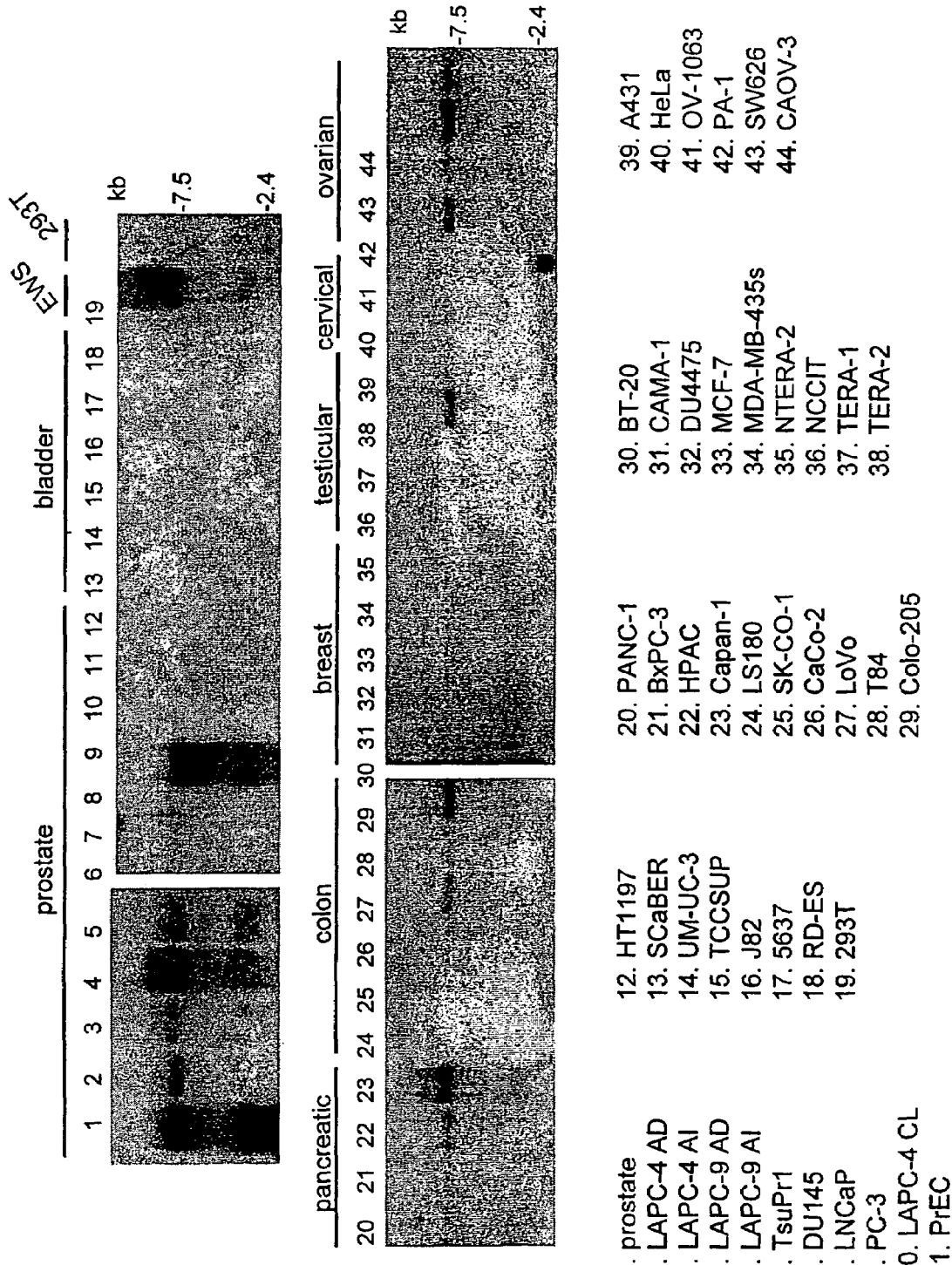

FIG. 16. Expression of STEAP-2 in prostate and select cancer cell lines as determined by Northern blot analysis. Xenograft and cell line filters were prepared with 10 µg total RNA per lane. The blots were analyzed using an SSH derived 98P4B6 clone as probe. All RNA samples were normalized by ethidium bromide staining.

Figure 17:
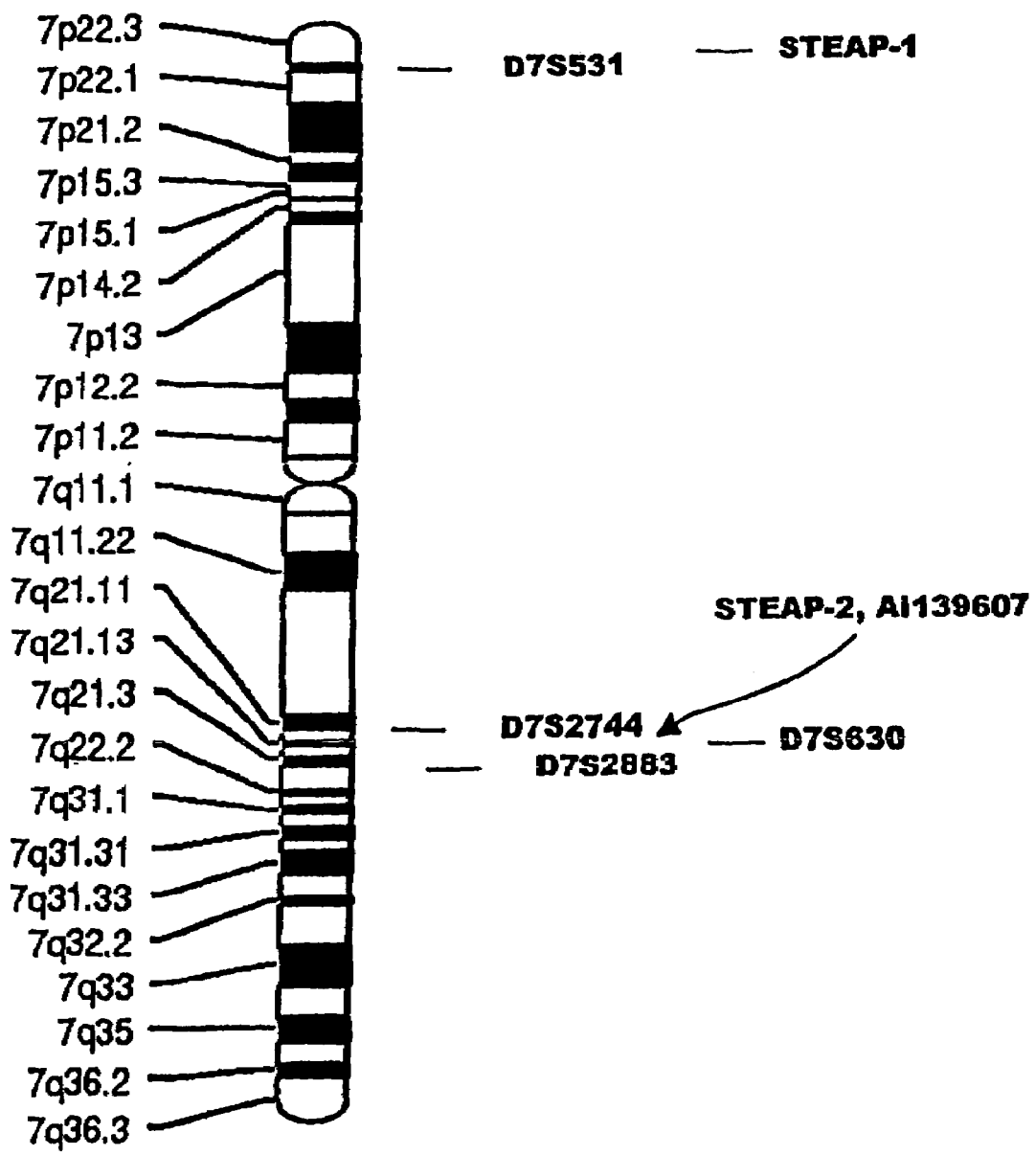

FIG. 17. Chromosomal localization of STEAP family members. The chromosomal localizations of the STEAP genes described herein were determined using the GeneBridge4 radiation hybrid panel (Research Genetics, Huntsville Ala.). The mapping for STEAP-2 and A1139607 was performed using the Stanford G3 radiation hybrid panel (Research Genetics, Huntsville Ala.).

Figure 18:

FIG. 18. Schematic representation of Intron-Exon boundaries within the ORF of human STEAP-1 gene. A total of 3 introns (i) and 4 exons (e) were identified.

Figure 19:
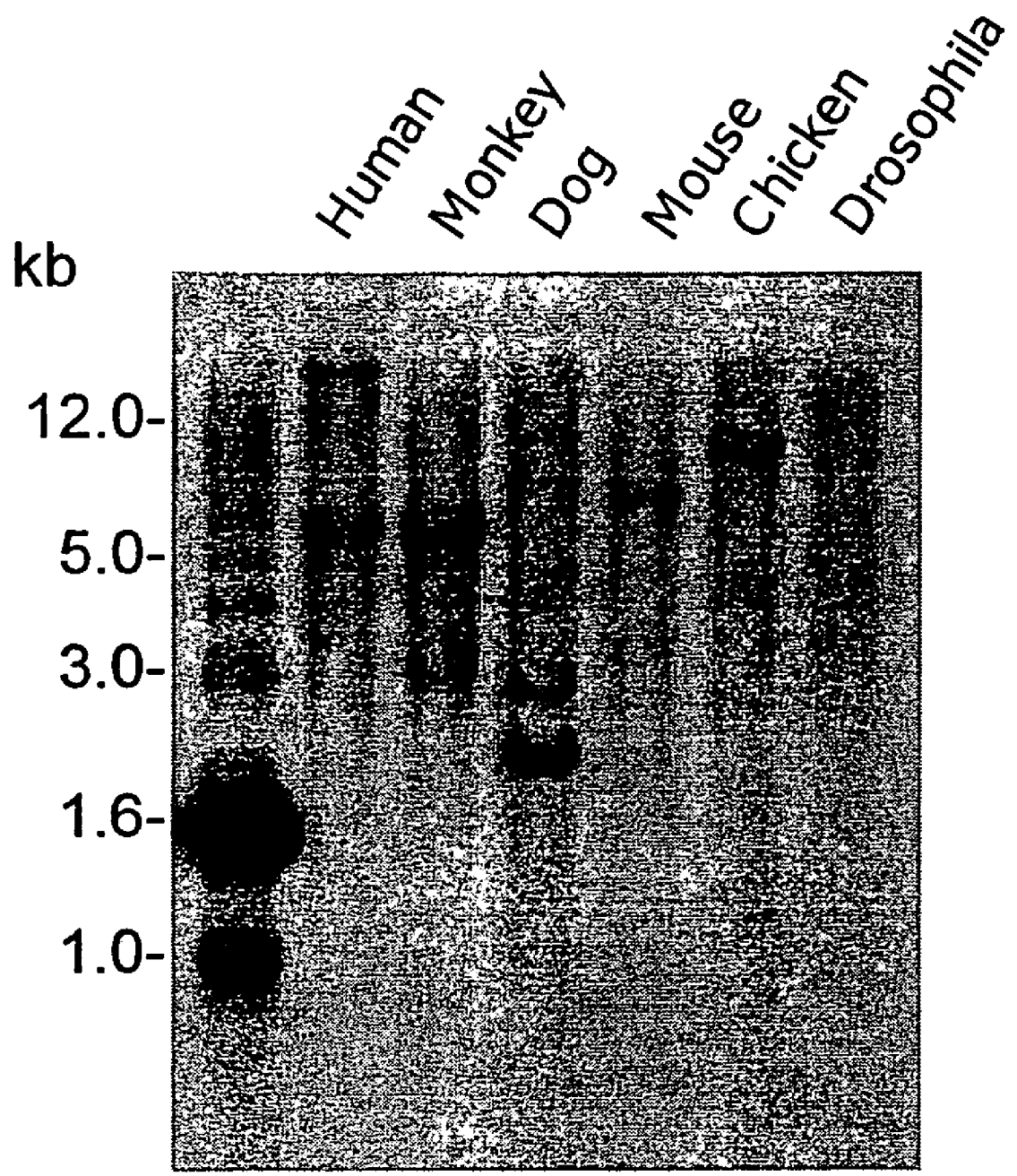

FIG. 19. Zooblot southern analysis of STEAP-1 gene in various species. Genomic DNA was prepared from several different organisms including human, monkey, dog, mouse, chicken and Drosophila. Ten micrograms of each DNA sample was digested with EcoRI, blotted onto nitrocellulose and probed with a STEAP-1 probe. Size standards are indicated on the side in kilobases (kb).

Figure 20:
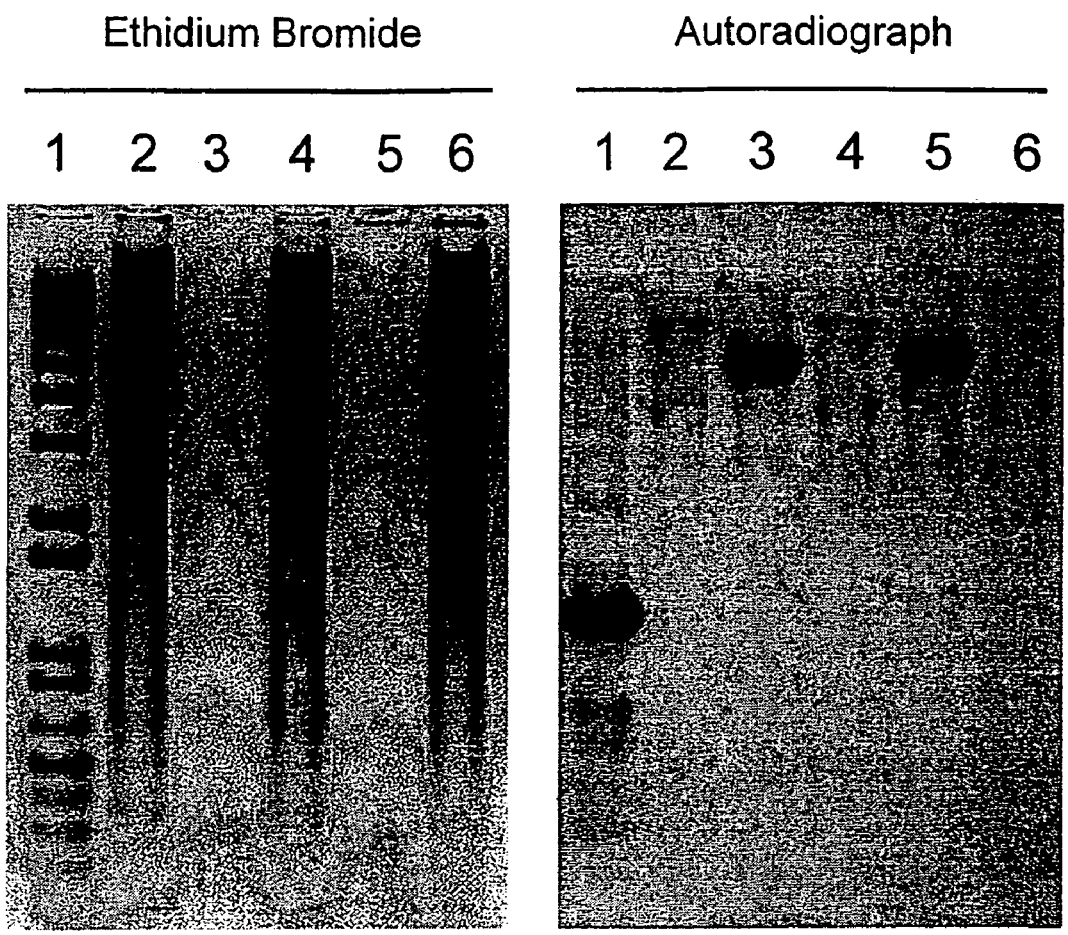

FIG. 20. Southern blot analysis of mouse BAC with a STEAP-1 probe. DNA was prepared from human cells to isolate genomic DNA and from a mouse BAC clone (12P11) that contains the mouse STEAP gene. Each DNA sample was digested with EcoRI, blotted onto nitrocellulose and probed. Eight micrograms of genomic DNA was compared to 250 ng of mouse BAC DNA.

DETAILED DESCRIPTION OF THE INVENTION

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 8 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/ 6XSSC/0.1% SDS/100 µg/ml ssDNA, in which temperatures for hybridization are above 37 degrees C. and temperatures for washing in 0.1XSSC/0.1% SDS are above 55 degrees C., and most preferably to stringent hybridization conditions.

In the context of amino acid sequence comparisons, the term "identity" is used to express the percentage of amino add residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

Molecular and Biochemical Features of the STEAPs

The invention relates to a novel family of proteins, termed STEAPs. Four STEAPs are specifically described herein by way of structural, molecular and biochemical features. As is further described in the Examples which follow, the STEAPs have been characterized in a variety of ways. For example, analyses of nucleotide coding and amino acid sequences were conducted in order to identify conserved structural elements within the STEAP family. Extensive RT-PCR and Northern blot analyses of STEAP mRNA expression were conducted in order to establish the range of normal and cancerous tissues expressing the various STEAP messages. Western blot, immunohistochemical and flow cytometric analyses of STEAP protein expression were conducted to determine protein expression profiles, cell surface localization and gross molecular topology of STEAP.

Figure 1B:
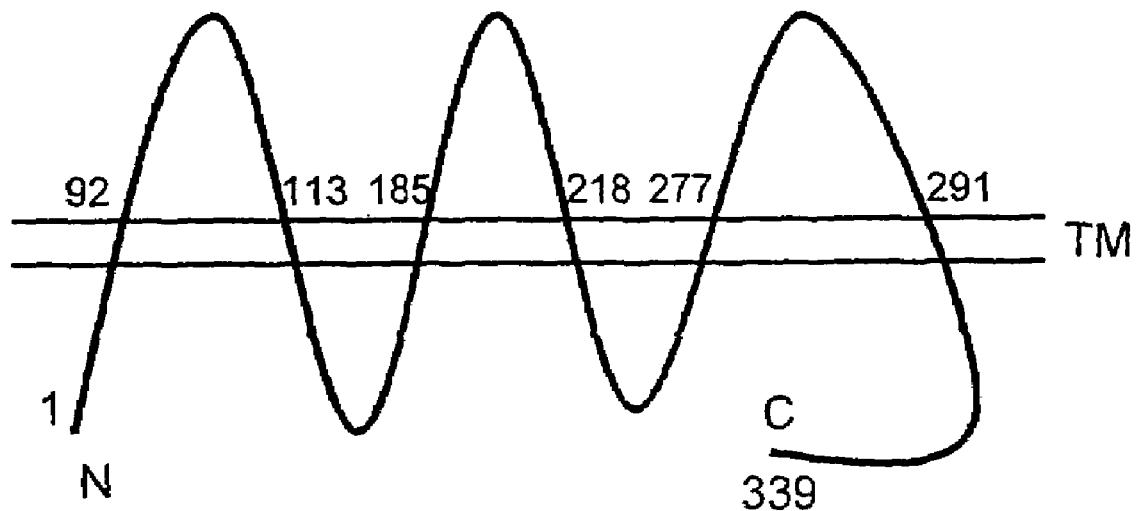
FIG. 1. STEAP-1 structure. 1A-1-1A-2: Nucleotide and deduced amino acid sequences of STEAP-1 (8P1B4) clone 10 cDNA (SEQ ID NOS. 1 and 2, respectively). The start Methionine is indicated in bold at amino acid residue position 1 and six putative transmembrane domains are indicated in bold and are underlined. 1B: Schematic representation of STEAP- 1 transmembrane orientation; amino acid residues bordering the predicted extracellular domains are indicated and correspond to the numbering scheme of FIG. 1A. 1C: G/C rich 5' non-coding sequence of the STEAP-1 gene as determined by overlapping sequences of clone 10 and clone 3 (SEQ ID NO:3).

The prototype member of the STEAP family, STEAP-1, is a six-transmembrane cell surface protein of 339 amino acids with no identifiable homology to any known human protein. The cDNA nucleotide and deduced amino acid sequences of human STEAP-1 are shown in FIG. 1A. A gross topological schematic of the STEAP-1 protein integrated within the cell membrane is shown in FIG. 1B. STEAP-1 expression is predominantly prostate-specific in normal tissues. Specifically, extensive analysis of STEAP-1 mRNA and protein expression in normal human tissues shows that STEAP-1 protein is predominantly expressed in prostate and, to a far smaller degree, in bladder. STEAP-1 mRNA is also relatively prostate specific, with only very low level expression detected in a few other normal tissues. In cancer, STEAP-1 mRNA and protein is consistently expressed at high levels in prostate cancer (including androgen-dependent and androgen-independent tumors) and during all stages of the disease. STEAP-1 is also expressed in other cancers. Specifically, STEAP-1 mRNA is expressed at very high levels in bladder, colon, pancreatic, and ovarian cancer (as well as other cancers). In addition, cell surface expression of STEAP-1 protein has been established in prostate, bladder and colon cancers. Therefore, STEAP-1 has all of the hallmark characteristics of an excellent therapeutic target for the treatment of certain cancers, including particularly prostate, colon and bladder carcinomas.

A second member of the family, STEAP-2, is a 454 amino acid protein encoded by a distinct gene and having a predicted molecular topology similar to that of STEAP-1. The cDNA nucleotide and deduced amino add sequences of STEAP-2 are shown in FIG. 9. Amino add alignment of the STEAP-1 and STEAP-2 sequences show a high degree of structural conservation (54.9% identity over a 237 amino acid residue overlap, and the locations of the six putative transmembrane domains in STEAP-1 and STEAP-2 coincide (FIGS. 11A, 11B). Structural homology between these STEAP-1 and STEAP-2 is highest in the regions spanned by the first putative extracellular loop to the fifth transmembrane domain. However, some significant structural differences between STEAP-1 and STEAP-2 are apparent. For example, STEAP-2 exhibits a 205 a.a. long intracellular N-terminus (compared to 69 a.a. in STEAP-1) and a short 4 a.a. intracellular C-terminus (compared to 26 a.a. in STEAP-1). In addition, both the STEAP-1 and STEAP-2 genes are located on chromosome 7, but on different arms. These differences could imply significant differences in function and/or interaction with intracellular signaling pathways.

STEAP-2 is expressed only in normal prostate among human tissues tested (FIGS. 14 and 15) and is also expressed in prostate cancer (FIG. 15), and thus shows some similarity in expression profile to STEAP-1. However, STEAP-2 exhibits a different mRNA expression profile relative to STEAP-1 in prostate cancer samples (compare FIGS. 3 and 15) and in other non-prostate cancers tested (compare FIGS. 5 and 16). These differences in the expression profiles of STEAP-1 and STEAP-2 suggest that they are differentially regulated.

STEAP-3 and STEAP-4 appear to be closely related to both STEAP-1 and STEAP-2 on a structural level, and both appear to be transmembrane proteins as well. STEAP-3 is more related to STEAP-2 (47.8% identity) than to STEAP-1 (40.9% identity). STEAP-3 and STEAP-4 show unique expression profiles. STEAP-3, for example, appears to have an expression pattern which is predominantly restricted to placenta and, to a smaller degree, expression is seen in prostate but not in other normal tissues tested. STEAP-4 seems to be expressed predominantly in liver by RT-PCR analysis. Neither STEAP-3 nor STEAP-4 appear to be expressed in prostate cancer xenografts which exhibit high level STEAP-1 and STEAP-2 expression.

Three of the four STEAPs described herein map to human chromosome 7 (STEAP-1, -2 and 3). Interestingly, STEAP-1 maps within 7p22 (7p22.3), a large region of allelic gain reported for both primary and recurrent prostate cancers (Visakorpi et al., 1995 Cancer Res. 55: 342, Nupponen et al., 1998 American J. Pathol. 153: 141), suggesting that up-regulation of STEAP-1 in cancer might include genomic mechanisms. In addition, both STEAP-2 and STEAP-3 locate to chromosome 7q21, suggesting that these two genes arose by gene duplication.

The function of the STEAPs are not known. Other cell surface molecules that contain six transmembrane domains include ion channels (Dolly and Parcej, 1996 J. Bioenerg Biomembr 28:231) and water channels or aquaporins (Reizer et al., 1993 Crit Rev Biochem Mol Biol 28:235). Structural studies show that both types of molecules assemble into tetrameric complexes to form functional channels (Christie, 1995, Clin Exp Pharmacol Physiol 22:944, Walz et al., 1997 Nature 387:624, Cheng et al., 1997 Nature 387:627). Immunohistochemical staining of STEAP-1 in the prostate gland seems to be concentrated at the cell-cell boundaries, with less staining detected at the luminal side. This may suggest a role for STEAP-1 in tight-junctions, gap-junctions or cell communication and adhesion. In order to test these possibilities, xenopus oocytes (or other cells) expressing STEAP may be analyzed using voltage-clamp and patch-clamp experiments to determine if STEAP functions as an ion-channel. Oocyte cell volume may also be measured to determine if STEAP exhibits water channel properties. If STEAPs function as channel or gap-junction proteins, they may serve as excellent targets for inhibition using, for example, antibodies, small molecules, and polynucleotides capable of inhibiting expression or function. The restricted expression pattern in normal tissue, and the high levels of expression in cancer tissue suggest that interfering with STEAP function may selectively kill cancer cells.

Since the STEAP gene family is predominantly expressed in epithelial tissue, it seems possible that the STEAP proteins function as ion channels, transport proteins or gap-junction proteins in epithelial cell function. Ion channels have been implicated in proliferation and invasiveness of prostate cancer cells (Lalani et al., 1997, Cancer Metastasis Rev 16:29). Both rat and human prostate cancer cells contain sub-population of cells with higher and lower expression levels of sodium channels. Higher levels of sodium channel expression correlate with more aggressive invasiveness in vitro (Smith et al., 1998, FEBS Lett. 423:19). Similarly, it has been shown that a specific blockade of sodium channels inhibits the invasiveness of PC-3 cells in vitro (Laniado et al., 1997, Am. J. Pathol. 150:1213), while specific inhibition of potassium channels in LNCaP cells inhibited cell proliferation (Skryma et al., 1997, Prostate 33:112). These reports suggest a role for ion channels in prostate cancer and also demonstrate that small molecules that inhibit ion channel function may interfere with prostate cancer proliferation.

STEAP Polynucleotides

One aspect of the invention provides polynucleotides corresponding or complementary to all or part of a STEAP gene, mRNA, and/or coding sequence, preferably in isolated form, including polynucleotides encoding a STEAP protein and fragments thereof, DNA, RNA, DNA/RNA hybrid, and related molecules, polynucleotides or oligonucleotides complementary to a STEAP gene or mRNA sequence or a part thereof, and polynucleotides or oligonucleotides which hybridize to a STEAP gene, mRNA, or to a STEAP-encoding polynucleotide (collectively, "STEAP polynucleotides"). As used herein, STEAP genes and proteins are meant to include the STEAP-1, STEAP-2 and STEAP-3 genes and proteins, and the gene and protein corresponding to GeneBank Accession number R80991 (STEAP-4), and the genes and proteins corresponding to other STEAP proteins and structurally similar variants of the foregoing. Such other STEAP proteins and variants will generally have coding sequences which are highly homologous to the STEAP coding sequences provided herein, and preferably will share at least about 50% amino acid identity and at least about 60% amino acid homology (using BLAST criteria), more preferably sharing 70% or greater homology (using BLAST criteria).

The STEAP family member gene sequences described herein encode STEAP proteins sharing unique highly conserved amino acid sequence domains which distinguish them from other proteins. Proteins which include one or more of these unique highly conserved domains may be related to the STEAP family members or may represent new STEAP proteins. Referring to FIG. 11A, which is an amino acid sequence alignment of the full STEAP-1, STEAP-2, and STEAP-3 protein sequences as well as the partial STEAP-4 sequence, it is clear that the STEAPs are closely related at the structural level. Referring to FIG. 11B, which is an amino acid sequence alignment of the full STEAP-1 and STEAP-2 protein sequences, close structural conservation is apparent, particularly in the predicted transmembrane domains. The STEAP-1 and STEAP-2 sequences share 54.9% identity over a 237 amino acid overlap. Additional amino acid sequence alignments between the STEAPs are shown in FIGS. 11C and 11D. These alignments show that STEAP-1 and STEAP-3 are 40.9% identical over a 264 amino acid region, while STEAP-2 and STEAP-3 are 47.8% identical over a 416 amino acid region. A STEAP polynucleotide may comprise a polynucleotide having the nucleotide sequence of human STEAP-1 as shown in FIG. 1A, the nucleotide sequence of human STEAP-2 as shown in FIG. 9, the nucleotide sequence of human STEAP-3 as shown in FIG. 10A, or the nucleotide sequence of STEAP-4 as shown in FIG. 10B, or a sequence complementary thereto, or a polynucleotide fragment of any of the foregoing. Another embodiment comprises a polynucleotide which encodes the human STEAP-1, STEAP-2, STEAP-3 or STEAP-4 protein amino acid sequences, a sequence complementary thereto, or a polynucleotide fragment of any of the foregoing. Another embodiment comprises a polynucleotide which is capable of hybridizing under stringent hybridization conditions to the human STEAP-1 cDNA shown in FIG. 1A, the human STEAP-2 cDNA shown in FIG. 9, the human STEAP-3 cDNA shown in FIG. 10A, or the STEAP-4 as shown in FIG. 10B, or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. The skilled person can readily obtain these classes of nucleic add molecules using the STEAP polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a STEAP polynucleotide in a sample and as a means for detecting a cell expressing a STEAP protein. Examples of such probes include polynucleotides comprising all or part of the human STEAP-1, STEAP-2 and STEAP-3 cDNA sequences shown in FIGS. 1A, 9 and 10A, respectively. Examples of primer pairs capable of specifically amplifying STEAP mRNAs are also described in the Examples which follow. As will be understood by the skilled person, a great many different primers and probes may be prepared based on the sequences provided in herein and used effectively to amplify and/or detect a STEAP mRNA or an mRNA encoding a particular STEAP family member.

As used herein, a polynucleotide is said to be "isolated" when it is substantially separated from contaminant polynucleotides which correspond or are complementary to genes other than the STEAP gene from which the polynucleotide is derived or which encode polypeptides other than the corresponding STEAP gene product or fragment thereof. The skilled person can readily employ nucleic acid isolation procedures to obtain an isolated STEAP polynucleotides.

The STEAP polynucleotides of the invention are useful for a variety of purposes, including but not limited to their use as probes and primers for the amplification and/or detection of the STEAP gene(s), mRNA(s), or fragments thereof; as reagents for the diagnosis and/or prognosis of prostate cancer and other cancers; as coding sequences capable of directing the expression of STEAP polypeptides; as tools for modulating or inhibiting the expression of the STEAP gene(s) and/or translation of the STEAP transcript(s); and as therapeutic agents.

Methods for Isolating STEAP-Encoding Nucleic Acid Molecules

The STEAP cDNA sequences described herein enable the isolation of other polynucleotides encoding STEAP gene product(s), as well as the isolation of polynucleotides encoding STEAP gene product homologues, alternatively spliced isoforms, allelic variants, and mutant forms of the STEAP gene product. Various molecular cloning methods that can be employed to isolate full length cDNAs encoding a STEAP gene are well known (See, for example, Sambrook, J. et al., Molecular Cloning: A Laboratory Manual, 2d edition., Cold Spring Harbor Press, N.Y., 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing STEAP gene cDNAs may be identified by probing with a labeled STEAP cDNA or a fragment thereof. For example, in one embodiment, the STEAP-1 cDNA (FIG. 1A) or a portion thereof can be synthesized and used as a probe to retrieve overlapping and full length cDNAs corresponding to a STEAP gene. Similarly, the STEAP-2 and STEAP-3 cDNA sequences may be employed. A STEAP gene may be isolated by screening genomic DNA libraries, bacterial artificial chromosome libraries (BACs), yeast artificial chromosome libraries (YACs), and the like, with STEAP DNA probes or primers.

Recombinant DNA Molecules and Host-Vector Systems

The invention also provides recombinant DNA or RNA molecules containing a STEAP polynucleotide, including but not limited to phages, plasmids, phagemids, cosmids, YACS, BACS, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a STEAP polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a STEAP may be used to generate STEAP proteins or fragments thereof using any number of host-vector systems routinely used and widely known in the art.

A wide range of host-vector systems suitable for the expression of STEAP proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, STEAP may be preferably expressed in several prostate cancer and non-prostate cell lines, including for example 293, 293T, rat-1, 3T3, PC-3, LNCaP and TsuPr1. The host-vector systems of the invention are useful for the production of a STEAP protein or fragment thereof. Such host-vector systems may be employed to study the functional properties of STEAP and STEAP mutations.

Proteins encoded by the STEAP genes, or by fragments thereof, will have a variety of uses, including but not limited to generating antibodies and in methods for identifying ligands and other agents and cellular constituents that bind to a STEAP gene product. Antibodies raised against a STEAP protein or fragment thereof may be useful in diagnostic and prognostic assays, imaging methodologies (including, particularly, cancer imaging), and therapeutic methods in the management of human cancers characterized by expression of a STEAP protein, such as prostate, colon, breast, cervical and bladder carcinomas, ovarian cancers, testicular cancers and pancreatic cancers. Various immunological assays useful for the detection of STEAP proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). STEAP proteins may also be particularly useful in generating cancer vaccines, as further described below.

STEAP Proteins

Another aspect of the present invention provides various STEAP proteins and polypeptide fragments thereof. As used herein, a STEAP protein refers to a protein that has or includes the amino add sequence of human STEAP-1 as provided in FIG. 1A, human STEAP-2 as provided in FIG. 9, human STEAP-3 as provided in FIG. 10A, the amino acid sequence of other mammalian STEAP homologues (e.g., STEAP-4) and variants, as well as allelic variants and conservative substitution mutants of these proteins that have STEAP biological activity.

The STEAP proteins of the invention include those specifically identified herein, as well as allelic variants, conservative substitution variants and homologs that can be isolated/generated and characterized without undue experimentation following the methods outlined below. Fusion proteins which combine parts of different STEAP proteins or fragments thereof, as well as fusion proteins of a STEAP protein and a heterologous polypeptide are also included. Such STEAP proteins will be collectively referred to as the STEAP proteins, the proteins of the invention, or STEAP. As used herein, the term "STEAP polypeptide" refers to a polypeptide fragment or a STEAP protein of at least 8 amino adds, preferably at least 10 amino acids.

A specific embodiment of a STEAP protein comprises a polypeptide having the amino add sequence of human STEAP-1 as shown in FIG. 1A. Another embodiment of a STEAP protein comprises a polypeptide containing the STEAP-2 amino acid sequence as shown in FIG. 9. Another embodiment comprises a polypeptide containing the STEAP-3 amino acid sequence of shown in FIG. 10A. Yet another embodiment comprises a polypeptide containing the partial STEAP-4 amino add sequence of shown in FIG. 11A.

In general, naturally occurring allelic variants of individual human STEAPs will share a high degree of structural identity and homology (e.g., 90% or more identity). Typically, allelic variants of the STEAP proteins will contain conservative amino add substitutions within the STEAP sequences described herein or will contain a substitution of an amino add from a corresponding position in a STEAP homologue. One class of STEAP allelic variants will be proteins that share a high degree of homology with at least a small region of a particular STEAP amino add sequence, but will further contain a radical departure form the sequence, such as a non-conservative substitution, truncation, insertion or frame shift. Such alleles may represent mutant STEAP proteins that typically do not perform the same biological functions or do not have all of the biological characteristics.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic add (D) for glutamic acid (E) and vice versa; glutamine (Q) for asparagine (N) and vice versa; and seine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

STEAP proteins may be embodied in many forms, preferably in isolated form. As used herein, a protein is said to be "isolated" when physical, mechanical or chemical methods are employed to remove the STEAP protein from cellular constituents that are normally associated with the protein. A skilled artisan can readily employ standard purification methods to obtain an isolated STEAP protein. A purified STEAP protein molecule will be substantially free of other proteins or molecules which impair the binding of STEAP to antibody or other ligand. The nature and degree of isolation and purification will depend on the intended use. Embodiments of a STEAP protein include a purified STEAP protein and a functional, soluble STEAP protein. In one form, such functional, soluble STEAP proteins or fragments thereof retain the ability to bind antibody or other ligand.

The invention also provides STEAP polypeptides comprising biologically active fragments of the STEAP amino acid sequence, such as a polypeptide corresponding to part of the amino acid sequences for STEAP-1 as shown in FIG. 1A, STEAP-2 as shown in FIG. 9, STEAP-3 as shown in FIG. 10A, or STEAP-4 as shown in FIG. 11A. Such polypeptides of the invention exhibit properties of a STEAP protein, such as the ability to elicit the generation of antibodies which specifically bind an epitope associated with a STEAP protein. Polypeptides comprising amino acid sequences which are unique to a particular STEAP protein (relative to other STEAP proteins) may be used to generate antibodies which will specifically react with that particular STEAP protein. For example, referring to the amino add alignment of the STEAP structures shown in FIGS. 11A-D, the skilled artisan will readily appreciate that each molecule contains stretches of sequence unique to its structure. These unique stretches can be used to generate antibodies specific to a particular STEAP. Similarly, regions of conserved sequence may be used to generate antibodies that may bind to multiple STEAPs.

STEAP polypeptides can be generated using standard peptide synthesis technology or using chemical cleavage methods well known in the art based on the amino add sequences of the human STEAP proteins disclosed herein. Alternatively, recombinant methods can be used to generate nucleic acid molecules that encode a polypeptide fragment of a STEAP protein. In this regard, the STEAP-encoding nucleic add molecules described herein provide means for generating defined polypeptide fragments of STEAP proteins. Such STEAP polypeptides or peptides are particularly useful for generating and characterizing domain specific antibodies (e.g., antibodies recognizing an extracellular or intracellular epitope of a STEAP protein), generating STEAP family member specific antibodies (e.g., anti-STEAP-1, anti-STEAP 2 antibodies), identifying agents or cellular factors that bind to a particular STEAP or STEAP domain, and in various therapeutic contexts, including but not limited to cancer vaccines. STEAP polypeptides containing particularly interesting structures can be predicted and/or identified using various analytical techniques well known in the art, including, for example, the methods of Chou-Fasman, Gamier-Robson, Kyte-Doolittle, Eisenberg, Karplus-Schultz or Jameson-Wolf analysis, or on the basis of immunogenicity. Fragments containing such structures are particularly useful in generating subunit specific anti-STEAP antibodies or in identifying cellular factors that bind to STEAP.

STEAP Antibodies

Another aspect of the invention provides antibodies that bind to STEAP proteins and polypeptides. The most preferred antibodies will specifically bind to a STEAP protein and will not bind (or will bind weakly) to non-STEAP proteins and polypeptides. Anti-STEAP antibodies that are particularly contemplated include monodonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

For some applications, it may be desirable to generate antibodies which specifically react with a particular STEAP protein and/or an epitope within a particular structural domain. For example, preferred antibodies useful for cancer therapy and diagnostic imaging purposes are those which react with an epitope in an extracellular region of the STEAP protein as expressed in cancer cells. Such antibodies may be generated by using the STEAP proteins described herein, or using peptides derived from predicted extracellular domains thereof, as an immunogen. In this regard, with reference to the STEAP-1 protein topological schematic shown in FIG. 1B, regions in the extracellular loops between the indicated transmembrane domains may be selected as used to design appropriate immunogens for raising extracellular-specific antibodies.

STEAP antibodies of the invention may be particularly useful in prostate cancer therapeutic strategies, diagnostic and prognostic assays, and imaging methodologies. The invention provides various immunological assays useful for the detection and quantification of STEAP and mutant STEAP proteins and polypeptides. Such assays generally comprise one or more STEAP antibodies capable of recognizing and binding a STEAP or mutant STEAP protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled STEAP antibodies. Such assays may be clinically useful in the detection, monitoring, and prognosis of prostate cancer, particularly advanced prostate cancer.

The invention also provides various immunological assays useful for the detection and quantification of STEAP and mutant STEAP proteins and polypeptides. Such assays generally comprise one or more STEAP antibodies capable of recognizing and binding a STEAP or mutant STEAP protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing STEAP (e.g., breast cancer) are also provided by the invention, including but limited to radioscintigraphic imaging methods using labeled STEAP antibodies. Such assays may be clinically useful in the detection, monitoring, and prognosis of STEAP expressing cancers such as prostate cancer.

STEAP antibodies may also be used in methods for purifying STEAP and mutant STEAP proteins and polypeptides and for isolating STEAP homologues and related molecules. For example, in one embodiment, the method of purifying a STEAP protein comprises incubating a STEAP antibody, which has been coupled to a solid matrix, with a lysate or other solution containing STEAP under conditions which permit the STEAP antibody to bind to STEAP; washing the solid matrix to eliminate impurities; and eluting the STEAP from the coupled antibody. Other uses of the STEAP antibodies of the invention include generating anti-idiotypic antibodies that mimic the STEAP protein.

Various methods for the preparation of antibodies are well known in the art. For example, antibodies may be prepared by immunizing a suitable mammalian host using a STEAP protein, peptide, or fragment, in isolated or immunoconjugated form (Antibodies: A Laboratory Manual, CSH Press, Eds., Harlow, and Lane (1988); Harlow, Antibodies, Cold Spring Harbor Press, N.Y. (1989)). In addition, fusion proteins of STEAP may also be used, such as a STEAP GST-fusion protein. In a particular embodiment, a GST fusion protein comprising all or most of the open reading frame amino acid sequence of a STEAP may be produced and used as an immunogen to generate appropriate antibodies. In another embodiment, a STEAP peptide may be synthesized and used as an immunogen. As described in Example 5, below, the 15-mer STEAP peptide HSSKEKLRRERIKYC (SEQ ID NO: 46) was conjugated to keyhole limpet hemocyanin (KLH) and used to immunize a rabbit. The resulting polyclonal antiserum specifically recognized STEAP expressed in a recombinant mammalian expression system.

In addition, naked DNA immunization techniques known in the art may be used (with or without purified STEAP protein or STEAP expressing cells) to generate an immune response to the encoded immunogen (for review, see Donnelly et al., 1997, Ann. Rev. Immunol. 15: 617-648).

The amino acid sequences of the STEAPs provided herein may be used to select specific regions of the STEAP protein for generating antibodies. For example, hydrophobicity and hydrophilicity analyses of the STEAP amino acid sequence may be used to identify hydrophilic regions in the STEAP structure. Regions of the STEAP protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Methods for the generation of STEAP antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a STEAP immunogen is conducted generally by injection over a suitable time period and with use of a suitable adjuvant, as is generally understood in the art. During the immunization schedule, titers of antibodies can be taken to determine adequacy of antibody formation.

STEAP monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, as is generally known. The immortalized cell lines secreting the desired antibodies are screened by immunoassay in which the antigen is the STEAP protein or a STEAP fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the STEAP protein can also be produced in the context of chimeric or CDR grafted antibodies of multiple species origin. Humanized or human STEAP antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmnan et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, 3. Immunol. 151:2296. Methods for producing fully human monoclonal antibodies include phage display and transgenic methods (for review, see Vaughan et al., 1998, Nature Biotechnology 16: 535-539).

Fully human STEAP monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human STEAP monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of STEAP antibodies with a STEAP protein may be established by a number of well known means, including Western blot, immunoprecipitation, ELISA, and FACS analyses using, as appropriate, STEAP proteins, peptides, STEAP-expressing cells or extracts thereof.

A STEAP antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more STEAP epitopes may be generated using methods generally known in the art. Homodimeric antibodies may also be generated by cross-linking techniques known in the art (e.g., Wolff et al., Cancer Res. 53: 2560-2565).

Methods for the Detection of STEAP

Another aspect of the present invention relates to methods for detecting STEAP polynucleotides and STEAP proteins, as well as methods for identifying a cell which expresses STEAP.

More particularly, the invention provides assays for the detection of STEAP polynucleotides in a biological sample, such as serum, bone, prostate, and other tissues, urine, semen, cell preparations, and the like. Detectable STEAP polynucleotides include, for example, a STEAP gene or fragments thereof, STEAP mRNA, alternative splice variant STEAP mRNAs, and recombinant DNA or RNA molecules containing a STEAP polynucleotide. A number of methods for amplifying and/or detecting the presence of STEAP polynucleotides are well known in the art and may be employed in the practice of this aspect of the invention.

In one embodiment, a method for detecting a STEAP mRNA in a biological sample comprises producing cDNA from the sample by reverse transcription using at least one primer; amplifying the cDNA so produced using a STEAP polynucleotides as sense and antisense primers to amplify STEAP cDNAs therein; and detecting the presence of the amplified STEAP cDNA. In another embodiment, a method of detecting a STEAP gene in a biological sample comprises first isolating genomic DNA from the sample; amplifying the isolated genomic DNA using STEAP polynucleotides as sense and antisense primers to amplify the STEAP gene therein; and detecting the presence of the amplified STEAP gene. Any number of appropriate sense and antisense probe combinations may be designed from the nucleotide sequences provided for STEAP-1 (FIG. 1A), STEAP-2 (FIG. 9), STEAP-3 (FIG. 10A), or STEAP-4 (FIG. 10B), as appropriate, and used for this purpose.

The invention also provides assays for detecting the presence of a STEAP protein in a tissue of other biological sample such as serum, bone, prostate, and other tissues, urine, cell preparations, and the like. Methods for detecting a STEAP protein are also well known and include, for example, immunoprecipitation, immunohistochemical analysis, Western Blot analysis, molecular binding assays, ELISA, ELIFA and the like.

For example, in one embodiment, a method of detecting the presence of a STEAP protein in a biological sample comprises first contacting the sample with a STEAP antibody, a STEAP-reactive fragment thereof, or a recombinant protein containing an antigen binding region of a STEAP antibody; and then detecting the binding of STEAP protein in the sample thereto.

Methods for identifying a cell which expresses STEAP are also provided. In one embodiment, an assay for identifying a cell which expresses a STEAP gene comprises detecting the presence of STEAP mRNA in the cell. Methods for the detection of particular mRNAs in cells are well known and include, for example, hybridization assays using complementary DNA probes (such as in situ hybridization using labeled STEAP riboprobes, Northern blot and related techniques) and various nucleic acid amplification assays (such as RT-PCR using complementary primers specific for STEAP, and other amplification type detection methods, such as, for example, branched DNA, SISBA, TMA and the like). Alternatively, an assay for identifying a cell which expresses a STEAP gene comprises detecting the presence of STEAP protein in the cell or secreted by the cell. Various methods for the detection of proteins are well known in the art and may be employed for the detection of STEAP proteins and STEAP expressing cells.

STEAP expression analysis may also be useful as a tool for identifying and evaluating agents which modulate STEAP gene expression. For example, STEAP-1 expression is significantly upregulated in colon, bladder, pancreatic, ovarian and other cancers. Identification of a molecule or biological agent that could inhibit STEAP-1 over-expression may be of therapeutic value in the treatment of cancer. Such an agent may be identified by using a screen that quantifies STEAP expression by RT-PCR, nucleic acid hybridization or antibody binding.

Assays for Determining STEAP Expression Status

Determining the status of STEAP expression patterns in an individual may be used to diagnose cancer and may provide prognostic information useful in defining appropriate therapeutic options. Similarly, the expression status of STEAP may provide information useful for predicting susceptibility to particular disease stages, progression, and/or tumor aggressiveness. The invention provides methods and assays for determining STEAP expression status and diagnosing cancers which express STEAP.

In one aspect, the invention provides assays useful in determining the presence of cancer in an individual, comprising detecting a significant increase in STEAP mRNA or protein expression in a test cell or tissue sample relative to expression levels in the corresponding normal cell or tissue. In one embodiment, the presence of STEAP-1 mRNA is evaluated in tissue samples of the colon, pancreas, bladder, ovary, cervix, testis or breast. The presence of significant STEAP-1 expression in any of these tissues may be useful to indicate the emergence, presence and/or severity of these cancers, since the corresponding normal tissues do not express STEAP-1 mRNA. In a related embodiment, STEAP-1 expression status may be determined at the protein level rather than at the nucleic add level. For example, such a method or assay would comprise determining the level of STEAP-1 protein expressed by cells in a test tissue sample and comparing the level so determined to the level of STEAP expressed in a corresponding normal sample. In one embodiment, the presence of STEAP-1 protein is evaluated, for example, using immunohistochemical methods. STEAP antibodies or binding partners capable of detecting STEAP protein expression may be used in a variety of assay formats well known in the art for this purpose.

Peripheral blood may be conveniently assayed for the presence of cancer cells, including prostate, colon, pancreatic, bladder and ovarian cancers, using RT-PCR to detect STEAP-1 expression. The presence of RT-PCR amplifiable STEAP-1 mRNA provides an indication of the presence of one of these types of cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

In another approach, a recently described sensitive assay for detecting and characterizing carcinoma cells in blood may be used (Racila et al., 1998, Proc. Natl. Acad. Sci. USA 95: 4589-4594). This assay combines immunomagnetic enrichment with multiparameter flow cytometric and immunohistochemical analyses, and is highly sensitive for the detection of cancer cells in blood, reportedly capable of detecting one epithelial cell in 1 ml of peripheral blood.

A related aspect of the invention is directed to predicting susceptibility to developing cancer in an individual. In one embodiment, a method for predicting susceptibility to cancer comprises detecting STEAP mRNA or STEAP protein in a tissue sample, its presence indicating susceptibility to cancer, wherein the degree of STEAP mRNA expression present is proportional to the degree of susceptibility.

Yet another related aspect of the invention is directed to methods for gauging tumor aggressiveness. In one embodiment, a method for gauging aggressiveness of a tumor comprises determining the level of STEAP mRNA or STEAP protein expressed by cells in a sample of the tumor, comparing the level so determined to the level of STEAP mRNA or STEAP protein expressed in a corresponding normal tissue taken from the same individual or a normal tissue reference sample, wherein the degree of STEAP mRNA or STEAP protein expression in the tumor sample relative to the normal sample indicates the degree of aggressiveness.

Methods for detecting and quantifying the expression of STEAP mRNA or protein are described herein and use standard nucleic add and protein detection and quantification technologies well known in the art. Standard methods for the detection and quantification of STEAP mRNA include in situ hybridization using labeled STEAP riboprobes, Northern blot and related techniques using STEAP polynucleotide probes, RT-PCR analysis using primers specific for STEAP, and other amplification type detection methods, such as, for example, branched DNA, SISBA, TMA and the like. In a specific embodiment, semi-quantitative RT-PCR may be used to detect and quantify STEAP mRNA expression as described in the Examples which follow. Any number of primers capable of amplifying STEAP may be used for this purpose, including but not limited to the various primer sets specifically described herein. Standard methods for the detection and quantification of protein may be used for this purpose. In a specific embodiment, polyclonal or monoclonal antibodies specifically reactive with the wild-type STEAP protein may be used in an immunohistochemical assay of biopsied tissue.

Diagnostic Imaging of Human Cancers

Antibodies specific for STEAPs may be particularly useful in radionuclide and other forms of diagnostic imaging of certain cancers, given their expression profiles and cell surface location. For example, immunohistochemical analysis of STEAP-1 protein suggests that in normal tissues STEAP-1 is predominantly restricted to prostate and bladder. The transmembrane orientation of STEAP-1 (and presumably STEAP-2, STEAP-3, STEAP-4) provides a target readily identifiable by antibodies specifically reactive with extracellular epitopes. This tissue restricted expression, and the localization of STEAP to the cell surface of multiple cancers makes STEAP an ideal candidate for diagnostic imaging. Accordingly, in vivo imaging techniques may be used to image human cancers expressing a STEAP protein.

For example, cell surface STEAP-1 protein is expressed at very high levels in several human cancers, particularly prostate, bladder, colon and ovarian cancers, and Ewing sarcoma. Moreover, in normal tissues, STEAP-1 protein expression is largely restricted to prostate. Thus, radiolabeled antibodies specifically reactive with extracellular epitopes of STEAP-1 may be particularly useful in vivo imaging of solid tumors of the foregoing cancers. Such labeled anti-STEAP-1 antibodies may provide very high level sensitivities for the detection of metastasis of these cancers.

Preferably, monoclonal antibodies are used in the diagnostic imaging methods of the invention.

Cancer Immunotherapy and Cancer Vaccines

The invention provides various immunotherapeutic methods for treating prostate cancer, including antibody therapy, in vivo vaccines, and ex vivo immunotherapy methods, which utilize polynucleotides and polypeptides corresponding to STEAP and STEAP antibodies. These therapeutic applications are described further in the following subsections.

Antibody Therapy

The cell surface nature and expression profiles of the STEAPs in cancers including prostate cancer indicate that they are promising targets for antibody therapy of prostate and other cancers expressing STEAPs. The experimental results described in the Examples herein provide compelling evidence that STEAP-1 is strongly expressed uniformly over the surface of glandular epithelial cells within prostate and prostate cancer cells. In particular, immunohistochemical analysis results show that the surface of human prostate epithelial cells (normal and cancer) appear to be uniformly coated with STEAP-1. Biochemical analysis confirms the cell surface localization of STEAP-1 initially suggested by its putative 6-transmembrane primary structural elements and by the pericellular staining plainly visualized by immunohistochemical staining.

STEAP-1 is uniformly expressed at high levels over the surface of prostate glandular epithelia, an ideal situation for immunotherapeutic intervention strategies which target extracellular STEAP epitopes. Systemic administration of STEAP-immunoreactive compositions would be expected to result in extensive contact of the composition with prostate epithelial cells via binding to STEAP-1 extracellular epitopes. Moreover, given the near absence of STEAP-1 protein expression in normal human tissues, there is ample reason to expect exquisite sensitivity without toxic, non-specific and/or non-target effects caused by the binding of the immunotherapeutic composition to STEAP-1 on non-target organs and tissues.

In addition to the high level expression of STEAP-1 in prostate and prostate cancer cells, STEAP-1 appears to be substantially over-expressed in a variety of other human cancers, including bladder, colon, pancreatic and ovarian cancers. In particular, high level STEAP-1 mRNA expression is detected in all tested prostate cancer tissues and cell lines, and in most of the pancreatic, colon, and bladder cancer cell lines tested. High level expression of STEAP-1 is also observed in some ovarian cancer cell lines. Lower level expression is observed in some breast, testicular, and cervical cancer cell lines. Very high level expression is also detected in a Ewing sarcoma cell line. Applicants have shown that cell surface STEAP-1 protein is expressed in bladder and colon cancers, while there is no detectable cell surface (or intracellular) STEAP-1 protein in normal colon and low expression in normal bladder. Antibodies specifically reactive with extracellular domains of STEAP-1 may be useful to treat these cancers systemically, either as toxin or therapeutic agent conjugates or as naked antibodies capable of inhibiting cell proliferation or function.

STEAP-2 protein is also expressed in prostate cancer, and may be expressed in other cancers as well. STEAP-2 mRNA analysis by RT-PCR and Northern blot show that expression is restricted to prostate in normal tissues, is also expressed in some prostate, pancreatic, colon, testicular, ovarian and other cancers. Therefore, antibodies reactive with STEAP-2 may be useful in the treatment of prostate and other cancers. Similarly, although not yet characterized by applicants, the expression of STEAP-3 and STEAP-4 (as well as other STEAPs) may be associated with some cancers. Thus antibodies reactive with these STEAP family member proteins may also be useful therapeutically.

STEAP antibodies may be introduced into a patient such that the antibody binds to STEAP on the cancer cells and mediates the destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiologic function of STEAP, inhibiting ligand binding or signal transduction pathways, modulating tumor cell differentiation, altering tumor angiogenesis factor profiles, and/or by inducing apoptosis. STEAP antibodies conjugated to toxic or therapeutic agents may also be used therapeutically to deliver the toxic or therapeutic agent directly to STEAP-bearing tumor cells.

Cancer therapy using anti-STEAP antibodies may follow the teachings generated from various approaches which have been successfully employed with respect to other types of cancer, including but not limited to colon cancer (Arlen et al., 1998, Crit Rev Immunol 18: 133-138), multiple myeloma (Ozaki et al., 1997, Blood 90: 3179-3186; Tsunenari et al., 1997, Blood 90: 2437-2444), gastric cancer (Kasprzyk et al., 1992, Cancer Res 52: 2771-2776), B-cell lymphoma (Funakoshi et al., 1996, J Immunther Emphasis Tumor Immunol 19: 93-101), leukemia (Zhong et al., 1996, Leuk Res 20: 581-589), colorectal cancer (Moun et al., 1994, Cancer Res 54: 6160-6166); Velders et al., 1995, Cancer Res 55: 4398-4403), and breast cancer (Shepard et al., 1991, J Clin Immunol 11:117-127).

Although STEAP antibody therapy may be useful for all stages of the foregoing cancers, antibody therapy may be particularly appropriate and in advanced or metastatic cancers. Combining the antibody therapy method of the invention with a chemotherapeutic or radiation regimen may be preferred in patients who have not received chemotherapeutic treatment, whereas treatment with the antibody therapy of the invention may be indicated for patients who have received one or more chemotherapy. Additionally, antibody therapy may also enable the use of reduced dosages of concomitant chemotherapy, particularly in patients that do not tolerate the toxicity of the chemotherapeutic agent very well.

It may be desirable for non-prostate cancer patients to be evaluated for the presence and level of STEAP over-expression, preferably using immunohistochemical assessments of tumor tissue, quantitative STEAP imaging, or other techniques capable of reliably indicating the presence and degree of STEAP overexpression. Immunohistochemical analysis of tumor biopsies or surgical specimens may be preferred for this purpose. Methods for immunohistochemical analysis of tumor tissues are well known in the art.

Anti-STEAP monodonal antibodies useful in treating prostate and other cancers include those which are capable of initiating a potent immune response against the tumor and those which are capable of direct cytotoxicity. In this regard, anti-STEAP mAbs may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-STEAP mAbs which exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-STEAP mAb exerts an anti-tumor effect may be evaluated using any number of in vitro assays designed to determine ADCC, ADMMC, complement-mediated cell lysis, and so forth, as is generally known in the art.

The anti-tumor activity of a particular anti-STEAP mAb, or combination of anti-STEAP mAbs, may be evaluated in vivo using a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402-408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays which measure inhibition of tumor formation, tumor regression or metastasis, and the like.

It should be noted that the use of murine or other non-human monoclonal antibodies, human/mouse chimeric mAbs may induce moderate to strong immune responses in some patients. In the most severe cases, such an immune response may lead to the extensive formation of immune complexes which, potentially, can cause renal failure. Accordingly, preferred monodonal antibodies used in the practice of the therapeutic methods of the invention are those which are either fully human or humanized and which bind specifically to the target 20P1F12/TMPRSS2 antigen with high affinity but exhibit low or no antigenicity in the patient.

The method of the invention contemplates the administration of single anti-STEAP mAbs as well as combinations, or "cocktails, of different mAbs. Such mAb cocktails may have certain advantages inasmuch as they contain mAbs which exploit different effector mechanisms or combine directly cytotoxic mAbs with mAbs that rely on immune effector functionality. Such mAbs in combination may exhibit synergistic therapeutic effects. In addition, the administration of anti-STEAP mAbs may be combined with other therapeutic agents, including but not limited to various chemotherapeutic agents, androgen-blockers, and immune modulators (e.g., IL-2, GM-CSF). The anti-STEAP mAbs may be administered in their "naked" or unconjugated form, or may have therapeutic agents conjugated to them.

The anti-STEAP monoclonal antibodies used in the practice of the method of the invention may be formulated into pharmaceutical compositions comprising a carrier suitable for the desired delivery method. Suitable carriers include any material which when combined with the anti-STEAP mAbs retains the anti-tumor function of the antibody and is non-reactive with the subject's immune systems. Examples include, but are not limited to, any of a number of standard pharmaceutical carriers such as sterile phosphate buffered saline solutions, bacteriostatic water, and the like.

The anti-STEAP antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-STEAP mAbs in a solution of preserved bacteriostatic water, sterile unpreserved water, and/or diluted in polyvinylchloride or polyethylene bags containing 0.9% sterile Sodium Chloride for Injection, USP. The anti-STEAP mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-STEAP antibody preparation via an acceptable route of administration such as intravenous injection (IV), typically at a dose in the range of about 0.1 to about 10 mg/kg body weight. Doses in the range of 10-500 mg mAb per week may be effective and well tolerated. Based on clinical experience with the Herceptin-mAb in the treatment of metastatic breast cancer, an initial loading dose of approximately 4 mg/kg patient body weight IV followed by weekly doses of about 2 mg/kg IV of the anti-STEAP mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the mAb or mAbs used, the degree of STEAP overexpression in the patient, the extent of circulating shed STEAP antigen, the desired steady-state antibody concentration level, frequency of treatment, and the influence of chemotherapeutic agents used in combination with the treatment method of the invention.

Optimally, patients should be evaluated for the level of circulating shed STEAP antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Cancer Vaccines

The invention further provides prostate cancer vaccines comprising a STEAP protein or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231-237; Fong et al., 1997, J. Immunol. 159: 3113-3117). Such methods can be readily practiced by employing a STEAP protein, or fragment thereof, or a STEAP-encoding nucleic acid molecule and recombinant vectors capable of expressing and appropriately presenting the STEAP immunogen.

For example, viral gene delivery systems may be used to deliver a STEAP-encoding nucleic add molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a STEAP protein or fragment thereof introduced into the patient (e.g., intramuscularly) to induce an anti-tumor response. In one embodiment, the full-length human STEAP cDNA may be employed. In another embodiment, STEAP nucleic acid molecules encoding specific cytotoxic T lymphocyte (CTL) epitopes may be employed. CTL epitopes can be determined using specific algorithms (e.g., Epimer, Brown University) to identify peptides within a STEAP protein which are capable of optimally binding to specified HLA alleles. Optimally immunogenic HLA Class I molecule-binding peptides within the STEAP-1 and STEAP-2 sequences have been analyzed in Example 9, below.

Various ex vivo strategies may also be employed. One approach involves the use of dendritic cells to present STEAP antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65-69; Murphy et al., 1996, Prostate 29: 371-380). Dendritic cells can be used to present STEAP peptides to T cells in the context of MHC class I and II molecules. In one embodiment, autologous dendritic cells are pulsed with STEAP peptides capable of binding to MHC molecules. In another embodiment, dendritic cells are pulsed with the complete STEAP protein. Yet another embodiment involves engineering the overexpression of the STEAP gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182).

Anti-idiotypic anti-STEAP antibodies can also be used in anti-cancer therapy as a vaccine for inducing an immune response to cells expressing a STEAP protein. Specifically, the generation of anti-idiotypic antibodies is well known in the art and can readily be adapted to generate anti-idiotypic anti-STEAP antibodies that mimic an epitope on a STEAP protein (see, for example, Wagner et al., 1997, Hybridoma 16: 33-40; Foon et al., 1995, J Clin Invest 96: 334342; Hedyn et al., 1996, Cancer Immunol Immunother 43: 65-76). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing STEAP. Constructs comprising DNA encoding a STEAP protein/immunogen and appropriate regulatory sequences may be injected directly into muscle or skin of an individual, such that the cells of the muscle or skin take-up the construct and express the encoded STEAP protein/immunogen. Expression of the STEAP protein immunogen results in the generation of prophylactic or therapeutic humoral and cellular immunity against prostate cancer. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a STEAP protein or a STEAP gene or message, respectively. Where the kit utilizes nucleic acid hybridization to detect the target nucleic add, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

EXAMPLES

Various aspects of the invention are further described and illustrated by way of the several examples which follow, none of which are intended to limit the scope of the invention.

Example 1

Isolation of cDNA Fragment of STEAP-1 Gene

Materials and Methods

Cell lines and Human Tissues

All human cancer cell lines used in this study were obtained from the ATCC. All cell lines were maintained in DMEM with 10% fetal calf serum. PrEC (primary prostate epithelial cells) were obtained from Clonetics and were grown in PrEBM media supplemented with growth factors (Clonetics).

All human prostate cancer xenografts were originally provided by Charles Sawyers (UCLA) (Klein et al., 1997). LAPC-4 AD and LAPC-9 AD xenografts were routinely passaged as small tissue chunks in recipient SCID males. LAPC-4 AI and LAPC-9 AI xenografts were derived as described previously (Klein et al., 1997) and were passaged in castrated males or in female SCID mice. A benign prostatic hyperplasia tissue sample was patient-derived.

Human tissues for RNA and protein analyses were obtained from the Human Tissue Resource Center (HTRC) at the UCLA (Los Angeles, Calif.) and from QualTek, Inc. (Santa Barbara, Calif.).

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
RSACDN (cDNA synthesis primer):
5'TTTTGTACAAGCTT₃₀3'              (SEQ ID NO: 22)

Adaptor 1:
5'CTAATACGACTCACTATAGGGCTCGAGCG-  (SEQ ID NO: 23)
GCCGCCCGGGCAGGT3'

3'GGCCCGTCCA5'           (SEQ ID NO:24)

Adaptor 2:
5'GTAATACGACTCACTATAGGGCAGCGTG-   (SEQ ID NO: 25)
GTCGCGGCCGAGGT3'

3'CGGCTCCA5'             (SEQ ID NO: 26)

PCR primer 1:
5'CTAATACGACTCACTATAGGGC3'        (SEQ ID NO: 27)

Nested primer (NP)1:
5'TCGAGCGGCCGCCCGGGCAGGT3'        (SEQ ID NO: 28)

Nested primer (NP)2:
5'AGCGTGGTCGCGGCCGAGGT3'          (SEQ ID NO: 29)
```

Suppression Subtractive Hybridization:

Suppression Subtractive Hybridization (SSH) was used to identify cDNAs corresponding to genes which may be up-regulated in androgen dependent prostate cancer compared to benign prostatic hyperplasia.

Double stranded cDNAs corresponding to the LAPC-4 AD xenograft (tester) and the BPH tissue (driver) were synthesized from 2 μg of poly(A)⁺ RNA isolated from xenograft and BPH tissue, as described above, using CLONTECH's PCR-Select cDNA Subtraction Kit and 1 ng of oligonucleotide RSACDN as primer. First- and second-strand synthesis were carried out as described in the Kit's user manual protocol (CLONTECH Protocol No. PT1117-1, Catalog No. K1804-1). The resulting cDNA was digested with Rsa I for 3 hrs. at 37° C. Digested cDNA was extracted with phenol/chloroform (1:1) and ethanol precipitated.

Driver cDNA (BPH) was generated by combining in a 4 to 1 ratio Rsa I digested BPH cDNA with digested cDNA from mouse liver, in order to ensure that murine genes were subtracted from the tester cDNA (LAPC-4 AD).

Tester cDNA (LAPC-4 AD) was generated by diluting 1 μl of Rsa I digested LAPC-4 AD cDNA (400 ng) in 5 μl of water. The diluted cDNA (2 μl, 160 ng) was then ligated to 2 μl of adaptor 1 and adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) adaptor 1- and adaptor 2-ligated tester cDNA. In a final volume of 4 μl, the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5µl 10×reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic add homology searches of the GenBank, dBest, and NCI-CGAP databases.

RT-PCR Expression Analysis:

First strand cDNAs were generated from 1 µg of mRNA with oligo (dT)12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200µl with water prior to normalization. First strand cDNAs from 16 different normal human tissues were obtained from Clontech.

Normalization of the first strand cDNAs from multiple tissues was performed by using the primers 5'atatcgccgcgctcgtcgtcgacaa3' (SEQ ID NO: 31) and 5'agccacacgcagctcattgtagaagg 3' (SEQ ID NO: 32) to amplify β-actin. First strand cDNA (5 µl) was amplified in a total volume of 50 µl containing 0.4 µM primers, 0.2 µM each dNTPs, 1XPCR buffer (Clontech, 10 mM Tris-HCL, 1.5 mM $MgCl_2$, 50 mM KC1, pH8.3) and 1X Klentaq DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 8P1D4 gene, 5 µl of normalized first strand cDNA was analyzed by PCR using 25, 30, and 35 cycles of amplification using the following primer pairs:

5' ACT TTG TTG ATG ACC AGG ATT GGA 3'  (SEQ ID NO: 14)

5' CAG AAC TTC AGC ACA CAC AGG AAC 3'  (SEQ ID NO: 15)

Semi quantitative expression analysis was achieved by comparing the PCR products at cycle numbers that give light band intensities.

Results:

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the cDNA clones, designated 8P1D4, was 436 bp in length and showed homology to an EST sequence in the NCI-CGAP tumor gene database. The full length cDNA encoding the 8P1D4 gene was subsequently isolated using this cDNA and re-named STEAP-1. The 8P1D4 cDNA nucleotide sequence corresponds to nucleotide residues 150 through 585 in the STEAP-1 cDNA sequence as shown in FIG. 1A. Another clone, designated 28P3E1, 561 bp in length showed homology to a number of EST sequences in the NCI-CGAP tumor gene database or in other databases. Part of the 28P3E1 sequence (356 bp) is identical to an EST derived from human fetal tissue. After the full length STEAP-1 cDNA was obtained and sequenced, it became apparent that this clone also corresponds to STEAP-1 (more specifically, to residues 622 through the 3' end of the STEAP-1 nucleotide sequence as shown in FIG. 1A).

Differential expression analysis by RT-PCR using primers derived from the 8P1D4 cDNA clone showed that the 8P1D4 (STEAP-1) gene is expressed at approximately equal levels in normal prostate and the LAPC-4 and LAPC-9 xenografts (FIG. 2, panel A). Further RT-PCR expression analysis of first strand cDNAs from 16 normal tissues showed greatest levels of 8P1D4 expression in prostate. Substantially lower level expression in several other normal tissues (i.e., colon, ovary, small intestine, spleen and testis) was detectable only at 30 cycles of amplification in brain, pancreas, colon and small intestine (FIG. 2, panels B and C).

Example 2

Isolation of Full Length STEAP-1 Encoding cDNA

The 436 bp 8P1D4 gene fragment (Example 1) was used to isolate additional cDNAs encoding the 8P1D4/STEAP-1 gene. Briefly, a normal human prostate cDNA library (Clontech) was screened with a labeled probe generated from the 436 bp 8P1D4 cDNA. One of the positive clones, clone 10, is 1195 bp in length and encodes a 339 amino acid protein having nucleotide and encoded amino add sequences bearing no significant homology to any known human genes or proteins (homology to a rat Kidney Injury Protein recently described in International Application WO98/53071). The encoded protein contains at least 6 predicted transmembrane motifs implying a cell surface orientation (see FIG. 1A, predicted transmembrane motifs underlined). These structural features led to the designation "STEAP", for "Six Transmembrane Epithelial Antigen of the Prostate". Subsequent identification of additional STEAP proteins led to the re-designation of the 8P1D4 gene product as "STEAP-1". The STEAP-1 cDNA and encoded amino acid sequences are shown in FIG. 1A and correspond to SEQ ID NOS: XX and XX, respectively. STEAP-1 cDNA clone 10 has been deposited with the American Type Culture Collection ("ATCC") (Mannassas, Va.) as plasmid 8P1D4 clone 10.1 on Aug. 26, 1998 as ATCC Accession Number 98849. The STEAP-1 cDNA clone can be excised therefrom using EcoRI/XbaI double digest (EcoRI at the 5'end, XbaI at the 3'end).

Example 3

STEAP-1 Gene and Protein Expression Analysis

In order to begin to characterize the biological characteristics of STEAP-1, an extensive evaluation of STEAP-1 mRNA and STEAP-1 protein expression across a variety of human tissue specimens was undertaken. This evaluation included Northern blot, Western blot and immunohistochemical analysis of STEAP-1 expression in a large number of normal human tissues, human prostate cancer xenografts and cell lines, and various other human cancer cell lines.

Example 3A

Northern Blot Analysis of STEAP-1 mRNA Expression in Normal Human Tissues

Initial analysis of STEAP-1 mRNA expression in normal human tissues was conducted by Northern blotting two multiple tissue blots obtained from Clontech (Palo Alto, Calif.), comprising a total of 16 different normal human tissues, using labeled STEAP-1 clone 10 as a probe. RNA samples were quantitatively normalized with a β-actin probe. The results are shown in FIG. 3A. The highest expression level was detected in normal prostate, with an approximately 5-10 fold lower level of expression detected in colon and liver. These northern blots showed two transcripts of approximately 1.4 kb and 4.0 kb, the former of which corresponds to the full length STEAP-1 clone 10 cDNA, which encodes the entire STEAP-1 open reading frame. The larger transcript was separately cloned as a 3627 bp cDNA from a normal prostate library, the sequence of which contains a 2399 bp intron (FIG. 4).

This initial analysis was extended by using the STEAP-1 clone 10 probe to analyze an RNA dot blot matrix of 37 normal human tissues (Clontech, Palo Alto, Calif.; Human Master Blot™). The results are shown in FIG. 3B and show strong STEAP-1 expression only in prostate. Very low level STEAP-1 RNA expression was detected in liver, lung, trachea and fetal liver tissue, at perhaps a 5-fold lower level compared to prostate. No expression was detected in any of the remaining tissues. Based on these analyses, significant STEAP-1 expression appears to be prostate specific in normal tissues.

Example 3B

Northern Blot Analysis of STEAP-1 mRNA Expression in Prostate Cancer Xenografts and Cell Lines To analyze STEAP-1 expression in human cancer tissues and cell lines, RNAs derived from human prostate cancer xenografts and an extensive panel of prostate and non-prostate cancer cell lines were analyzed by Northern blot using STEAP-1 cDNA clone 10 as probe. All RNA samples were quantitatively normalized by ethiduim bromide staining and subsequent analysis with a labeled β-actin probe.

The results, presented in FIG. 5, show high level STEAP-1 expression in all the LAPC xenografts and all of the prostate cancer cell lines. Expression in the LAPC-9 xenografts was higher compared to the LAPC-4 xenografts, with no significant difference observed between androgen-dependent and androgen-independent sublines (FIG. 5A). Expression in the LAPC-4 xenografts was comparable to expression in normal prostate. Lower levels of expression were detected in PrEC cells (Clonetics), which represent the basal cell compartment of the prostate. Analysis of prostate cancer cell lines showed highest expression levels in LNCaP, an androgen dependent prostate carcinoma cell line. Significant expression was also detected in the androgen-independent cell lines PC-3 and DU145. High levels of STEAP expression were also detected in LAPC-4 and LAPC-9 tumors that were grown within the tibia of mice as a model of prostate cancer bone metastasis (FIG. 5B).

Significantly, very strong STEAP-1 expression was also detected in many of the non-prostate human cancer cell lines analyzed (FIG. 5A). Particularly high level expression was observed in RD-ES cells, an Ewing sarcoma (EWS) derived cell line. Additionally, very high level expression was also detected in several of the colon cancer cell lines (e.g., CaCo-2, LoVo, T84 and Colo-205), bladder carcinoma cell lines (e.g., SCABER, UM-UC-3, TCCSUP and 5637), ovarian cancer cell lines (e.g., OV-1063 and SW 626) and pancreatic cancer cell lines (e.g., HPAC, Capan-1, PANC-1 and BxPC-3). These results, combined with the absence of strong expression in the corresponding normal tissues (FIG. 3), indicate that STEAP-1 may be generally up-regulated in these types (as well as other types) of human cancers.

Example 3C

Western Blot Analysis of STEAP-1 Protein Expression in Prostate and Other Cancers A 15 mer peptide corresponding to amino acid residues 14 through 28 of the STEAP-1 amino acid sequence as shown in FIG. 1A (WKMKPRRNLEEDDYL) (SEQ ID NO: 35) was synthesized and used to immunize sheep for the generation of sheep polyclonal antibodies towards the amino-terminus of the protein (anti-STEAP-1) as follows. The peptide was conjugated to KLH (keyhole limpet hemocyanin). The sheep was initially immunized with 400 µg of peptide in complete Freund's adjuvant. The animal was subsequently boosted every two weeks with 200 µg of peptide in incomplete Freund's adjuvant. Anti-STEAP antibody was affinity-purified from sheep serum using STEAP peptide coupled to Affi-Gel 10 (Bio-Rad). Purified antibody is stored in phosphate-buffered saline with 0.1% sodium azide.

To test antibody specificity, the cDNA of STEAP-1 was cloned into a retroviral expression vector (pSRαtkneo, Muller et al., 1991, MCB 11:1785). NIH 3T3 cells were infected with retroviruses encoding STEAP-1 and were selected in G418 for 2 weeks. Western blot analysis of protein extracts of infected and un-infected NIH 3T3 cells showed expression of a protein with an apparent molecular weight of 36 kD only in the infected cells (FIG. 6, lanes marked "3T3 STEAP" AND "3T3").

The anti-STEAP-1 polyclonal antibody was used to probe Western blots of cell lysates prepared from a variety of prostate cancer xenograft tissues, prostate cancer cell lines and other non-prostate cancer cell lines. Protein samples (20μg each) were quantitatively normalized by probing the blots with an anti-Grb-2 antibody.

The results are shown in FIG. 6. STEAP-1 protein was detected in all of the LAPC prostate cancer xenografts, all of the prostate cancer cell lines, a primary prostate cancer specimen and its matched normal prostate control. Highest STEAP-1 protein expression was detected in the LAPC-9 xenograft and in LNCaP cells, in agreement with the Northern blot analysis described immediately above. High level expression was also observed in the bladder carcinoma cell line UM-UC-3. Expression in other cancer cell lines was also detectable (FIG. 6).

Example 3D

Immunohistochemical Analysis f STEAP-1 Protein Expression in Pr State Tumor Biopsy and Surgical Specimens To determine the extent of STEAP-1 protein expression in clinical materials, tissue sections were prepared from a variety of prostate cancer biopsies and surgical samples for immunohistochemical analysis. Tissues were fixed in 10% formalin, embedded in paraffin, and sectioned according to standard protocol. Formalin-fixed, paraffin-embedded sections of LNCaP cells were used as a positive control. Sections were stained with an anti-STEAP-1 polyclonal antibody directed against a STEAP-1 N-terminal epitope (as described immediately above). LNCaP sections were stained in the presence of an excess amount of the STEAP-1 N-terminal peptide immunogen used to generate the polyclonal antibody (peptide 1) or a non-specific peptide derived from a distinct region of the STEAP-1 protein (peptide 2; YQQVQQNKEDAWIEH))SEQ ID NO: 30).

The results are shown in FIG. 8. LNCaP cells showed uniformly strong peri-cellular staining in all cells (FIG. 8b). Excess STEAP N-terminal peptide (peptide 1) was able to competitively inhibit antibody staining (FIG. 8a), while peptide 2 had no effect (FIG. 8b). Similarly, uniformly strong peri-cellular staining was seen in the LAPC-9 (FIG. 8f) and LAPC-4 prostate cancer xenografts (data not shown). These results are clear and suggest that the staining is STEAP specific. Moreover, these results visually localize STEAP to the plasma membrane, corroborating the biochemical findings presented in Example 4 below.

The results obtained with the various clinical specimens are show in FIG. 8c (normal prostate tissue), FIG. 8d (grade 3 prostatic carcinoma), and FIG. 8e (grade 4 prostatic carcinoma), and are also included in the summarized results shown in TABLE 1. Light to strong staining was observed in the glandular epithelia of all prostate cancer samples tested as well as in all samples derived from normal prostate or benign disease. The signal appears to be strongest at the cell membrane of the epithelial cells, especially at the cell-cell junctions (FIGS. 8c, d and e) and is also inhibited with excess STEAP N-terminal peptide 1 (data not shown). Some basal cell staining is also seen in normal prostate (FIG. 8c), which is more apparent when examining atrophic glands (data not shown). STEAP-1 seems to be expressed at all stages of prostate cancer since lower grades (FIG. 8d), higher grades (FIG. 8e) and metastatic prostate cancer (represented by LAPC-9; FIG. 8f) all exhibit strong staining.

Immunohistochemical staining of a large panel of normal non-prostate tissues showed no detectable STEAP-1 expression in 24 of 27 of these normal tissues (Table 1). Only three tissue samples showed some degree of anti-STEAP-1 staining. In particular, normal bladder exhibited low levels of cell surface staining in the transitional epithelium (FIG. 8g). Pancreas and pituitary showed low levels of cytoplasmic staining (Table 1). It is unclear whether the observed cytoplasmic staining is specific or is due to non-specific binding of the antibody, since northern blotting showed little to no STEAP-1 expression in pancreas (FIG. 3). Normal colon, which exhibited higher mRNA levels than pancreas by Northern blotting (FIG. 3), exhibited no detectable staining with anti-STEAP antibodies (FIG. 8h). These results indicate that cell surface expression of STEAP-1 in normal tissues appears to be restricted to prostate and bladder.

TABLE 1

IMMUNOHISTOCHEMICAL STAINING OF HUMAN TISSUES WITH ANTI-STEAP-1 POLYCLONAL ANTIBODY

| STAINING INTENSITY | TISSUE |
|---|---|
| NONE | cerebellum, cerebral cortex, spinal cord, heart, skeletal muscle, artery, thymus, spleen, bone marrow, lymph node, lung, colon, liver, stomach, kidney, testis, ovary, fallopian tubes, placenta, uterus, breast, adrenal gland, thyroid gland, skin, bladder (3/5) |
| LIGHT TO MODERATE | bladder (2/5), pituitary gland (cytoplasmic), pancreas (cytoplasmic), BPH (3/5), prostate cancer (3/10) |
| STRONG | prostate (2/2), BPH (2/5), prostate cancer** (7/10) |

*In cases where more than one sample is analyzed per tissue, the numbers in brackets indicates how many samples correspond to the staining category/ total analyzed.
**Prostate cancer grades ranged from Gleason grades 3 to 5.

Example 4

Biochemical Characterization of STEAP-1 Protein

To initially characterize the STEAP-1 protein, cDNA clone 10 was cloned into the pcDNA 3.1 Myc-His plasmid (Invitrogen), which encodes a 6His tag at the carboxyl-terminus, transfected into 293T cells, and analyzed by flow cytometry using anti-His monoclonal antibody (His-probe, Santa Cruz) as well as the anti-STEAP-1 polyclonal antibody described above. Staining of cells was performed on intact cells as well as permeabilized cells. The results indicated that only permeabilized cells stained with both antibodies, suggesting that both termini of the STEAP-1 protein are localized intracellularly. It is therefore possible that one or more of the STEAP-1 protein termini are associated with intracellular organelles rather than the plasma membrane.

To determine whether STEAP-1 protein is expressed at the cell surface, intact STEAP-1-transfected 293T cells were labeled with a biotinylation reagent that does not enter live cells.

STEAP-1 was then immunoprecipitated from cell extracts using the anti-His and anti-STEAP antibodies. SV40 large T antigen, an intracellular protein that is expressed at high levels in 293T cells, and the endogenous cell surface transferrin receptor were immunoprecipitated as negative and positive controls, respectively. After immunoprecipitation, the proteins were transferred to a membrane and visualized with horseradish peroxidase-conjugated streptavidin. The results of this analysis are shown in FIG. 7. Only the transferrin receptor (positive control) and STEAP-1 were labeled with biotin, while the SV40 large T antigen (negative control) was not detectably labeled (FIG. 7A). Since only cell surface proteins are labeled with this technique, it is clear from these results that STEAP-1 is a cell surface protein. Combined with the results obtained from the flow cytometric analysis, it is clear that STEAP-1 is a cell surface protein with intracellular amino- and carboxyl-termini.

Furthermore, the above results together with the STEAP-1 secondary structural predictions, shows that STEAP-1 is a type IIIa membrane protein with a molecular topology of six potential transmembrane domains, 3 extracellular loops, 2 intracellular loops and two intracellular termini. A schematic representation of STEAP-1 protein topology relative to the cell membrane is shown in FIG. 1B.

In addition, prostate, bladder and colon cancer cells were directly analyzed for cell surface expression of STEAP-1 by biotinylation studies. Briefly, biotinylated cell surface proteins were affinity purified with streptavidin-gel and probed with the anti-STEAP-1 polyclonal antibody described above. Western blotting of the streptavidin purified proteins clearly show cell surface biotinylation of endogenous STEAP-1 in all prostate (LNCaP, PC-3, DU145), bladder (UM-UC-3, TCCSUP) and colon cancer (LoVo, Colo) cells tested, as well as in NIH 3T3 cells infected with a STEAP-1 encoding retrovirus, but not in non-expressing NIH 3T3 cells used as a negative control (FIG. 7B). In a further negative control, STEAP-1 protein was not detected in streptavidin precipitates from non-biotinylated STEAP expressing cells (FIG. 7B).

Example 5

Identification and Structural Analysis Other Human STEAPs

STEAP-1 has no homology to any known human genes. In an attempt to identify additional genes that are homologous to STEAP-1, the protein sequence of STEAP-1 was used as an electronic probe to identify family members in the public EST (expression sequence tag) database (dbest). Using the "tblastn" function in NCBI (National Center for Biotechnology Information), the dbest database was queried with the STEAP-1 protein sequence. This analysis revealed additional putative STEAP-1 homologues or STEAP family members, as further described below.

In addition, SSH cloning experiments also identified a STEAP-1 related cDNA fragment, clone 98P4B6. This clone was isolated from SSH cloning using normal prostate cDNA as tester and LAPC-4 AD cDNA as driver. A larger partial sequence of the 98P4B6 clone was subsequently isolated from a normal prostate library; this clone encodes an ORF of 173 amino acids with close homology to the primary structure of STEAP-1, and thus was designated STEAP-2. A full length STEAP-2 cDNA of 2454 bp was isolated from a prostate library. The STEAP-2 nucleotide and encoded ORF amino acid sequences are shown in FIG. 9. An amino acid alignment of the STEAP-1 and partial STEAP-2 primary structures is shown in FIGS. 11A and 11B. STEAP-1 and -2 share 61% identity over their 171 amino acid residue overlap (FIG. 11B). The STEAP-2 cDNA has been deposited with the American Type Culture Collection ("ATCC") (Mannassas, Va.) as plasmid 98P4B6-GTD3 as ATCC Accession Number PTA-311.

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The STEAP-2 cDNA (98P4B6-GTD3) contains a 355 bp 5'UTR (untranslated region) that is 72% GC rich, suggesting that it contains translational regulatory elements. The cDNA encodes an open reading frame (ORF) of 454 amino acids (a.a.) with six potential transmembrane domains. This is in contrast to STRAP, which is 339 a.a. in length. Alignment with STRAP-1 demonstrates 54.9% identity over a 237 amino acid overlap. Interestingly, the locations of the six putative transmembrane domains in STRAP-2 coincide with the locations of the transmembrane domains in STRAP-1 (see alignment). The homology of STRAP-2 with STRAP-1 is highest in the regions spanned by the first putative extracellular loop to the fifth transmembrane domain. This analysis and the sequence of STRAP-2 suggest some significant differences between STRAP-1 and STRAP-2: STRAP-2 exhibits a 205 a.a. long intracellular N-terminus (compared to 69 a.a. in STRAP-1) and a short 4 a.a. intracellular C-terminus (compared to 26 a.a. in STRAP-1). These differences could imply significant differences in function and/or interaction with intracellular signaling pathways. To identify a unique mouse EST corresponding to STRAP-2, the unique N-terminus of STRAP-2 was used to query the dbest database. One mouse EST was isolated (AI747886, mouse kidney) that may be used in the identification of mouse STRAP-2 and in expression analysis of STRAP-2 in mouse.

Two ESTs encoding ORFs bearing close homology to the STEAP-1 and STEAP-2 sequences were also identified by electronic probing with the STEAP-1 protein sequence. These ESTs (AI139607 and R80991) were provisionally designated STEAP-3 and STEAP-4. A full length cDNA encoding STEAP-3 was subsequently cloned, and its nucleotide and deduced amino acid sequences are shown in FIG. 10A. The nucleotide sequences of the ESTs corresponding to the STEAPs are reproduced in FIG. 10B.

An amino acid alignment of the structures of STEAP-1, STEAP-2, STEAP-3 and the partial sequence of the putative STEAP-4 is shown in FIG. 11A. This alignment shows a close structural similarity between all four STEAP family proteins, particularly in the predicted transmembrane domains. As indicated above, STEAP-1 and STEAP-2 demonstrate 54.9% identity over a 237 amino add overlap. STEAP-1 and STEAP-3 are 40.9% identical over a 264 amino acid region, while STEAP-2 and STEAP-3 are 47.8% identical over a 416 amino acid region.

Example 6

Expression Analysis of STEAP-2 and Other Human STEAP Family Members

Example 6A

Tissue Specific Expression of STEAP Family Members in Normal Human Tissues

RT-PCR analysis of STEAP-2 shows expression in all the LAPC prostate cancer xenografts and in normal prostate (FIG. 14, panel A). Analysis of 8 normal human tissues shows prostate-specific expression after 25 cycles of amplification (FIG. 14, panel B). Lower level expression in other tissues was detected only after 30 cycles of amplification. Northern blotting for STEAP-2 shows a pattern of 2 transcripts (approximately 3 and 8 kb in size) expressed only in prostate (and at significantly lower levels in the LAPC xenografts), with no detectable expression in any of the 15 other normal human tissues analyzed (FIG. 15, panel C). Thus, STEAP-2 expression in normal human tissues appears to be highly prostate-specific.

Expression analysis of STEAP family members in normal tissues was performed by Northern blot and/or RT-PCR. All STEAP family members appeared to exhibit tissue restricted expression patterns. STEAP-3/AI139607 expression is shown in FIG. 12A (Northern) and FIG. 12B (RT-PCR). STEAP-4/R80991 expression is shown in FIG. 13.

Example 6B

Expression of STEAP-2 in Various Cancer Cell Lines

The RT-PCR results above suggested that the different STEAP family members exhibit different tissue expression patterns. Interestingly, STEAP-2, which appears very prostate-specific, seems to be expressed at lower levels in the LAPC xenografts. This is in contrast to STEAP-1, which is highly expressed in both normal and malignant prostate tissue.

To better characterize this suggested difference in the STEAP-2 prostate cancer expression profile (relative to STEAP-1), Northern blotting was performed on RNA derived from the LAPC xenografts, as well as several prostate and other cancer cell lines, using a STEAP-2 specific probe (labeled cDNA clone 98P4B6). The results are shown in FIG. 16 and can be summarized as follows. STEAP-2 is highly expressed in normal prostate and in some of the prostate cancer xenografts and cell lines. More particularly, very strong expression was observed in the LAPC-9 AD xenograft and the LNCaP cells. Significantly attenuated or no expression was observed in the other prostate cancer xenografts and cell lines. Very strong expression was also evident in the Ewing Sarcoma cell line RD-ES. Unlike STEAP-1, which is highly expressed in cancer cell lines derived from bladder, colon, pancreatic and ovarian tumors, STEAP-2 showed low to non-detectable expression in these same cell lines (compare with FIG. 5). Interestingly, STEAP-2 was also non-detectable in PrEC cells, which are representative of the normal basal cell compartment of the prostate. These results suggests that expression of STEAP-1 and STEAP-2 are differentially regulated. While STEAP-1 may be a gene that is generally up-regulated in cancer, STEAP-2 may be a gene that is more restricted to normal prostate and prostate cancer.

Example 7

Chromosomal Localization of STEAP Genes

The chromosomal localization of STEAP-1 was determined using the GeneBridge 4 Human/Hamster radiation hybrid (RH) panel (Walter et al., 1994, Nat. Genetics 7:22) (Research Genetics, Huntsville Ala.), while STEAP-2 and the STEAP homologues were mapped using the Stanford G3 radiation hybrid panel (Stewart et al., 1997, Genome Res. 7:422).

The following PCR primers were used for STEAP-1:

```
8P1D4.1
5' ACTTTGTTGATGACCAGGATTGGA 3'    (SEQ ID NO: 14)

8P1D4.2
5' CAGAACTTCAGCACACACAGGAAC 3'    (SEQ ID NO: 14)
```

The resulting STEAP-1 mapping vector for the 93 radiation hybrid panel DNAs (210000020110101000100000010111010122100011100111011010100010001000101001021000 001111001010000), and the mapping program RHMapper available at the Broad Institute website, localized the STEAP-1 gene to chromosome 7p22.3, telomeric to D7S531.

The following PCR primers were used for 98P4B6/STEAP-2:

```
98P4B6.1
5' GACTGAGCTGGAACTGGAATTTGT 3'    (SEQ ID NO: 20)

98P4B6.2
5' TTTGAGGAGACTTCATCTCACTGG 3'    (SEQ ID NO: 21)
```

The resulting vector (000001001000000000000000000000001001000000000010001000 0000000000100001010101001011), and the mapping program RHserver available at the website for the Stanford Human Genome Center maps the 98P4B6 (STEAP-2) gene to chromosome 7q21.

The following PCR primers were used for AI139607:

```
AI139607.1
5' TTAGGACAACTTGATCACCAGCA 3'     (SEQ ID NO: 16)

AI139607.2
5' TGTCCAGTCCAAACTGGGTTATTT 3'    (SEQ ID NO: 17)
```

The resulting vector (000000001000000000000000000010001000002000000010001000 000001000000100010001010000010), and the mapping program RHserver available at the website for the Stanford Human Genome Center maps AI139607 to chromosome 7q21.

The following PCR primers were used for R80991:

```
R80991.3
5' ACAAGAGCCACCTCTGGGTGAA 3'      (SEQ ID NO: 33)

R80991.4
5' AGTTGAGCGAGTTTGCAATGGAC 3'     (SEQ ID NO: 34)
```

The resulting vector (00000000000200001020000000001000000000000000000010000 00000100001110000000100100001), and the mapping program RHserver available at the website for the Stanford Human Genome Center maps R80991 to chromosome 2q14-q21, near D2S2591.

In summary, the above results show that three of the putative human STEAP family members localize to chromosome 7, as is schematically depicted in FIG. 17. In particular, the STEAP-1 gene localizes to the far telomeric region of the short arm of chromosome 7, at 7p22.3, while STEAP-2 and AI139607 localize to the long arm of chromosome 7, at 7q21 (FIG. 17). R80991 maps to chromosome 2q14-q21.

Example 8

Identification of Intron-Exon Boundaries of STEAP-1

Genomic clones for STEAP-1 were identified by searching GenBank for BAC clones containing STEAP-1 sequences, resulting in the identification of accession numbers AC004969 (PAC DJ1121E10) and AC005053 (BAC RG041D11). Using the sequences derived from the PAC and BAC clones for STEAP the intron-exon boundaries were defined (FIG. 18). A total of 4 exons and 3 introns were identified within the coding region of the STEAP gene. Knowledge of the exact exon-intron structure of the STEAP-1 gene may be used for designing primers within intronic sequences which in turn may be used for genomic amplification of exons. Such amplification permits single-stranded conformational polymorphism (SSCP) analysis to search for polymorphisms associated with cancer. Mutant or polymorphic exons may be sequenced and compared to wild type STEAP. Such analysis may be useful to identify patients who are more susceptible to aggressive prostate cancer, as well as other types of cancer, particularly colon, bladder, pancreatic, ovarian, cervical and testicular cancers.

Southern blot analysis shows that the STEAP-1 gene exists in several species including mouse (FIG. 19). Therefore, a mouse BAC library (Mouse ES 129-V release I, Genome Systems, FRAC-4431) was screened with the human cDNA for STEAP-1 (clone 10, Example 2). One positive clone, 12P11, was identified and confirmed by southern blotting (FIG. 20). The intron-exon boundary information for human STEAP may be used to identify the mouse STEAP-1 coding sequences.

The mouse STEAP-1 genomic clone may be used to study the biological role of STEAP-1 during development and tumorigenesis. Specifically, the mouse genomic STEAP-1 clone may be inserted into a gene knock-out (K/O) vector for targeted disruption of the gene in mice, using methods generally known in the art. In addition, the role of STEAP in metabolic processes and epithelial cell function may be elucidated. Such K/O mice may be crossed with other prostate cancer mouse models, such as the TRAMP model (Greenberg et al., 1995, PNAS 92:3439), to determine whether STEAP influences the development and progression of more or less aggressive and metastatic prostate cancers.

Example 9

Predicrion of HLA-A2 Binding Peptides from STEAP-1 and STEAP-2

The complete amino acid sequences of the STEAP-1 and STEAP-2 proteins were entered into the HLA Peptide Motif Search algorithm found in the Bioinformatics and Molecular Analysis Section (BIMAS) Web site. The HLA Peptide Motif Search algorithm was developed by Dr. Ken Parker based on binding of specific peptide sequences in the groove of HLA Class I molecules and specifically HLA-A2 (Falk et al., 1991, Nature 351: 290-6; Hunt et al., 1992, Science 255:1261-3; Parker et al., 1992, J. Immunol. 149:3580-7; Parker et al., 1994, J. Immunol. 152:163-75). This algorithm allows location and ranking of 8-mer, 9-mer, and 1 0-mer peptides from a complete protein sequence for predicted binding to HLA-A2 as well as other HLA Class I molecules. Most HLA-A2 binding peptides are 9-mers favorably containing a leucine (L) at position 2 and a valine (V) or leucine (L) at position 9.

The results of STEAP-1 and STEAP-2 predicted binding peptides are shown in Table 2 below. For both proteins the top 5 ranking candidates are shown along with their location, the amino acid sequence of each specific peptide, and an estimated binding score. The binding score corresponds to the estimated half-time of dissociation of complexes containing the peptide at 37° C at pH 6.5. Peptides with the highest binding score (i.e. 10776.470 for STEAP-1 peptide 165; 1789.612 for STEAP-2 peptide 227) are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (Refs. 5,6). Immunogenicity of specific peptides can be evaluated in vitro by stimulation of CD8+ cytotoxic T lymphocytes (CTL) in the presence of dendritic cells (Xue et al., 1997, Prostate 30:73-8; Peshwa et al., 1998, Prostate 36:129-38).

TABLE 1

Predicted Binding of Steap-1 and STEAP-2 Peptide Sequences with Highest Affinity for HLA-A2

| Rank | Start Position | Subsequence Residue Listing | Score (Estimate of Half Time of Disassociation of Molecule containing This Subsequence) |
|---|---|---|---|
| STEAP-1 (SEQ ID NO: 2) | | | |
| 1 | 165 | GLLSFFFAV (SEQ ID NO: 36) | 10776.470 |
| 2 | 86 | FLYTLLREV (SEQ ID NO: 37) | 470.951 |
| 3 | 262 | LLLGTIHAL (SEQ ID NO: 38) | 309.050 |
| 4 | 302 | LIFKSILFL (SEQ ID NO: 39) | 233.719 |
| 5 | 158 | MLTRKQFGL (SEQ ID NO: 40) | 210.633 |
| STEAP-2 (SEQ ID NO: 6) | | | |
| 1 | 227 | FLYSFVRDV (SEQ ID NO: 41) | 1789.612 |
| 2 | 402 | ALLISTFHV (SEQ ID NO: 42) | 1492.586 |
| 3 | 307 | LLSFFFAMV (SEQ ID NO: 43) | 853.681 |
| 4 | 306 | GLLSFFFAM (SEQ ID NO: 44) | 769.748 |
| 5 | 100 | SLWDLRHLL (SEQ ID NO: 45) | 726.962 |

This application is a continuation-in-part of U.S. application Ser. No. 09/323,873 filed Jun. 1, 1999, entitled "NOVEL SERPENTINE TRANSMEMBRANE ANTIGENS EXPRESSED IN HUMAN CANCERS AND USES THEREOF" The proteins designated "STRAP" in that application have been re-named "STEAP" in the present application.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. An isolated polynucleotide selected from the group consisting of (a) a polynucleotide comprising the sequence as shown in FIG. 9 (SEQ ID NO: 5), wherein T can also be U; (b) a polynucleotide comprising the sequence as shown in FIG. 9 (SEQ ID NO: 5), from nucleotide residue number 356 through nucleotide residue number 1717, wherein T can also be U; (c) a polynucleotide encoding a polypeptide comprising the sequence of the STEAP-2 polypeptide encoded by the cDNAs contained in the plasmid deposited with American Type Culture Collection as Accession No. PTA-311; and (d) a polynucleotide encoding a STEAP-2 protein comprising the amino acid sequence as shown in FIG. 9 (SEQ ID NO: 6).

2. An isolated polynucleotide that is the complete complement of a polynucleotide according to claim 1.

3. An isolated polynucleotide according to claim 1 or 2 which is labeled with a detectable marker.

4. A recombinant expression vector which comprises a polynucleotide according to claim 1 or 2.

5. An isolated host cell which comprises an expression vector according to claim 4.

6. A process for producing a STEAP-2 protein comprising culturing a host cell of claim 5 under conditions that produce the protein and recovering the STEAP-2 protein from the culture.

\* \* \* \* \*

SEQUENCE LISTING

<160> NUMBER OF SEQ ID NOS: 47

<210> SEQ ID NO 1
<211> LENGTH: 1193
<212> TYPE: DNA
<213> ORGANISM: Homo sapiens
<220> FEATURE:
<221> NAME/KEY: CDS
<222> LOCATION: (64)...(1083)

<400> SEQUENCE: 1

```
gagactcacg gtcaagctaa ggcgaagagt gggtggctga agccatacta ttttatagaa        60 tta atg gaa agc aga aaa gac atc aca aac caa gaa gaa ctt tgg aaa        108
    Met Glu Ser Arg Lys Asp Ile Thr Asn Gln Glu Glu Leu Trp Lys
    1               5                  10                  15 atg aag cct agg aga aat tta gaa gaa gac gat tat ttg cat aag gac        156
Met Lys Pro Arg Arg Asn Leu Glu Glu Asp Asp Tyr Leu His Lys Asp
            20                  25                  30 acg gga gag acc agc atg cta aaa aga cct gtg ctt ttg cat ttg cac        204
Thr Gly Glu Thr Ser Met Leu Lys Arg Pro Val Leu Leu His Leu His
        35                  40                  45 caa aca gcc cat gct gat gaa ttt gac tgc cct tca gaa ctt cag cac        252
Gln Thr Ala His Ala Asp Glu Phe Asp Cys Pro Ser Glu Leu Gln His
    50                  55                  60 aca cag gaa ctc ttt cca cag tgg cac ttg cca att aaa ata gct gct        300
Thr Gln Glu Leu Phe Pro Gln Trp His Leu Pro Ile Lys Ile Ala Ala
65                  70                  75 att ata gca tct ctg act ttt ctt tac act ctt ctg agg gaa gta att        348
Ile Ile Ala Ser Leu Thr Phe Leu Tyr Thr Leu Leu Arg Glu Val Ile
 80                  85                  90                  95 cac cct tta gca act tcc cat caa caa tat ttt tat aaa att cca atc        396
His Pro Leu Ala Thr Ser His Gln Gln Tyr Phe Tyr Lys Ile Pro Ile
                100                 105                 110 ctg gtc atc aac aaa gtc ttg cca atg gtt tcc atc act ctc ttg gca        444
Leu Val Ile Asn Lys Val Leu Pro Met Val Ser Ile Thr Leu Leu Ala
            115                 120                 125 ttg gtt tac ctg cca ggt gtg ata gca gca att gtc caa ctt cat aat        492
Leu Val Tyr Leu Pro Gly Val Ile Ala Ala Ile Val Gln Leu His Asn
        130                 135                 140 gga acc aag tat aag aag ttt cca cat tgg ttg gat aag tgg atg tta        540
Gly Thr Lys Tyr Lys Lys Phe Pro His Trp Leu Asp Lys Trp Met Leu
    145                 150                 155 aca aga aag cag ttt ggg ctt ctc agt ttc ttt ttt gct gta ctg cat        588
Thr Arg Lys Gln Phe Gly Leu Leu Ser Phe Phe Phe Ala Val Leu His
160                 165                 170                 175 gca att tat agt ctg tct tac cca atg agg cga tcc tac aga tac aag        636
Ala Ile Tyr Ser Leu Ser Tyr Pro Met Arg Arg Ser Tyr Arg Tyr Lys
                180                 185                 190 ttg cta aac tgg gca tat caa cag gtc caa caa aat aaa gaa gat gcc        684
Leu Leu Asn Trp Ala Tyr Gln Gln Val Gln Gln Asn Lys Glu Asp Ala
            195                 200                 205 tgg att gag cat gat gtt tgg aga atg gag att tat gtg tct ctg gga        732
Trp Ile Glu His Asp Val Trp Arg Met Glu Ile Tyr Val Ser Leu Gly
        210                 215                 220 att gtg gga ttg gca ata ctg gct ctg ttg gct gtg aca tct att cca        780
Ile Val Gly Leu Ala Ile Leu Ala Leu Leu Ala Val Thr Ser Ile Pro
    225                 230                 235 tct gtg agt gac tct ttg aca tgg aga gaa ttt cac tat att cag agc        828
Ser Val Ser Asp Ser Leu Thr Trp Arg Glu Phe His Tyr Ile Gln Ser
```

```
                240                 245                 250                 255
aag cta gga att gtt tcc ctt cta ctg ggc aca ata cac gca ttg att        876
Lys Leu Gly Ile Val Ser Leu Leu Leu Gly Thr Ile His Ala Leu Ile
                    260                 265                 270 ttt gcc tgg aat aag tgg ata gat ata aaa caa ttt gta tgg tat aca        924
Phe Ala Trp Asn Lys Trp Ile Asp Ile Lys Gln Phe Val Trp Tyr Thr
                    275                 280                 285 cct cca act ttt atg ata gct gtt ttc ctt cca att gtt gtc ctg ata        972
Pro Pro Thr Phe Met Ile Ala Val Phe Leu Pro Ile Val Val Leu Ile
                    290                 295                 300 ttt aaa agc ata cta ttc ctg cca tgc ttg agg aag aag ata ctg aag       1020
Phe Lys Ser Ile Leu Phe Leu Pro Cys Leu Arg Lys Lys Ile Leu Lys
                    305                 310                 315 att aga cat ggt tgg gaa gac gtc acc aaa att aac aaa act gag ata       1068
Ile Arg His Gly Trp Glu Asp Val Thr Lys Ile Asn Lys Thr Glu Ile
320                 325                 330                 335 tgt tcc cag ttg tag aattactgtt tacacacatt tttgttcaat attgatatat       1123
Cys Ser Gln Leu * tttatcacca acatttcaag tttgtatttg ttaataaaat gattattcaa ggaaaaaaaa     1183
aaaaaaaaaa                                                            1193

<210> SEQ ID NO 2
<211> LENGTH: 339
<212> TYPE: PRT
<213> ORGANISM: Homo sapiens

<400> SEQUENCE: 2

Met Glu Ser Arg Lys Asp Ile Thr Asn Gln Glu Glu Leu Trp Lys Met
 1               5                  10                  15

Lys Pro Arg Arg Asn Leu Glu Glu Asp Asp Tyr Leu His Lys Asp Thr
                20                  25                  30

Gly Glu Thr Ser Met Leu Lys Arg Pro Val Leu Leu His Leu His Gln
            35                  40                  45

Thr Ala His Ala Asp Glu Phe Asp Cys Pro Ser Glu Leu Gln His Thr
        50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
130                 135                 140

Thr Lys Tyr Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
        210                 215                 220
```

```
Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
            245                 250                 255

Leu Gly Ile Val Ser Leu Leu Gly Thr Ile His Ala Leu Ile Phe
        260                 265                 270

Ala Trp Asn Lys Trp Ile Asp Ile Lys Gln Phe Val Trp Tyr Thr Pro
        275                 280                 285

Pro Thr Phe Met Ile Ala Val Phe Leu Pro Ile Val Val Leu Ile Phe
        290                 295                 300

Lys Ser Ile Leu Phe Leu Pro Cys Leu Arg Lys Ile Leu Lys Ile
305                 310                 315                 320

Arg His Gly Trp Glu Asp Val Thr Lys Ile Asn Lys Thr Glu Ile Cys
                325                 330                 335

Ser Gln Leu

<210> SEQ ID NO 3
<211> LENGTH: 111
<212> TYPE: DNA
<213> ORGANISM: Homo sapiens

<400> SEQUENCE: 3
ggcggaggcg aggcggagg gcgaggggcg gggagcgccg cctggagcgc ggcaggtcat       60
attgaacatt ccagatacct atcattactc gatgctgttg ataacagcaa g              111

<210> SEQ ID NO 4
<211> LENGTH: 3627
<212> TYPE: DNA
<213> ORGANISM: Homo sapiens

<400> SEQUENCE: 4
ggggcccgca cctctgggca gcagcggcag ccgagactca cggtcaagct aaggcgaaga       60
gtgggtggct gaagccatac tattttatag aattaatgga aagcagaaaa gacatcacaa      120
accaagaaga actttggaaa atgaagccta ggagaaattt agaagaagac gattatttgc      180
ataaggacac gggagagacc agcatgctaa aaagacctgt gcttttgcat ttgcaccaaa      240
cagcccatgc tgatgaattt gactgcccct cagaacttca gcacacacag gaactctttc      300
cacagtggca cttgccaatt aaaatagctg ctattatagc atctctgact tttctttaca      360
ctcttctgag ggaagtaatt caccccttag caacttccca tcaacaatat ttttataaaa      420
ttccaatcct ggtcatcaac aaagtcttgc caatggtttc catcactctc ttggcattgg      480
tttacctgcc aggtgtgata gcagcaattg tccaacttca taatggaacc aagtataaga      540
agtttccaca ttggttggat aagtggatgt taacaagaaa gcagtttggg cttctcagtt      600 tctttttgc tgtactgcat gcaatttata gtctgtctta cccaatgagg cgatcctaca      660
gatacaagtt gctaaactgg gcatatcaac aggtccaaca aaataaagaa gatgcctgga      720
ttgagcatga tgtttggaga atggagattt atgtgtctct gggaattgtg ggattggcaa      780
tactggctct gttggctgtg acatctattc catctgtgag tgactctttg acatggagag      840
aatttcacta tattcaggta aataatatat aaaataaccc taagaggtaa atcttctttt      900
tgtgtttatg atatagaata tgttgacttt accccataaa aaataacaaa tgttttcaa      960 cagcaaagat cttatacttg ttccaattaa taatgtgctc tcctgttgtt ttccctattg     1020
cttctaatta ggacaagtgt ttcctagaca taaataaaag gcattaaaat attctttgtt     1080
```

-continued

```
ttttttttttt  tgtttgtttg  ttttttgttt  gtttgtttgt  tttttgaga  tgaagtctcg   1140
ctctgttgcc   catgctggag  tacagtggca  cgatctcggc  tcactgcaac ctgcgcctcc   1200
tgggttcagg   cgattctctt  gcctcagcct  cctgagtagc  tgggattaca ggcacccatc   1260
accatgtcca   gctaattttt  gtattttag   tagagacagg  gttttcccat gttggccagg   1320
ctggtctcga   tctcctgacc  tcaaatgatc  cgcccacctc  ggcctcccaa agtgctggga   1380
tgacagttgt   gagccaccac  actcagcctg  ctctttctaa  tatttgaaac ttgttagaca   1440
atttgctacc   catctaatgt  gatattttag  gaatccaata  tgcatggttt attatttctt   1500
aaaaaaaata   ttcttttacc  tgtcacctga  atttagtaat  gccttttatg ttacacaact   1560
tagcactttc   cagaaacaaa  aactctctcc  ttgaaataat  agagtttta  tctaccaaag   1620
atatgctagt   gtctcatttc  aaaggctgct  ttttccagct  tacattttat atacttactc   1680
acttgaagtt   tctaaatatt  cttgtaattt  taaaactatc  tcagatttac tgaggtttat   1740
cttctggtgg   tagattatcc  ataagaagag  tgatgtgcca  gaatcactct gggatccttg   1800
tctgacaaga   ttcaaaggac  taaatttaat  tcagtcatga  acactgccaa ttaccgttta   1860
tgggtagaca   tcttttggaaa tttccacaag  gtcagacatt  cgcaactatc ccttctacat   1920
gtccacacgt   atactccaac  actttattag  gcatctgatt  agtttggaaa gtatgcctcc   1980
atctgaatta   gtccagtgtg  gcttagagtt  ggtacaacat  tctcacagaa tttcctaatt   2040
ttgtaggttc   agcctgataa  ccactggagt  tctttggtcc  tcattaaata gctttcttca   2100
cacattgctc   tgcctgttac  acatatgatg  aacactgctt  tttagacttc attaggaatt   2160
taggactgca   tcttgacaac  tgagcctatt  ctactatatg  tacaatacct agcccataat   2220
aggtatacaa   tacacatttg  gtaaaactaa  ttttcaacca  atgacatgta  ttttcaact   2280
agtaacctag   aaatgtttca  cttaaaatct  gagaactggt  tacactacaa gttaccttgg   2340
agattcatat   atgaaaacgc  aaacttagct  atttgattgt  attcactggg acttaagaat   2400
gcgcctgaat   aattgtgagt  tcgatttgtt  ctggcaggct  aatgaccatt tccagtaaag   2460
tgaatagagg   tcagaagtcg  tataaaagag  gtgttgtcag  aacaccgttg agattacata   2520
ggtgaacaac   tattttaag   caactttatt  tgtgtagtga  caaagcatcc caatgcaggc   2580
tgaaatgttt   catcacatct  ctggatctct  ctattttgtg  cagacattga aaaaattgtt   2640
catattattt   ccatgttatc  agaatatttg  atttttaaa   aacataggcc aagttcattc   2700
acttcattat   tcatttatca  aaatcagagt  gaatcacatt  agtcgccttc acaactgata   2760
aagatcactg   aagtcaaatt  gatttttgct  ataatcttca  atctacctat atttaattga   2820
gaatctaaaa   tgtacaaatc  attgtgttga  ttctgcagtg  atcctgctat aagtaagact   2880
cagtccctga   ttttaggtat  cctgtgaaaa  gcagaattaa  gacaaataca caagagacaa   2940
agcacaaaaa   ataaatatca  taaggggatg  aacaaaatgg  tggagaaaga gtagacaaag   3000
tttttgatca   cctgccttca  aagaaaggct  gtgaattttg  ttcacttaga cagcttggag   3060
acaagaaatt   acccaaaagt  aaggtgagga  ggataggcaa  aaagagcaga aagatgtgaa   3120
tggacattgt   tgagaaatgt  gataggaaaa  caatcataga  taaaggattt ccaagcaaca   3180
gagcatatcc   agatgaggta  ggatgggata  aactcttatt  gaaccaatct tcaccaattt   3240
tgttttctt    ttgcagagca  agctaggaat  tgtttcccct  tctactgggca caatacacgc   3300
attgattttt   gcctggaata  agtggataga  tataaaacaa  tttgtatggt atacacctcc   3360
aactttatg    atagctgttt  tccttccaat  tgttgtcctg  atatttaaaa gcatactatt   3420
cctgccatgc   ttgaggaaga  agatactgaa  gattagacat  ggttgggaag acgtcaccaa   3480
```

-continued

```
aattaacaaa actgagatat gttcccagtt gtagaattac tgtttacaca catttttgtt    3540
caatattgat atattttatc accaacattt caagtttgta tttgttaata aaatgattat    3600
tcaaggaaaa aaaaaaaaaa aaaaaaa                                        3627

<210> SEQ ID NO 5
<211> LENGTH: 2453
<212> TYPE: DNA
<213> ORGANISM: Homo sapiens
<220> FEATURE:
<221> NAME/KEY: CDS
<222> LOCATION: (355)...(1719)

<400> SEQUENCE: 5
ggacgcgtgg gcggacgcgt gggttcctcg ggccctcggc gccacaagct gtccgggcac     60
gcagcccctc gcggcgcgtc gctgccaagc cggcctccgc gcgcctccct ccttccttct    120
cccctggctg ttcgcgatcc agcttgggta ggcggggaag cagctggagt gcgaccgcca    180
cggcagccac cctgcaaccg ccagtcggag gtgcagtccg taggccctgg ccccgggtg     240 ggcccttggg gagtcggcgc cgctcccgag gagctgcaag gctcgcccct gcccggcgtg    300
gagggcgcgg ggggcgcgga ggatattctt ggtgatcttg gaagtgtccg tatc atg     357
                                                             Met
                                                              1 gaa tca atc tct atg atg gga agc cct aag agc ctt agt gaa act tgt     405
Glu Ser Ile Ser Met Met Gly Ser Pro Lys Ser Leu Ser Glu Thr Cys
          5                  10                  15 tta cct aat ggc ata aat ggt atc aaa gat gca agg aag gtc act gta     453
Leu Pro Asn Gly Ile Asn Gly Ile Lys Asp Ala Arg Lys Val Thr Val
 20                  25                  30 ggt gtg att gga agt gga gat ttt gcc aaa tcc ttg acc att cga ctt     501
Gly Val Ile Gly Ser Gly Asp Phe Ala Lys Ser Leu Thr Ile Arg Leu
 35                  40                  45 att aga tgc ggc tat cat gtg gtc ata gga agt aga aat cct aag ttt     549
Ile Arg Cys Gly Tyr His Val Val Ile Gly Ser Arg Asn Pro Lys Phe
 50                  55                  60                  65 gct tct gaa ttt ttt cct cat gtg gta gat gtc act cat cat gaa gat     597
Ala Ser Glu Phe Phe Pro His Val Val Asp Val Thr His His Glu Asp
                 70                  75                  80 gct ctc aca aaa aca aat ata ata ttt gtt gct ata cac aga gaa cat     645
Ala Leu Thr Lys Thr Asn Ile Ile Phe Val Ala Ile His Arg Glu His
             85                  90                  95 tat acc tcc ctg tgg gac ctg aga cat ctg ctt gtg ggt aaa atc ctg     693
Tyr Thr Ser Leu Trp Asp Leu Arg His Leu Leu Val Gly Lys Ile Leu
        100                 105                 110 att gat gtg agc aat aac atg agg ata aac cag tac cca gaa tcc aat     741
Ile Asp Val Ser Asn Asn Met Arg Ile Asn Gln Tyr Pro Glu Ser Asn
115                 120                 125 gct gaa tat ttg gct tca tta ttc cca gat tct ttg att gtc aaa gga     789
Ala Glu Tyr Leu Ala Ser Leu Phe Pro Asp Ser Leu Ile Val Lys Gly
130                 135                 140                 145 ttt aat gtt gtc tca gct tgg gca ctt cag tta gga cct aag gat gcc     837
Phe Asn Val Val Ser Ala Trp Ala Leu Gln Leu Gly Pro Lys Asp Ala
                150                 155                 160 agc cgg cag gtt tat ata tgc agc aac aat att caa gcg cga caa cag     885
Ser Arg Gln Val Tyr Ile Cys Ser Asn Asn Ile Gln Ala Arg Gln Gln
            165                 170                 175 gtt att gaa ctt gcc cgc cag ttg aat ttc att ccc att gac ttg gga     933
Val Ile Glu Leu Ala Arg Gln Leu Asn Phe Ile Pro Ile Asp Leu Gly
        180                 185                 190
```

| | | | | | | | | | | | | | | | |
|---|---|---|---|---|---|---|---|---|---|---|---|---|---|---|---|
| tcc | tta | tca | tca | gcc | aga | gag | att | gaa | aat | tta | ccc | cta | cga | ctc | ttt | 981 |
| Ser | Leu | Ser | Ser | Ala | Arg | Glu | Ile | Glu | Asn | Leu | Pro | Leu | Arg | Leu | Phe |
| | 195 | | | | 200 | | | | | 205 | | | | | |

| act | ctc | tgg | aga | ggg | cca | gtg | gtg | gta | gct | ata | agc | ttg | gcc | aca | ttt | 1029 |
|---|---|---|---|---|---|---|---|---|---|---|---|---|---|---|---|---|
| Thr | Leu | Trp | Arg | Gly | Pro | Val | Val | Val | Ala | Ile | Ser | Leu | Ala | Thr | Phe |
| 210 | | | | | 215 | | | | | 220 | | | | | 225 |

| ttt | ttc | ctt | tat | tcc | ttt | gtc | aga | gat | gtg | att | cat | cca | tat | gct | aga | 1077 |
|---|---|---|---|---|---|---|---|---|---|---|---|---|---|---|---|---|
| Phe | Phe | Leu | Tyr | Ser | Phe | Val | Arg | Asp | Val | Ile | His | Pro | Tyr | Ala | Arg |
| | | | | 230 | | | | | 235 | | | | | 240 | |

| aac | caa | cag | agt | gac | ttt | tac | aaa | att | cct | ata | gag | att | gtg | aat | aaa | 1125 |
|---|---|---|---|---|---|---|---|---|---|---|---|---|---|---|---|---|
| Asn | Gln | Gln | Ser | Asp | Phe | Tyr | Lys | Ile | Pro | Ile | Glu | Ile | Val | Asn | Lys |
| | | | 245 | | | | | 250 | | | | | 255 | | |

| acc | tta | cct | ata | gtt | gcc | att | act | ttg | ctc | tcc | cta | gta | tac | ctt | gca | 1173 |
|---|---|---|---|---|---|---|---|---|---|---|---|---|---|---|---|---|
| Thr | Leu | Pro | Ile | Val | Ala | Ile | Thr | Leu | Leu | Ser | Leu | Val | Tyr | Leu | Ala |
| | 260 | | | | | 265 | | | | | 270 | | | | |

| ggt | ctt | ctg | gca | gct | gct | tat | caa | ctt | tat | tac | ggc | acc | aag | tat | agg | 1221 |
|---|---|---|---|---|---|---|---|---|---|---|---|---|---|---|---|---|
| Gly | Leu | Leu | Ala | Ala | Ala | Tyr | Gln | Leu | Tyr | Tyr | Gly | Thr | Lys | Tyr | Arg |
| 275 | | | | | 280 | | | | | 285 | | | | | |

| aga | ttt | cca | cct | tgg | ttg | gaa | acc | tgg | tta | cag | tgt | aga | aaa | cag | ctt | 1269 |
|---|---|---|---|---|---|---|---|---|---|---|---|---|---|---|---|---|
| Arg | Phe | Pro | Pro | Trp | Leu | Glu | Thr | Trp | Leu | Gln | Cys | Arg | Lys | Gln | Leu |
| 290 | | | | | 295 | | | | | 300 | | | | | 305 |

| gga | tta | cta | agt | ttt | ttc | ttc | gct | atg | gtc | cat | gtt | gcc | tac | agc | ctc | 1317 |
|---|---|---|---|---|---|---|---|---|---|---|---|---|---|---|---|---|
| Gly | Leu | Leu | Ser | Phe | Phe | Phe | Ala | Met | Val | His | Val | Ala | Tyr | Ser | Leu |
| | | | | 310 | | | | | 315 | | | | | 320 | |

| tgc | tta | ccg | atg | aga | agg | tca | gag | aga | tat | ttg | ttt | ctc | aac | atg | gct | 1365 |
|---|---|---|---|---|---|---|---|---|---|---|---|---|---|---|---|---|
| Cys | Leu | Pro | Met | Arg | Arg | Ser | Glu | Arg | Tyr | Leu | Phe | Leu | Asn | Met | Ala |
| | | | 325 | | | | | 330 | | | | | 335 | | |

| tat | cag | cag | gtt | cat | gca | aat | att | gaa | aac | tct | tgg | aat | gag | gaa | gaa | 1413 |
|---|---|---|---|---|---|---|---|---|---|---|---|---|---|---|---|---|
| Tyr | Gln | Gln | Val | His | Ala | Asn | Ile | Glu | Asn | Ser | Trp | Asn | Glu | Glu | Glu |
| | | | | 340 | | | | | 345 | | | | | 350 | |

| gtt | tgg | aga | att | gaa | atg | tat | atc | tcc | ttt | ggc | ata | atg | agc | ctt | ggc | 1461 |
|---|---|---|---|---|---|---|---|---|---|---|---|---|---|---|---|---|
| Val | Trp | Arg | Ile | Glu | Met | Tyr | Ile | Ser | Phe | Gly | Ile | Met | Ser | Leu | Gly |
| 355 | | | | | 360 | | | | | 365 | | | | | |

| tta | ctt | tcc | ctc | ctg | gca | gtc | act | tct | atc | cct | tca | gtg | agc | aat | gct | 1509 |
|---|---|---|---|---|---|---|---|---|---|---|---|---|---|---|---|---|
| Leu | Leu | Ser | Leu | Leu | Ala | Val | Thr | Ser | Ile | Pro | Ser | Val | Ser | Asn | Ala |
| 370 | | | | 375 | | | | | 380 | | | | | 385 | |

| tta | aac | tgg | aga | gaa | ttc | agt | ttt | att | cag | tct | aca | ctt | gga | tat | gtc | 1557 |
|---|---|---|---|---|---|---|---|---|---|---|---|---|---|---|---|---|
| Leu | Asn | Trp | Arg | Glu | Phe | Ser | Phe | Ile | Gln | Ser | Thr | Leu | Gly | Tyr | Val |
| | | | 390 | | | | | 395 | | | | | 400 | | |

| gct | ctc | ctc | ata | agt | act | ttc | cat | gtt | tta | att | tat | gga | tgg | aaa | cga | 1605 |
|---|---|---|---|---|---|---|---|---|---|---|---|---|---|---|---|---|
| Ala | Leu | Leu | Ile | Ser | Thr | Phe | His | Val | Leu | Ile | Tyr | Gly | Trp | Lys | Arg |
| | | 405 | | | | | 410 | | | | | 415 | | | |

| gct | ttt | gag | gaa | gag | tac | tac | aga | ttt | tat | aca | cca | cca | aac | ttt | gtt | 1653 |
|---|---|---|---|---|---|---|---|---|---|---|---|---|---|---|---|---|
| Ala | Phe | Glu | Glu | Glu | Tyr | Tyr | Arg | Phe | Tyr | Thr | Pro | Pro | Asn | Phe | Val |
| | 420 | | | | | 425 | | | | | 430 | | | | |

| ctt | gct | ctt | gtt | ttg | ccc | tca | att | gta | att | ctg | gat | ctt | ttg | cag | ctt | 1701 |
|---|---|---|---|---|---|---|---|---|---|---|---|---|---|---|---|---|
| Leu | Ala | Leu | Val | Leu | Pro | Ser | Ile | Val | Ile | Leu | Asp | Leu | Leu | Gln | Leu |
| 435 | | | | | 440 | | | | | 445 | | | | | |

| tgc | aga | tac | cca | gac | tga | gctggaactg | gaatttgtct | tcctattgac | | | | | | | | 1749 |
|---|---|---|---|---|---|---|---|---|---|---|---|---|---|---|---|---|
| Cys | Arg | Tyr | Pro | Asp | * | | | | | | | | | | |
| 450 | | | | | | | | | | | | | | | |

| | |
|---|---|
| tctacttctt taaaagcggc tgcccattac attcctcagc tgtccttgca gttaggtgta | 1809 |
| catgtgactg agtgttggcc agtgagatga agtctcctca aaggaaggca gcatgtgtcc | 1869 |
| tttttcatcc cttcatcttg ctgctgggat tgtggatata acaggagccc tggcagctgt | 1929 |
| ctccagagga tcaaagccac acccaaagag taaggcagat tagagaccag aaagaccttg | 1989 |
| actacttccc tacttccact gcttttcctg catttaagcc attgtaaatc tgggtgtgtt | 2049 |

```
acatgaagtg aaaattaatt ctttctgccc ttcagttctt tatcctgata ccatttaaca    2109
ctgtctgaat taactagact gcaataattc tttcttttga aagcttttaa aggataatgt    2169
gcaattcaca ttaaaattga ttttccattg tcaattagtt atactcattt tcctgccttg    2229
atctttcatt agatattttg tatctgcttg gaatatatta tcttcttttt aactgtgtaa    2289
ttggtaatta ctaaaactct gtaatctcca aaatattgct atcaaattac acaccatgtt    2349
ttctatcatt ctcatagatc tgccttataa acatttaaat aaaagtact atttaatgat    2409 ttaaaaaaaa aaaaaaaaaa aaaaaaaaaa aaaaaaaaaa aaaa                    2453
```

<210> SEQ ID NO 6
<211> LENGTH: 454
<212> TYPE: PRT
<213> ORGANISM: Homo sapiens

<400> SEQUENCE: 6

```
Met Glu Ser Ile Ser Met Met Gly Ser Pro Lys Ser Leu Ser Glu Thr
 1               5                  10                  15

Cys Leu Pro Asn Gly Ile Asn Gly Ile Lys Asp Ala Arg Lys Val Thr
                20                  25                  30

Val Gly Val Ile Gly Ser Gly Asp Phe Ala Lys Ser Leu Thr Ile Arg
            35                  40                  45

Leu Ile Arg Cys Gly Tyr His Val Val Ile Gly Ser Arg Asn Pro Lys
        50                  55                  60

Phe Ala Ser Glu Phe Phe Pro His Val Val Asp Val Thr His His Glu
    65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300
```

-continued

```
Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Asp Leu Leu Gln
        435                 440                 445

Leu Cys Arg Tyr Pro Asp
    450
```

```
<210> SEQ ID NO 7
<211> LENGTH: 4429
<212> TYPE: DNA
<213> ORGANISM: Homo sapiens
<220> FEATURE:
<221> NAME/KEY: CDS
<222> LOCATION: (85)...(1464)

<400> SEQUENCE: 7
```

```
cgaaacttcc ctctacccgc ccggcccgcg gcgcgcaccg ttggcgctgg acgcttcctc        60
cttggaagcg cctctccctc agtt atg gag aaa act tgt ata gat gca ctt          111
                         Met Glu Lys Thr Cys Ile Asp Ala Leu
                           1               5 cct ctt act atg aat tct tca gaa aag caa gag act gta tgt att ttt        159
Pro Leu Thr Met Asn Ser Ser Glu Lys Gln Glu Thr Val Cys Ile Phe
 10                  15                  20                  25 gga act ggt gat ttt gga aga tca ctg gga ttg aaa atg ctc cag tgt        207
Gly Thr Gly Asp Phe Gly Arg Ser Leu Gly Leu Lys Met Leu Gln Cys
                 30                  35                  40 ggt tat tct gtt gtt ttt gga agt cga aac ccc cag aag acc acc cta        255
Gly Tyr Ser Val Val Phe Gly Ser Arg Asn Pro Gln Lys Thr Thr Leu
             45                  50                  55 ctg ccc agt ggt gca gaa gtc ttg agc tat tca gaa gca gcc aag aag        303
Leu Pro Ser Gly Ala Glu Val Leu Ser Tyr Ser Glu Ala Ala Lys Lys
         60                  65                  70 tct ggc atc ata atc ata gca atc cac aga gag cat tat gat ttt ctc        351
Ser Gly Ile Ile Ile Ile Ala Ile His Arg Glu His Tyr Asp Phe Leu
     75                  80                  85 aca gaa tta act gag gtt ctc aat gga aaa ata ttg gta gac atc agc        399
Thr Glu Leu Thr Glu Val Leu Asn Gly Lys Ile Leu Val Asp Ile Ser
 90                  95                 100                 105 aac aac ctc aaa atc aat caa tat cca gaa tct aat gca gag tac ctt        447
Asn Asn Leu Lys Ile Asn Gln Tyr Pro Glu Ser Asn Ala Glu Tyr Leu
                110                 115                 120 gct cat ttg gtg cca gga gcc cac gtg gta aaa gca ttt aac acc atc        495
Ala His Leu Val Pro Gly Ala His Val Val Lys Ala Phe Asn Thr Ile
            125                 130                 135
```

| | |
|---|---|
| tca gcc tgg gct ctc cag tca gga gca ctg gat gca agt cgg cag gtg<br>Ser Ala Trp Ala Leu Gln Ser Gly Ala Leu Asp Ala Ser Arg Gln Val<br>140 145 150 | 543 |
| ttt gtg tgt gga aat gac agc aaa gcc aag caa aga gtg atg gat att<br>Phe Val Cys Gly Asn Asp Ser Lys Ala Lys Gln Arg Val Met Asp Ile<br>155 160 165 | 591 |
| gtt cgt aat ctt gga ctt act cca atg gat caa gga tca ctc atg gca<br>Val Arg Asn Leu Gly Leu Thr Pro Met Asp Gln Gly Ser Leu Met Ala<br>170 175 180 185 | 639 |
| gcc aaa gaa att gaa aag tac ccc ctg cag cta ttt cca atg tgg agg<br>Ala Lys Glu Ile Glu Lys Tyr Pro Leu Gln Leu Phe Pro Met Trp Arg<br>190 195 200 | 687 |
| ttc ccc ttc tat ttg tct gct gtg ctg tgt gtc ttc ttg ttt ttc tat<br>Phe Pro Phe Tyr Leu Ser Ala Val Leu Cys Val Phe Leu Phe Phe Tyr<br>205 210 215 | 735 |
| tgt gtt ata aga gac gta atc tac cct tat gtt tat gaa aag aaa gat<br>Cys Val Ile Arg Asp Val Ile Tyr Pro Tyr Val Tyr Glu Lys Lys Asp<br>220 225 230 | 783 |
| aat aca ttt cgt atg gct att tcc att cca aat cgt atc ttt cca ata<br>Asn Thr Phe Arg Met Ala Ile Ser Ile Pro Asn Arg Ile Phe Pro Ile<br>235 240 245 | 831 |
| aca gca ctt aca ctg ctt gct ttg gtt tac ctc cct ggt gtt att gct<br>Thr Ala Leu Thr Leu Leu Ala Leu Val Tyr Leu Pro Gly Val Ile Ala<br>250 255 260 265 | 879 |
| gcc att cta caa ctg tac cga ggc aca aaa tac cgt cga ttc cca gac<br>Ala Ile Leu Gln Leu Tyr Arg Gly Thr Lys Tyr Arg Arg Phe Pro Asp<br>270 275 280 | 927 |
| tgg ctt gac cac tgg atg ctt tgc cga aag cag ctt ggc ttg gta gct<br>Trp Leu Asp His Trp Met Leu Cys Arg Lys Gln Leu Gly Leu Val Ala<br>285 290 295 | 975 |
| ctg gga ttt gcc ttc ctt cat gtc ctc tac aca ctt gtg att cct att<br>Leu Gly Phe Ala Phe Leu His Val Leu Tyr Thr Leu Val Ile Pro Ile<br>300 305 310 | 1023 |
| cga tat tat gta cga tgg aga ttg gga aac tta acc gtt acc cag gca<br>Arg Tyr Tyr Val Arg Trp Arg Leu Gly Asn Leu Thr Val Thr Gln Ala<br>315 320 325 | 1071 |
| ata ctc aag aag gag aat cca ttt agc acc tcc tca gcc tgg ctc agt<br>Ile Leu Lys Lys Glu Asn Pro Phe Ser Thr Ser Ser Ala Trp Leu Ser<br>330 335 340 345 | 1119 |
| gat tca tat gtg gct ttg gga ata ctt ggg ttt ttt ctg ttt gta ctc<br>Asp Ser Tyr Val Ala Leu Gly Ile Leu Gly Phe Phe Leu Phe Val Leu<br>350 355 360 | 1167 |
| ttg gga atc act tct ttg cca tct gtt agc aat gca gtc aac tgg aga<br>Leu Gly Ile Thr Ser Leu Pro Ser Val Ser Asn Ala Val Asn Trp Arg<br>365 370 375 | 1215 |
| gag ttc cga ttt gtc cag tcc aaa ctg ggt tat ttg acc ctg atc ttg<br>Glu Phe Arg Phe Val Gln Ser Lys Leu Gly Tyr Leu Thr Leu Ile Leu<br>380 385 390 | 1263 |
| tgt aca gcc cac acc ctg gtg tac ggt ggg aag aga ttc ctc agc cct<br>Cys Thr Ala His Thr Leu Val Tyr Gly Gly Lys Arg Phe Leu Ser Pro<br>395 400 405 | 1311 |
| tca aat ctc aga tgg tat ctt cct gca gcc tac gtg tta ggg ctt atc<br>Ser Asn Leu Arg Trp Tyr Leu Pro Ala Ala Tyr Val Leu Gly Leu Ile<br>410 415 420 425 | 1359 |
| att cct tgc act gtg ctg gtg atc aag ttt gtc cta atc atg cca tgt<br>Ile Pro Cys Thr Val Leu Val Ile Lys Phe Val Leu Ile Met Pro Cys<br>430 435 440 | 1407 |
| gta gac aac acc ctt aca agg atc cgc cag ggc tgg gaa agg aac tca<br>Val Asp Asn Thr Leu Thr Arg Ile Arg Gln Gly Trp Glu Arg Asn Ser<br>445 450 455 | 1455 |

```
aaa cac tag aaaaagcatt gaatggaaaa tcaatattta aaacaaagtt       1504
Lys His  * caatttagct ggatttctga actatggttt tgaatgttta aagaagaatg atgggtacag   1564
ttaggaaagt ttttttctta caccgtgact gagggaaaca ttgcttgtct ttgagaaatt   1624
gactgacata ctggaagaga acaccatttt atctcaggtt agtgaagaat cagtgcaggt   1684
ccctgactct tattttccca gaggccatgg agctgagatt gagactagcc ttgtggtttc   1744
acactaaaga gtttccttgt tatgggcaac atgcatgacc taatgtcttg caaaatccaa   1804
tagaagtatt gcagcttcct tctctggctc aagggctgag ttaagtgaaa ggaaaaacag   1864
cacaatggtg accactgata aaggctttat taggtatatc tgaggaagtg ggtcacatga   1924
aatgtaaaaa gggaatgagg ttttgttgt tttttggaag taaaggcaaa cataaatatt    1984
accatgatga attctagtga aatgacccct tgactttgct tttcttaata cagatattta   2044
ctgagaggaa ctattttat aacacaagaa aaatttacaa ttgattaaaa gtatccatgt    2104
cttggataca tacgtatcta tagagctggc atgtaattct tcctctataa agaataggta   2164
taggaaagac tgaataaaaa tggagggata tccccttgga tttcacttgc attgtgcaat   2224
aagcaaagaa gggttgataa aagttcttga tcaaaaagtt caaagaaacc agaattttag   2284
acagcaagct aaataaatat tgtaaaattg cactatatta ggttaagtat tatttaggta   2344
ttataatatg ctttgtaaat tttatattcc aaatattgct caatattttt catctattaa   2404 attaattct agtgtaaata agtagcttct atatctgtct tagtctatta taattgtaag    2464
gagtaaaatt aaatgaatag tctgcaggta taaatttgaa caatgcatag atgatcgaaa   2524
attacggaaa atcatagggc agagaggtgt gaagattcat cattatgtga aatttggatc   2584
tttctcaaat ccttgctgaa atttaggatg gttctcactg ttttttctgtg ctgatagtac  2644 cctttccaag gtgaccttca gggggattaa ccttcctagc tcaagcaatg agctaaaagg   2704
agccttatgc atgatcttcc cacatatcaa aataactaaa aggcactgag tttggcattt    2764
ttctgcctgc tctgctaaga cctttttttt tttttacttt tcattataac atattataca    2824
tgacattata caaaaatgat taaaatatat taaaacaaca tcaacaatcc aggatatttt    2884
tctataaaac ttttaaaaa taattgtatc tatatattca attttacatc ctttttcaaa     2944
ggctttgttt ttctaaaggc tttgttttcc tttttattat tttttctttt tttattttttt  3004 tgagacagtc ttgctctgtc gctcaggctg gagtgcagtg gcacgatctc agctcactgc    3064
aacctcctcc tcccaggttc aagtgattct tgttcatcag cctcccgagt agctgggact    3124
acaggcatgt gccactatgc ccagctaatt tttgtacttt tagtagagac agggtttcac    3184
cacattggtc aggctggtct tgaaatgctg gcgtcaagtg atctgcctgc ctccgcctta    3244
cgtaatatat ttcttaatg gctgcataat atcacatcaa ataggcattt ttcaaacctc     3304
tttccttatt aaacatgtag actatatcca tttttttacta aaataaataa catttcagat   3364
aatatctttg cactgataat gttgccaagc catttctaaa gtgaccttat caatttaatt    3424
accattggat gagggtgttg ctttcatcgc accattgtag attgtctttt ttatttcaat    3484
ttgcgtttat ttataactgg ttgcaaaggt acacagaaca cacgctcctt caacttatct    3544
ttgataaacc caagcaagga tacaaaaagt tggacgacat tgagtagagt catggtatac    3604
ggtgctgacc ctacagtatc agtggaaaag ataaggaaaa tgtcactact cacctatgtt    3664
atgcaaaaca gttaggtgtg ctgggctgg atactgctct tttacttgag cattggttga    3724
ttaaagttta ggtaccatcc aggctggtct agagaagtct ttggagttaa ccatgctctt   3784
```

-continued

```
tttgttaaag aagagagtaa tgtgtttatc ctggctcata gtccgtcacc gaaaatagaa    3844
aatgccatcc ataggtaaaa tgctgaccta tagaaaaaaa tgaactctac ttttatagcc    3904
tagtaaaaat gctctacctg agtagttaaa agcaattcat gaagcctgaa gctaaagagc    3964
actctgatgg ttttggcata atagctgcat ttccagacct gacctttggc cccaaccaca    4024
agtgctccaa gccccaccag ctgaccaaag aaagcccaag ttctccttct gtccttccca    4084
caacctccct gctcccaaaa ctatgaaatt aatttgacca tattaacaca gctgactcct    4144
ccagtttact taaggtagaa agaatgagtt tacaacagat gaaataagt gctttgggcg     4204 aactgtattc cttttaacag atccaaacta ttttacattt aaaaaaaaag ttaaactaaa    4264
cttctttact gctgatatgt ttcctgtatt ctagaaaaat ttttacactt tcacattatt    4324
tttgtacact ttccccatgt taagggatga tggctttat aaatgtgtat tcattaaatg     4384
ttactttaaa aataaaaaaa aaaaaaaaaa aaaaaaaaa aaaaa                     4429
```

<210> SEQ ID NO 8
<211> LENGTH: 459
<212> TYPE: PRT
<213> ORGANISM: Homo sapiens

<400> SEQUENCE: 8

```
Met Glu Lys Thr Cys Ile Asp Ala Leu Pro Leu Thr Met Asn Ser Ser
 1               5                  10                  15

Glu Lys Gln Glu Thr Val Cys Ile Phe Gly Thr Gly Asp Phe Gly Arg
            20                  25                  30

Ser Leu Gly Leu Lys Met Leu Gln Cys Gly Tyr Ser Val Val Phe Gly
        35                  40                  45

Ser Arg Asn Pro Gln Lys Thr Thr Leu Leu Pro Ser Gly Ala Glu Val
    50                  55                  60

Leu Ser Tyr Ser Glu Ala Ala Lys Lys Ser Gly Ile Ile Ile Ile Ala
65                  70                  75                  80

Ile His Arg Glu His Tyr Asp Phe Leu Thr Glu Leu Thr Glu Val Leu
                85                  90                  95

Asn Gly Lys Ile Leu Val Asp Ile Ser Asn Asn Leu Lys Ile Asn Gln
            100                 105                 110

Tyr Pro Glu Ser Asn Ala Glu Tyr Leu Ala His Leu Val Pro Gly Ala
        115                 120                 125

His Val Val Lys Ala Phe Asn Thr Ile Ser Ala Trp Ala Leu Gln Ser
    130                 135                 140

Gly Ala Leu Asp Ala Ser Arg Gln Val Phe Val Cys Gly Asn Asp Ser
145                 150                 155                 160

Lys Ala Lys Gln Arg Val Met Asp Ile Val Arg Asn Leu Gly Leu Thr
                165                 170                 175

Pro Met Asp Gln Gly Ser Leu Met Ala Ala Lys Glu Ile Glu Lys Tyr
            180                 185                 190

Pro Leu Gln Leu Phe Pro Met Trp Arg Phe Pro Phe Tyr Leu Ser Ala
        195                 200                 205

Val Leu Cys Val Phe Leu Phe Phe Tyr Cys Val Ile Arg Asp Val Ile
    210                 215                 220

Tyr Pro Tyr Val Tyr Glu Lys Lys Asp Asn Thr Phe Arg Met Ala Ile
225                 230                 235                 240

Ser Ile Pro Asn Arg Ile Phe Pro Ile Thr Ala Leu Thr Leu Leu Ala
                245                 250                 255
```

Leu Val Tyr Leu Pro Gly Val Ile Ala Ala Ile Leu Gln Leu Tyr Arg
            260                 265                 270

Gly Thr Lys Tyr Arg Arg Phe Pro Asp Trp Leu Asp His Trp Met Leu
        275                 280                 285

Cys Arg Lys Gln Leu Gly Leu Val Ala Leu Gly Phe Ala Phe Leu His
    290                 295                 300

Val Leu Tyr Thr Leu Val Ile Pro Ile Arg Tyr Tyr Val Arg Trp Arg
305                 310                 315                 320

Leu Gly Asn Leu Thr Val Thr Gln Ala Ile Leu Lys Lys Glu Asn Pro
                325                 330                 335

Phe Ser Thr Ser Ser Ala Trp Leu Ser Asp Ser Tyr Val Ala Leu Gly
            340                 345                 350

Ile Leu Gly Phe Phe Leu Phe Val Leu Leu Gly Ile Thr Ser Leu Pro
        355                 360                 365

Ser Val Ser Asn Ala Val Asn Trp Arg Glu Phe Arg Phe Val Gln Ser
    370                 375                 380

Lys Leu Gly Tyr Leu Thr Leu Ile Leu Cys Thr Ala His Thr Leu Val
385                 390                 395                 400

Tyr Gly Gly Lys Arg Phe Leu Ser Pro Ser Asn Leu Arg Trp Tyr Leu
                405                 410                 415

Pro Ala Ala Tyr Val Leu Gly Leu Ile Ile Pro Cys Thr Val Leu Val
            420                 425                 430

Ile Lys Phe Val Leu Ile Met Pro Cys Val Asp Asn Thr Leu Thr Arg
        435                 440                 445

Ile Arg Gln Gly Trp Glu Arg Asn Ser Lys His
    450                 455

<210> SEQ ID NO 9
<211> LENGTH: 322
<212> TYPE: DNA
<213> ORGANISM: Homo sapiens

<400> SEQUENCE: 9
ggtcgacttt tcctttattc ctttgtcaga gatctgattc atccatatgc tagaaaccaa      60
cagagtgact tttacaaaat tcctatagag attgtgaata aaaccttacc tatagttgcc     120
attactttgc tctccctagt ataccttgca ggtcttctgg cagctgctta tcaactttat     180
tacggcacca agtataggag atttccacct tggttggaaa cctggttaca gtgtagaaaa     240
cagcttggat tactaagttg tttcttcgct atggtccatg ttgcctacag cctctgctta     300
ccgatgagaa ggtcagagag at                                              322

<210> SEQ ID NO 10
<211> LENGTH: 183
<212> TYPE: DNA
<213> ORGANISM: Homo sapiens

<400> SEQUENCE: 10
tttgcagctt tgcagatacc cagactgagc tggaactgga atttgtcttc ctattgactc      60
tacttcttta aaagcggctg cccattacat tcctcagctg tccttgcagt taggtgtaca     120
tgtgactgag tgttggccag tgagatgaag tctcctcaaa ggaaggcagc atgtgtcctt     180
ttt                                                                   183

<210> SEQ ID NO 11
<211> LENGTH: 448
<212> TYPE: DNA

<213> ORGANISM: Homo sapiens

<400> SEQUENCE: 11

```
aagaaggaga atccatttag cacctcctca gcctggctca gtgattcata tgtggctttg    60
ggaatacttg ggttttttct gtttgtactc ttgggaatca cttctttgcc atctgttagc   120
aatgcagtca actggagaga gttccgattt gtccagtcca aactgggtta tttgaccctg   180
atcttgtgta cagcccacac cctggtgtac ggtgggaaga gattcctcag cccttcaaat   240
ctcagatggt atcttcctgc agcctacgtg ttagggctta tcattccttg cactgtgctg   300
gtgatcaagt ttgtcctaat catgccatgt gtagacaaca cccttacaag gatccgccag   360
ggctgggaaa ggaactcaaa acactagaaa aagcattgaa tggaaaatca atatttaaaa   420
caaagttcaa tttagctgga aaaaaaaa                                      448
```

<210> SEQ ID NO 12
<211> LENGTH: 401
<212> TYPE: DNA
<213> ORGANISM: Homo sapiens
<220> FEATURE:
<221> NAME/KEY: misc_feature
<222> LOCATION: 11,56,233,250,310,326,377,398
<223> OTHER INFORMATION: n=a, t, c, or g

<400> SEQUENCE: 12

```
ggccgcggca nccgctacga cctggtcaac ctggcagtca agcaggtctt ggccanacaa    60
gagccacctc tgggtgaagg aggaggtctg gcggatggag atctacctct ccctgggagt   120
gctggccctc ggcacgttgt ccctgctggc cgtgacctca ctgccgtcca ttgcaaactc   180
gctcaactgg agggagttca gcttcgttca gtcctcactg gctttgtgg ccntcgtgct   240
gagcacactn cacacgctca cctacggctg gacccgcgcc ttcgaggaga gccgctacaa   300
gttctacctn cctcccacct tcacgntcac gctgctggtg ccctgcgttc gttcatcctg   360
ggccaaagcc ctgtttntac tgccttgcat tcagccgnag a                       401
```

<210> SEQ ID NO 13
<211> LENGTH: 133
<212> TYPE: PRT
<213> ORGANISM: Homo sapiens
<220> FEATURE:
<223> OTHER INFORMATION: Xaa = Any amino acid

<400> SEQUENCE: 13

```
Ala Ala Ala Xaa Ala Thr Thr Trp Ser Thr Trp Gln Ser Ser Arg Ser
 1               5                  10                  15

Trp Pro Xaa Lys Ser His Leu Trp Val Lys Glu Glu Val Trp Arg Met
             20                  25                  30

Glu Ile Tyr Leu Ser Leu Gly Val Leu Ala Leu Gly Thr Leu Ser Leu
         35                  40                  45

Leu Ala Val Thr Ser Leu Pro Ser Ile Ala Asn Ser Leu Asn Trp Arg
     50                  55                  60

Glu Phe Ser Phe Val Gln Ser Ser Leu Gly Phe Val Ala Xaa Val Leu
 65                  70                  75                  80

Ser Thr Leu His Thr Leu Thr Tyr Gly Trp Thr Arg Ala Phe Glu Glu
                 85                  90                  95

Ser Arg Tyr Lys Phe Tyr Leu Pro Pro Thr Phe Thr Xaa Thr Leu Leu
            100                 105                 110

Val Pro Cys Val Arg Ser Ser Trp Ala Lys Ala Leu Phe Xaa Leu Pro
        115                 120                 125
```

Cys Ile Gln Pro Xaa
130

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
actttgttga tgaccaggat tgga                                          24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
cagaacttca gcacacacag gaac                                          24

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
ttaggacaac ttgatcacca gca                                           23

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
tgtccagtcc aaactgggtt attt                                          24

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
agggagttca gcttcgttca gtc                                           23

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
ggtagaactt gtagcggctc tcct                                          24

<210> SEQ ID NO 20
<211> LENGTH: 24

```
<212> TYPE: DNA
<213> ORGANISM: Artificial Sequence
<220> FEATURE:
<223> OTHER INFORMATION: primer

<400> SEQUENCE: 20
gactgagctg gaactggaat ttgt                                           24

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
tttgaggaga cttcatctca ctgg                                           24

<210> SEQ ID NO 22
<211> LENGTH: 14
<212> TYPE: DNA
<213> ORGANISM: Artificial Sequence
<220> FEATURE:
<223> OTHER INFORMATION: primer

<400> SEQUENCE: 22
ttttgtacaa gctt                                                      14

<210> SEQ ID NO 23
<211> LENGTH: 44
<212> TYPE: DNA
<213> ORGANISM: Artificial Sequence
<220> FEATURE:
<223> OTHER INFORMATION: adaptor

<400> SEQUENCE: 23
ctaatacgac tcactatagg gctcgagcgg ccgcccgggc aggt                     44

<210> SEQ ID NO 24
<211> LENGTH: 10
<212> TYPE: DNA
<213> ORGANISM: Artificial Sequence
<220> FEATURE:
<223> OTHER INFORMATION: adaptor

<400> SEQUENCE: 24
ggcccgtcca                                                           10

<210> SEQ ID NO 25
<211> LENGTH: 42
<212> TYPE: DNA
<213> ORGANISM: Artificial Sequence
<220> FEATURE:
<223> OTHER INFORMATION: adaptor

<400> SEQUENCE: 25
gtaatacgac tcactatagg gcagcgtggt cgcggccgag gt                       42

<210> SEQ ID NO 26
<211> LENGTH: 8
<212> TYPE: DNA
<213> ORGANISM: Artificial Sequence
<220> FEATURE:
<223> OTHER INFORMATION: adaptor

<400> SEQUENCE: 26
``` cggctcca                                                                    8

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
ctaatacgac tcactatagg gc                                                   22

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tcgagcggcc gcccgggcag gt                                                   22

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
agcgtggtcg cggccgaggt                                                      20

<210> SEQ ID NO 30
<211> LENGTH: 15
<212> TYPE: PRT
<213> ORGANISM: Homo sapiens

<400> SEQUENCE: 30

Tyr Gln Gln Val Gln Gln Asn Lys Glu Asp Ala Trp Ile Glu His
 1               5                  10                  15

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
gactgagctg gaactggaat ttgt                                                 24

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
tttgaggaga cttcatctca ctgg                                                 24

<210> SEQ ID NO 33
<211> LENGTH: 22
<212> TYPE: DNA
<213> ORGANISM: Artificial Sequence
<220> FEATURE:

<223> OTHER INFORMATION: primer

<400> SEQUENCE: 33
acaagagcca cctctgggtg aa                                           22

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
agttgagcga gtttgcaatg gac                                          23

<210> SEQ ID NO 35
<211> LENGTH: 16
<212> TYPE: PRT
<213> ORGANISM: Homo sapiens

<400> SEQUENCE: 35

Trp Lys Met Lys Pro Arg Arg Arg Asn Leu Glu Glu Asp Asp Tyr Leu
 1               5                  10                  15

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
actttgttga tgaccaggat tgga                                         24

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
cagaacttca gcacacacag gaac                                         24

<210> SEQ ID NO 38
<211> LENGTH: 9
<212> TYPE: PRT
<213> ORGANISM: Homo sapiens

<400> SEQUENCE: 38

Gly Leu Leu Ser Phe Phe Phe Ala Val
 1               5

<210> SEQ ID NO 39
<211> LENGTH: 9
<212> TYPE: PRT
<213> ORGANISM: Homo sapiens

<400> SEQUENCE: 39

Phe Leu Tyr Thr Leu Leu Arg Glu Val
 1               5

<210> SEQ ID NO 40
<211> LENGTH: 9
<212> TYPE: PRT

<213> ORGANISM: Homo sapiens

<400> SEQUENCE: 40

Leu Leu Leu Gly Thr Ile His Ala Leu
1               5

<210> SEQ ID NO 41
<211> LENGTH: 9
<212> TYPE: PRT
<213> ORGANISM: Homo sapiens

<400> SEQUENCE: 41

Leu Ile Phe Lys Ser Ile Leu Phe Leu
1               5

<210> SEQ ID NO 42
<211> LENGTH: 9
<212> TYPE: PRT
<213> ORGANISM: Homo sapiens

<400> SEQUENCE: 42

Met Leu Thr Arg Lys Gln Phe Gly Leu
1               5

<210> SEQ ID NO 43
<211> LENGTH: 9
<212> TYPE: PRT
<213> ORGANISM: Homo sapiens

<400> SEQUENCE: 43

Phe Leu Tyr Ser Phe Val Arg Asp Val
1               5

<210> SEQ ID NO 44
<211> LENGTH: 9
<212> TYPE: PRT
<213> ORGANISM: Homo sapiens

<400> SEQUENCE: 44

Ala Leu Leu Ile Ser Thr Phe His Val
1               5

<210> SEQ ID NO 45
<211> LENGTH: 9
<212> TYPE: PRT
<213> ORGANISM: Homo sapiens

<400> SEQUENCE: 45

Leu Leu Ser Phe Phe Phe Ala Met Val
1               5

<210> SEQ ID NO 46
<211> LENGTH: 9
<212> TYPE: PRT
<213> ORGANISM: Homo sapiens

<400> SEQUENCE: 46

Gly Leu Leu Ser Phe Phe Phe Ala Met
1               5

<210> SEQ ID NO 47
<211> LENGTH: 9
<212> TYPE: PRT
<213> ORGANISM: Homo sapiens

-continued

```
<400> SEQUENCE: 47

Ser Leu Trp Asp Leu Arg His Leu Leu
 1               5
```